US009023257B2

(12) United States Patent
Sahler et al.

(10) Patent No.: US 9,023,257 B2
(45) Date of Patent: May 5, 2015

(54) HYDROPHILICITY ALTERATION SYSTEM AND METHOD

(71) Applicant: Aaren Scientific, Inc., Ontario (CA)

(72) Inventors: Ruth Sahler, Costa Mesa, CA (US); Stephen Q. Zhou, Irvine, CA (US); Josef F. Bille, Heidelberg (DE)

(73) Assignee: Perfect IP, LLC, Dallas, TX (US)

( * ) Notice: Subject to any disclaimer, the term of this patent is extended or adjusted under 35 U.S.C. 154(b) by 0 days.

(21) Appl. No.: 13/843,464

(22) Filed: Mar. 15, 2013

(65) Prior Publication Data
US 2014/0135920 A1    May 15, 2014

Related U.S. Application Data

(60) Provisional application No. 61/726,383, filed on Nov. 14, 2012.

(51) Int. Cl.
| | | |
|---|---|---|
| *B29D 11/00* | (2006.01) | |
| *A61F 2/16* | (2006.01) | |
| *A61F 9/008* | (2006.01) | |

(52) U.S. Cl.
CPC .................. *A61F 2/16* (2013.01); *A61F 2/1613* (2013.01); *A61F 2/1627* (2013.01); *A61F 2/1648* (2013.01); *A61F 9/008* (2013.01); *A61F 9/00834* (2013.01); *B29D 11/00125* (2013.01)

(58) Field of Classification Search
USPC .......................................................... 264/2.6
See application file for complete search history.

(56) References Cited

U.S. PATENT DOCUMENTS

| | | |
|---|---|---|
| 5,100,689 A | 3/1992 | Goldberg et al. |
| 5,260,093 A | 11/1993 | Kamel et al. |
| 6,011,082 A | 1/2000 | Wang et al. |

(Continued)

OTHER PUBLICATIONS

Correa et al., "Femtosecond Laser in Polymeric Materials: Microfabrication of Doped Structures and Micromachining". IEEE Journal of Selected Topics in Quantom Electronics, vol. 18, No. 1, Jan./Feb. 2012; p. 176-186; p. 176, col. 2, para 1; p. 177, col. 1, para 1-2; p. 177, col. 2, para 4; p. 178, col. 1, para 2-3; p. 178, col. 2, para 2; p. 178, col. 2, para 4; p. 181, col. 1, para 1; figres 2, 3 and 5; abstract.

(Continued)

*Primary Examiner* — Mathieu D. Vargot
(74) *Attorney, Agent, or Firm* — David W. Carstens; Kevin M. Klughart; Carstens & Cahoon, LLP

(57) ABSTRACT

A system/method allowing hydrophilicity alteration of a polymeric material (PM) is disclosed. The PM hydrophilicity alteration changes the PM characteristics by decreasing the PM refractive index, increasing the PM electrical conductivity, and increasing the PM weight. The system/method incorporates a laser radiation source that generates tightly focused laser pulses within a three-dimensional portion of the PM to affect these changes in PM properties. The system/method may be applied to the formation of customized intraocular lenses comprising material (PLM) wherein the lens created using the system/method is surgically positioned within the eye of the patient. The implanted lens refractive index may then be optionally altered in situ with laser pulses to change the optical properties of the implanted lens and thus achieve optimal corrected patient vision. This system/method permits numerous in situ modifications of an implanted lens as the patient's vision changes with age.

27 Claims, 48 Drawing Sheets

(56) References Cited

U.S. PATENT DOCUMENTS

| 2002/0117624 A1 | 8/2002 | Katayama et al. |
| 2008/0001320 A1 | 1/2008 | Knox et al. |
| 2009/0143858 A1 | 6/2009 | Knox et al. |
| 2010/0294749 A1 | 11/2010 | Kempe et al. |

OTHER PUBLICATIONS

Wang et al., "Polymer Hydrophilicity and Hydrophobicity Inducted by Femtosecond Laser". Applied Physics Letters 95, 111110 )2009), p. 1-3; p. 2, col. 2, para 2-3.

Oujja et al., "Three Dimensional Microstructuring of Biopolymers by Femtosecond Laser Irradiation". Applied Physics Letters 95, 263730 (Dec. 2009), p. 1-3; p. 1, col. 2, para 2.

Abbasi et al., "Bulk and surface modification of silicone rubber for biomedical applications". Polym Int 51:882-888 (2002)—the entire document.

Schaffer et al., Micronnachining bulk glass by use of femtosecond laser pulses with nanojoule energy:. Optic Letters, vol. 26, No. 2, Jan. 15, 2001—the entire document.

P. J. Scully, et al., "Femtosecond laser irradiation of polymethylmethacrylte for refractive index gratings"; Journal of Optics A: Pue Appl Opt. 5 (2003) S92-S96.

Li Ding, et al., "Large enhancement of femtosecond laser mircromachining speed in dye-doped hydrogel polymers"; Dec. 22, 2008 / vol. 16, No. 26/Optics Express 21914.

*Prior Art*

*Prior Art*

*Prior Art*

FIG. 8
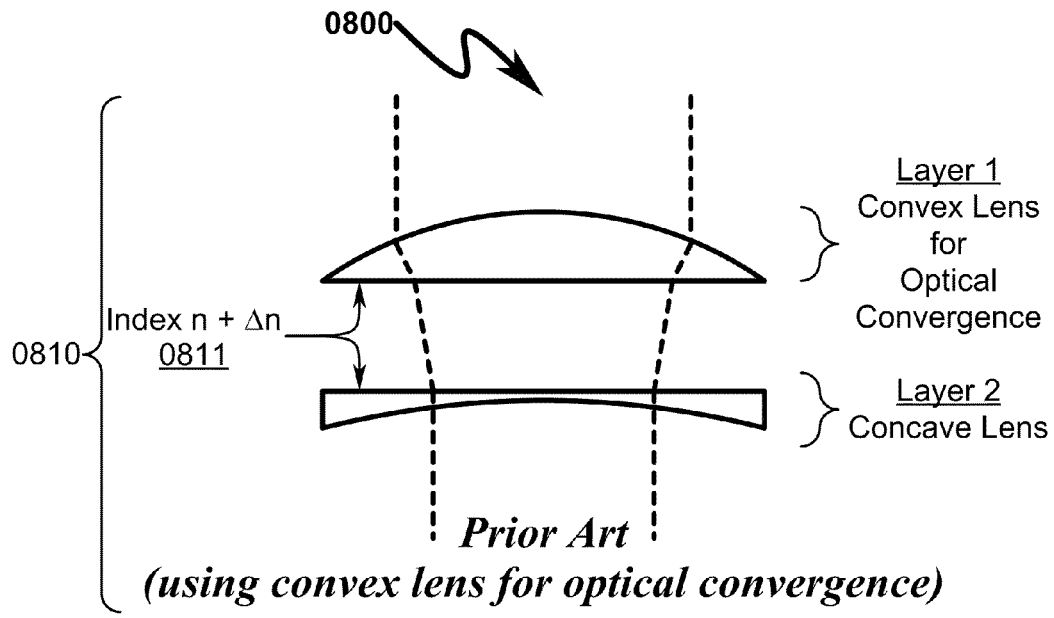
*Prior Art*
*(using convex lens for optical convergence)*
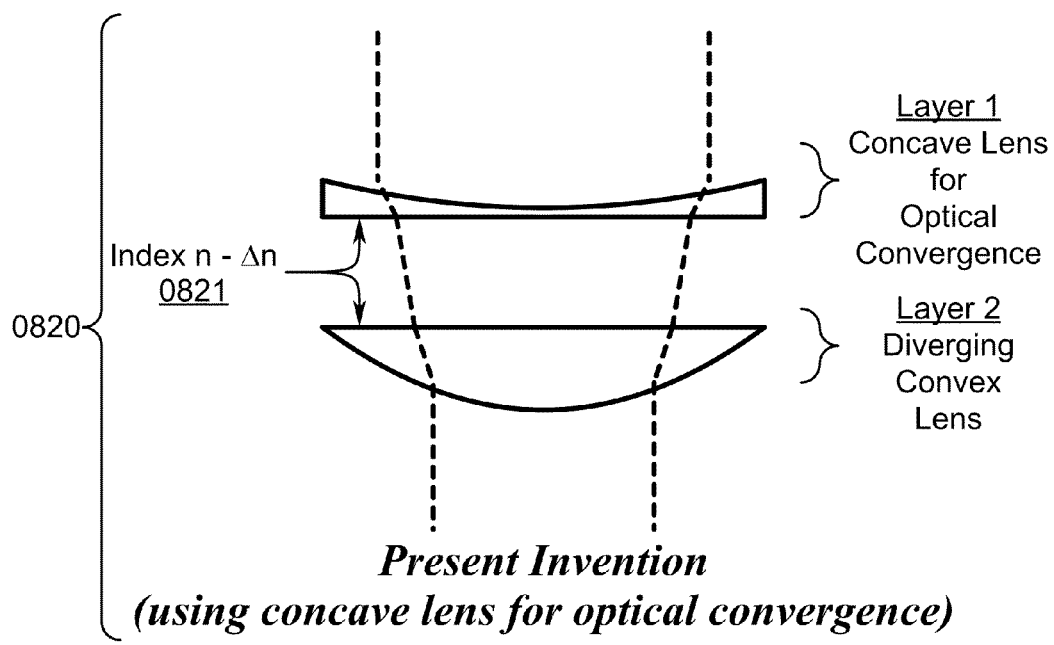
*Present Invention*
*(using concave lens for optical convergence)*

*FIG. 9*
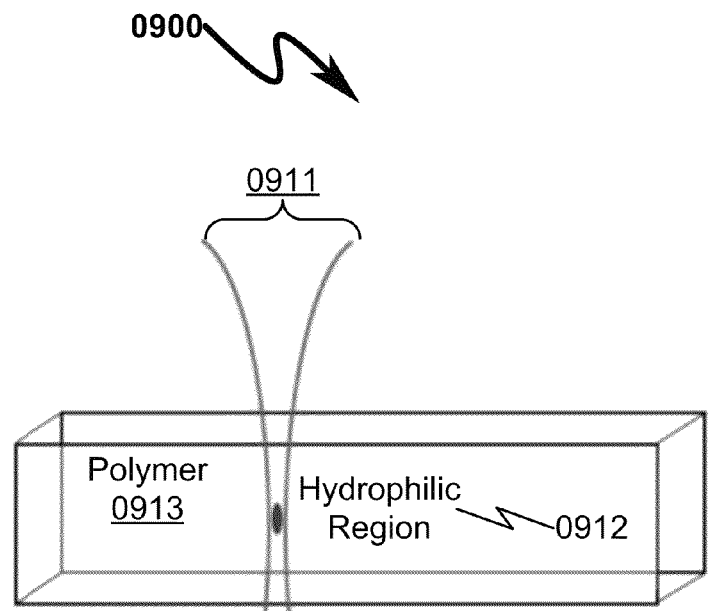
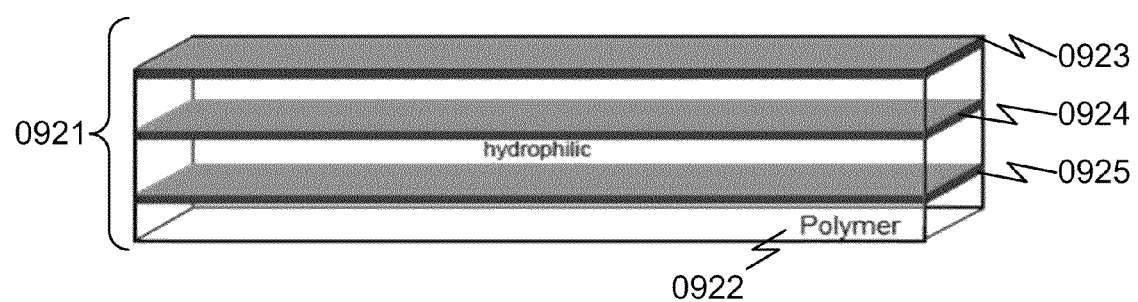

FIG. 10
1000
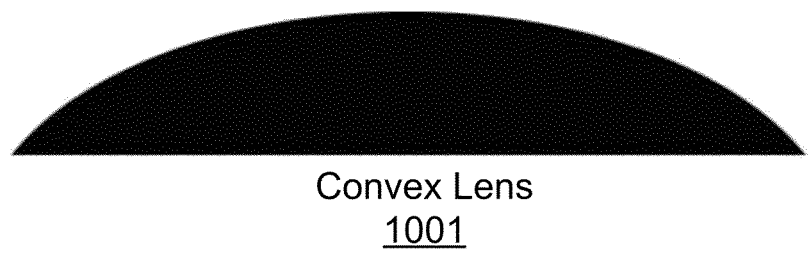
Convex Lens
1001
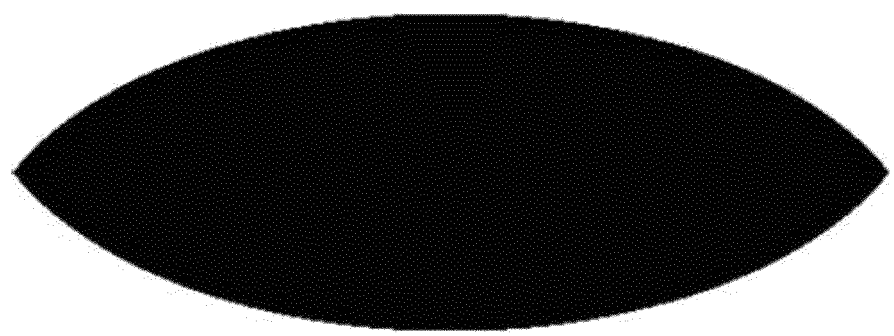
Biconvex Lens
1002

FIG. 12
1200
Phase Wrapping Convex Lens
1201
Phase Wrapping Concave Lens
1202
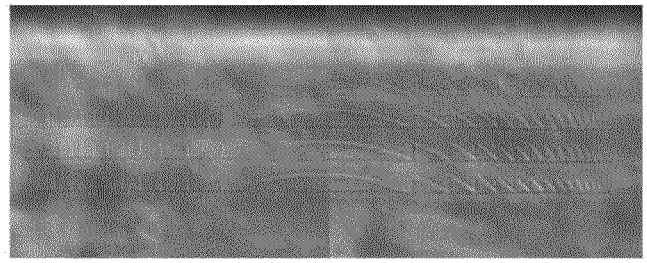
Phase Wrapping Lens Stack Example
1203
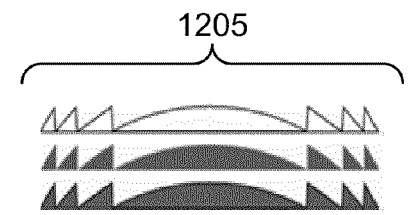
1205
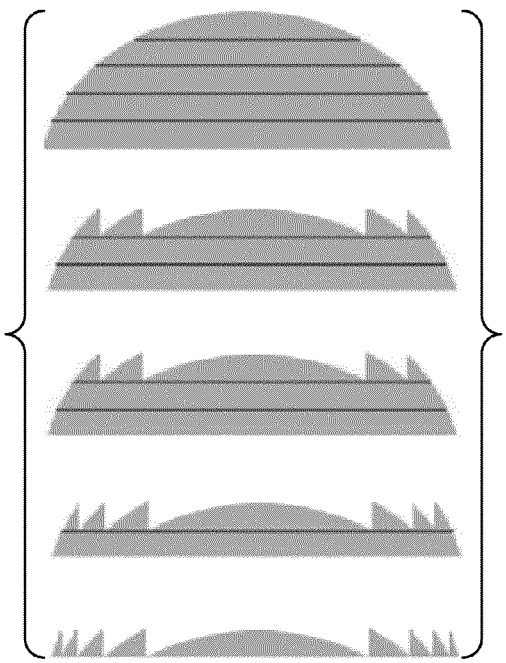
Phase Wrapping Lens Concept 1204
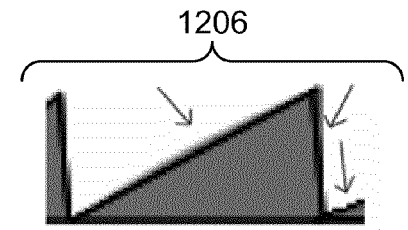
1206

FIG. 13
1300
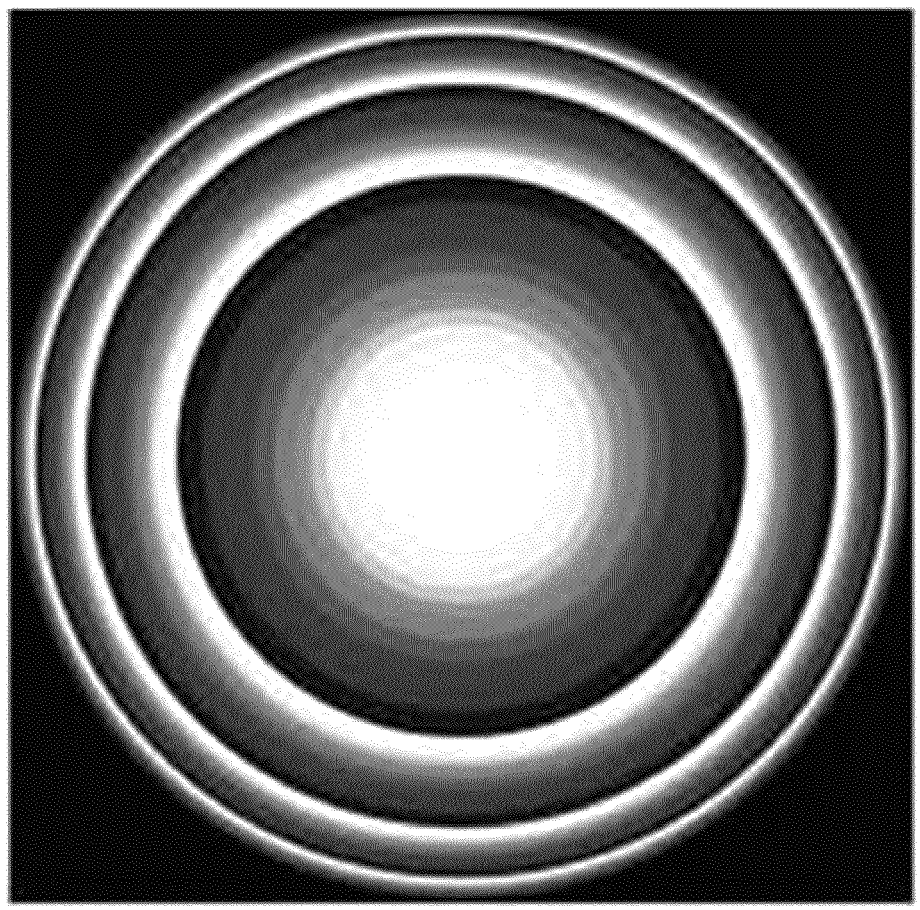
Refractive Index Gradient Lens
1301
Refractive Index Gradient Lens
(Side View)
1302

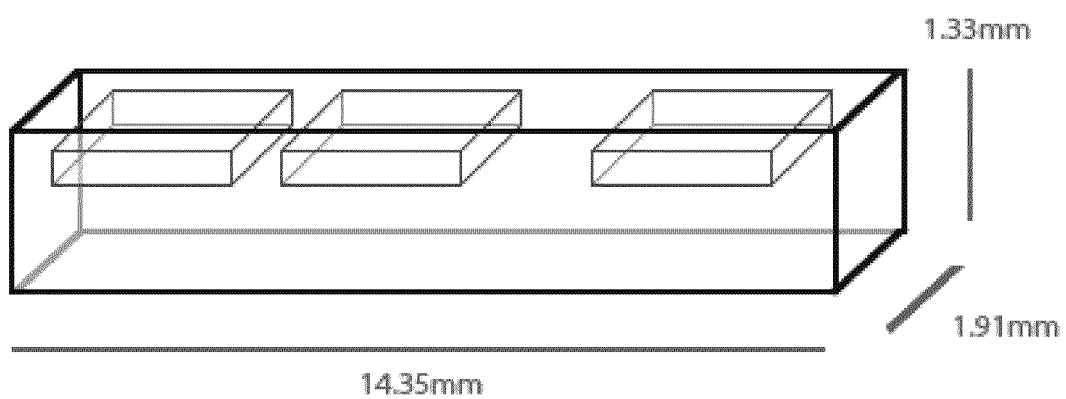

FIG. 21
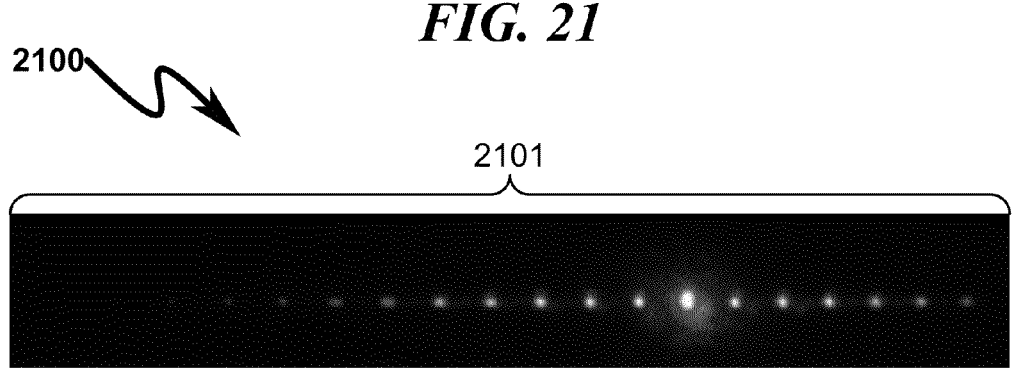
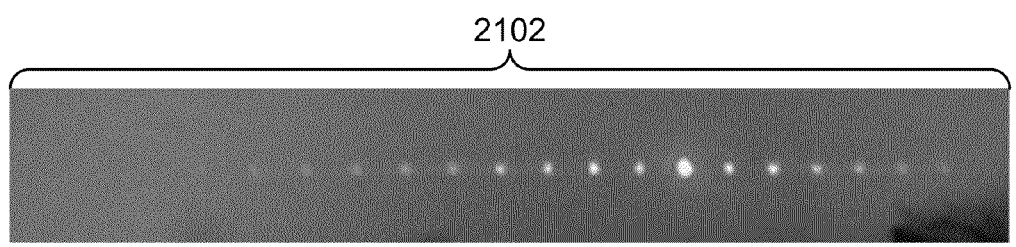
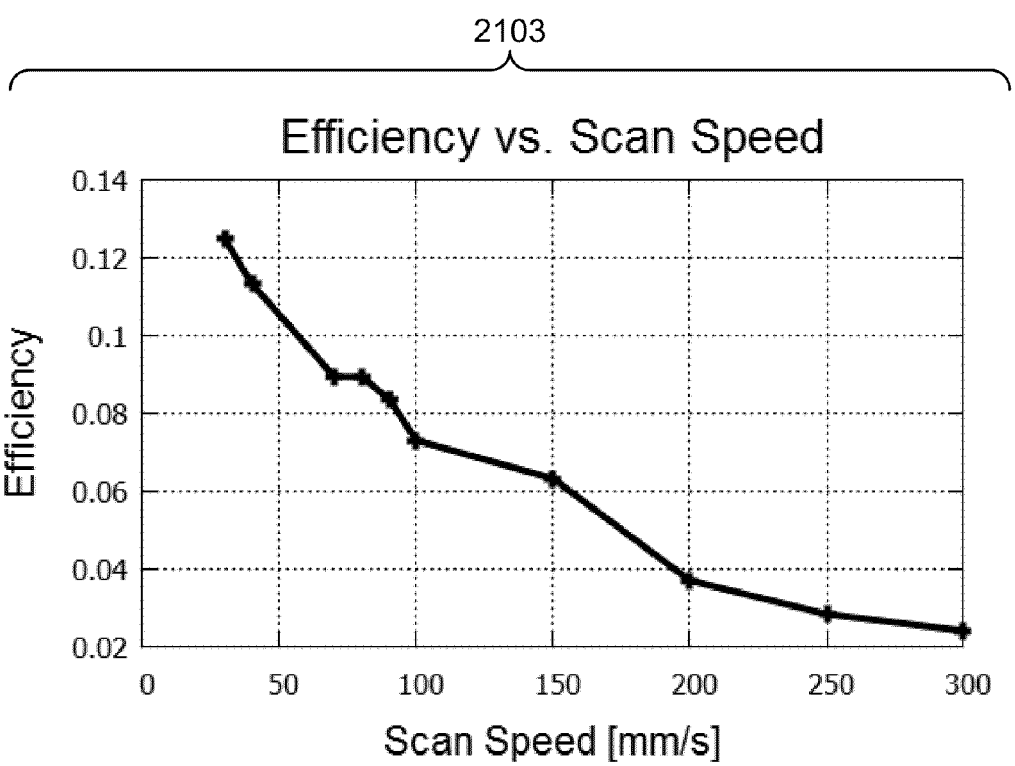

HYDROPHILICITY ALTERATION SYSTEM AND METHOD

CROSS REFERENCE TO RELATED APPLICATIONS

This application claims benefit under 35 U.S.C. §120 and incorporates by reference United States Utility Patent Application for SYSTEM FOR FORMING AND MODIFYING LENSES AND LENSES FORMED THEREBY by inventors Josef F. Bille and Stephen Q. Zhou, and filed electronically with the USPTO on Aug. 30, 2012 with Ser. No. 13/582,017.

This application claims benefit under 35 U.S.C. §120 and incorporates by reference United States Utility Patent Application for SYSTEM FOR FORMING AND MODIFYING LENSES AND LENSES FORMED THEREBY by inventors Josef F. Bille and Stephen Q. Zhou, and filed electronically with the USPTO on Mar. 4, 2010 with Ser. No. 12/717,886, now U.S. Pat. No. 8,292,952.

This application claims benefit under 35 U.S.C. §120 and incorporates by reference United States Utility Patent Application for SYSTEM FOR FORMING AND MODIFYING LENSES AND LENSES FORMED THEREBY by inventors Josef F. Billie and Stephen Q. Zhou, and filed electronically with the USPTO on Mar. 4, 2010 with Ser. No. 12/717,866, now U.S. Pat. No. 8,646,916.

This application claims benefit under 35 U.S.C. §120 and incorporates by reference PCT Patent Application for SYSTEM FOR FORMING AND MODIFYING LENSES AND LENSES FORMED THEREBY by inventors Josef F. Bille and Stephen Q. Zhou, and filed electronically with the USPTO on Mar. 4, 2010 with Ser. No. PCT/US10/26280.

This application claims benefit under 35 U.S.C. §120 and incorporates by reference PCT Patent Application for SYSTEM FOR FORMING AND MODIFYING LENSES AND LENSES FORMED THEREBY by inventors Josef F. Bille and Stephen Q. Zhou, and filed electronically with the USPTO on Mar. 4, 2010 with Ser. No. PCT/US10/26281.

This application claims benefit under 35 U.S.C. §119 and incorporates by reference United States Provisional Patent Application for HYDROPHILICITY ALTERATION SYSTEM AND METHOD by inventors Ruth (nmn) Sahler, Stephen Q. Zhou, and Josef F. Bille, filed electronically with the USPTO on Nov. 14, 2012, with Ser. No. 61/726,383, EFS ID 14230078, confirmation number 5116.

PARTIAL WAIVER OF COPYRIGHT

All of the material in this patent application is subject to copyright protection under the copyright laws of the United States and of other countries. As of the first effective filing date of the present application, this material is protected as unpublished material.

However, permission to copy this material is hereby granted to the extent that the copyright owner has no objection to the facsimile reproduction by anyone of the patent documentation or patent disclosure, as it appears in the United States Patent and Trademark Office patent file or records, but otherwise reserves all copyright rights whatsoever.

STATEMENT REGARDING FEDERALLY SPONSORED RESEARCH OR DEVELOPMENT

Not Applicable

REFERENCE TO A MICROFICHE APPENDIX

Not Applicable

FIELD OF THE INVENTION

The present invention relates to the modification of the hydrophilicity of a material. The hydrophilicity of the material is changed by exposing the material to targeted laser pulses. The laser pulses are absorbed and alter chemical bonds of the molecules within the material. The material (if hydrophobic) then either absorbs water because of the altered molecular structure or rejects water (if the material is hydrophilic). By way of example only, the present invention teaches a laser system and a method for modifying the hydrophilicity of an optical lens in a predetermined region inside the lens bulk body with or without a hydrophilicity change on the lens surfaces. The material used in the experiments described herein as applied to the present invention is a polymeric acrylic lens material (PLM) but this material selection is exemplary and should not be treated as a limitation of the present invention.

PRIOR ART AND BACKGROUND OF THE INVENTION

Background (0100)-(0400)

Conventionally, intraocular lenses are manufactured using cutting or molding techniques to fabricate polymer-based lenses which may need a tumbling step to acquire optical grade quality. Optical lenses can be surface modified by physical and chemical methods.

Physical methods include, but are not limited to plasma, corona discharge, and microwave processes. This treatment can change the hydrophilicity of the lens surface. For example, U.S. Pat. No. 5,260,093 issued on Nov. 9, 1993 to Ihab Kamel and David B. Soll for METHOD OF MAKING BIOCOMPATIBLE, SURFACE MODIFIED MATERIALS disclosed a method for permanently modifying the surface of a substrate material by radio frequency plasma. One of the substrates in disclosed in this patent is an intraocular lens.

Chemical modification of optical lenses is also well known. The chemical modification of optical lenses can change the chemical composition on the surface, thus this not only changes the hydrophilicity of the lens surface, but also the physical and chemical properties of the surface as well. For example, U.S. Pat. No. 6,011,082 issued on Jan. 4, 2000 to Yading Wang, Robert van Boxtel, and Stephen Q. Zhou for PROCESS FOR THE MODIFICATION OF ELASTOMERS WITH SURFACE INTERPRETING POLYMER NETWORKS AND ELASTOMERS FORMED THEREFROM disclosed a chemical modification method which allows a polymeric silicone intraocular lens to be chemically modified into a hydrophilic surface by heparin as well as other hydrophilic agents.

However, the above prior art methods can only be used to treat the lens surfaces. They cannot be used to modify the hydrophilicity of the lens bulk body below the surface.

In other words, they cannot be used to treat a predetermined region inside a lens material.

In contrast, recent laser technology has made it possible to selectively target a predetermined region inside a material, including optical lens materials without changing the lens surface. For example, United States Patent Application Publication US2002/0117624A for PLASTIC OBJECT published on Aug. 29, 2002 having inventors Shigeru Katayama and Mika Horiike disclosed a general method using a laser to fabricate a plastic object which has been structurally modified in one part of its internal body by a laser light of ultrashort pulse duration of $10^{-12}$ second or shorter. Examples of internal structures created using this prior art technique are generally illustrated in FIG. 1 (0100) and FIG. 2 (0200).

A more recent application in United States Patent Application Publication US2008/0001320A1 for OPTICAL MATERIAL AND METHOD FOR MODIFYING THE REFRACTIVE INDEX published on Jan. 3, 2008 having inventors Wayne H. Knox, Li Ding, Jay Friedrich Kunzler, and Dharmendra M. Jani disclosed a method for modifying the refractive index of an optical polymeric material comprising irradiating the selected region by femtosecond laser pulses (using a system configuration as generally illustrated in FIG. 3 (0300)) resulting in the formation of refractive optical structure of the laser treated region which is characterized by a positive change in refractive index. This patent application publication also disclosed calculating the refractive index change (tn) as positive in the range of 0.03 to 0.06. This prior art teaches that if the selected treatment region is a convex-plano shape, it will create a positive lens while if the treated region is a biconcave shape, then it will be a negative lens. This is described in drawings of the US2008/0001320A1 patent application publication and is reproduced as FIG. 4 (0400) herein.

The prior art does not address the modification of the hydrophilicity of an internal region of a material.

DEFICIENCIES IN THE PRIOR ART

While the prior art as detailed above can theoretically be used to form optical lenses, it suffers from the following deficiencies:
- Prior art limits the lens formed within the lens material to 2.65 diopter in change for a lens with a 200 micron thickness and 6 mm diameter while the present invention creates a up to a 20 diopter lens with the same lens diameter.
- Prior art requires several hours to create a 2.65 diopter lens while the present invention would produce the same lens in a few minutes. Prior art paper publication show a shaping speed of 0.4 um/s for the high refractive index change. The following parameters have been used: a spot size of 1 um in XY and 2.5 um in Z and a convex lens diameter with 6 mm and a lens depth of 200 um. Source: Li Ding, Richard Blackwell, Jay F. Künzler and Wayne H. Knox "LARGE REFRACTIVE INDEX CHANGE IN SILICONE-BASED AND NON-SILICONE-BASED HYDROGEL POLYMERS INDUCED BY FEMTOSECOND LASER MICRO-MACHINING".
- Prior art can only produce a positive diopter change assuming a convex lens while the instant invention can only produce a negative diopter change using a convex lens.
- Prior art is limited to one lens within the material while the invention can stack multiple lens to increase the diopter change or alter asphericity, toricity or other lens properties.
- Prior art discloses no relationship between hydrophilicity change and UV absorption while the instant invention relies on UV absorption to effect the change in hydrophilicity.
- Prior art makes no change in hydrophilicity and the instant invention relies upon a change in hydrophilicity to effect the change in the material.

To date the prior art has not fully addressed these deficiencies.

OBJECTIVES OF THE INVENTION

Accordingly, the objectives of the present invention are (among others) to circumvent the deficiencies in the prior art and affect the following objectives:
(1) provide for a system and method that permits the modification of the hydrophilicity of the interior of a material with or without a change in the hydrophilicity of the surface of the material;
(2) provide for a system and method that alters the hydrophilicity of an entire predetermined three dimensional region within a polymeric material;
(3) provide a system and method of manufacturing an optical lens; and
(4) provide a system and method for altering the hydrophilicity of a predetermined internal region of an implanted intraocular lens thus altering the refractive properties of the implanted intraocular lens according to the individual patient's need for a desirable vision outcome.

While these objectives should not be understood to limit the teachings of the present invention, in general these objectives are achieved in part or in whole by the disclosed invention that is discussed in the following sections. One skilled in the art will no doubt be able to select aspects of the present invention as disclosed to affect any combination of the objectives described above.

BRIEF SUMMARY OF THE INVENTION

The present invention pertains to a system, method, and product-by-process wherein a pulsed laser system is used to modify the hydrophilicity of a polymeric material (the material used in all referenced experiments was a polymeric acrylic polymer ("PLM") however that material is used as an example and is not limitation of the present invention scope). The change in hydrophilicity may be used to:
form an optical lens having predetermined refractive properties;
create hydrophilic areas in an otherwise hydrophobic material; or
create hydrophilic areas in an otherwise hydrophilic material.

The present invention is particularly, but not exclusively, useful as describing the procedure to create a very thin, multi-layered, micro-structured customized intraocular lens inside a PLM. This technique could be used, but is not limited to modifications of an existing lens which is currently implanted within a human eye. The modifications can adjust diopter and/or add additional properties like toricity and asphericity. The instant invention is capable of creating new lenses which are thinner than existing products and can be injected through a small incision. In particular, a system and method for the shaping of a refractive index within lenses based on the modification of the hydrophilicity of the material is disclosed.

The present invention describes a laser system and a method for modifying the hydrophilicity for a predetermined internal region of PLM which may be used as an optical lens. The present invention can be utilized to modify the optical properties of an optical lens by adding (or reducing) its optical power, or altering its asphericity, multifocalilty, toricity and other optical properties. Typical application for this invention may include correcting the post-operational residual refractive error of an intraocular lens which has already been implanted in a patient's eye.

In spite of the best effort by surgeons, residual refractive error is inevitable in many cases due to deviations in lens power selection, patient's history of past eye surgeries such as LASIK procedure, surgery induced astigmatism, and progressive change in vision of a patient. Currently, surgeons use LASIK, a procedure to reshape a patient's cornea by destroying a portion of the cornea by laser beams, to correct residual refractive error after cataract surgery. Alternatively, patients may need to wear eye glasses to correct post-operational refractive errors. The present invention promotes a scenario in which these optical non-idealities may be corrected in situ after the cataract surgery is completed.

Within the scope of the present invention a customized intraocular lens may be manufactured using either all optical processes or a combination of the traditional manufacturing in combination with optical processes to reduce the lens thickness and the needed incision size. The optical process is typically employed by using a femtosecond laser with pulse energies of 0.17 to 500 nanjoules and a megahertz repetition rate of 1 to 100.

The focus spot of the laser beam is moved inside the lens material to create a pattern of changes in the material, creating a three dimensional lens. Different patterns will provide different lens properties, for example a toric or aspheric lenses.

BRIEF DESCRIPTION OF THE DRAWINGS

For a fuller understanding of the advantages provided by the invention, reference should be made to the following detailed description together with the accompanying drawings wherein:

FIG. 8 illustrates a comparison of prior art lens configurations using a convex lens for optical convergence and present invention a lens configurations using a concave lens for optical convergence;

FIG. 9 illustrates the use of the present invention to modify the hydrophilicity of a PLM in single and multiple layer configurations;

FIG. 10 illustrates an exemplary convex/biconvex lens structure as taught by the present invention;

FIG. 12 illustrates exemplary phase wrapping lens structures that may be formed using the teachings of the present invention;

FIG. 13 illustrates the refractive index patterns associated with exemplary phase wrapping lens structures that may be formed using the teachings of the present invention;

FIG. 17 illustrates an exemplary experimental sample PLM structure as taught by the present invention;

FIG. 21 illustrates an exemplary experimental refractive index pattern as taught by the present invention;

DESCRIPTION OF THE PRESENTLY PREFERRED EXEMPLARY EMBODIMENTS

Figure 1:
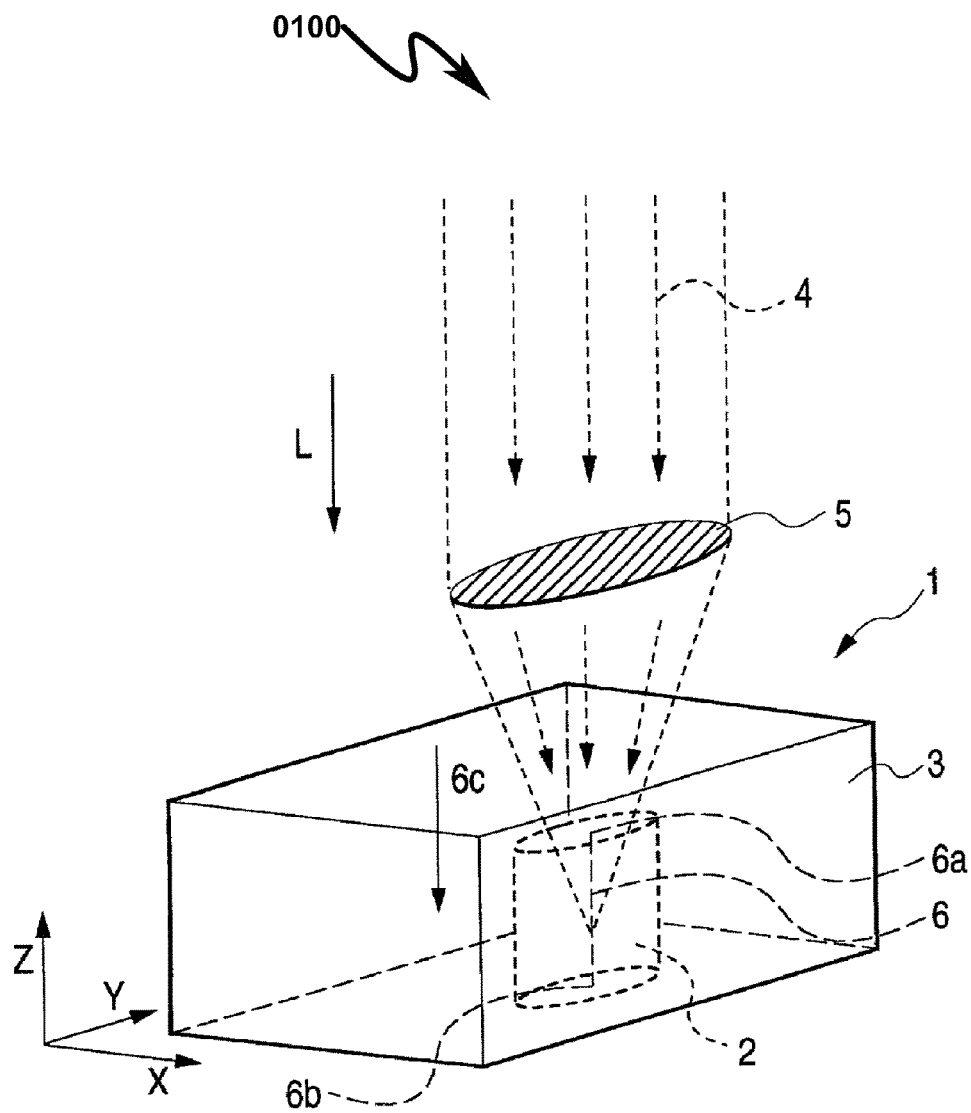
FIG. 1 illustrates a prior art methodology of internal plastic modification as taught by United States Patent Application Publication US2002/0117624A.
Figure 2:
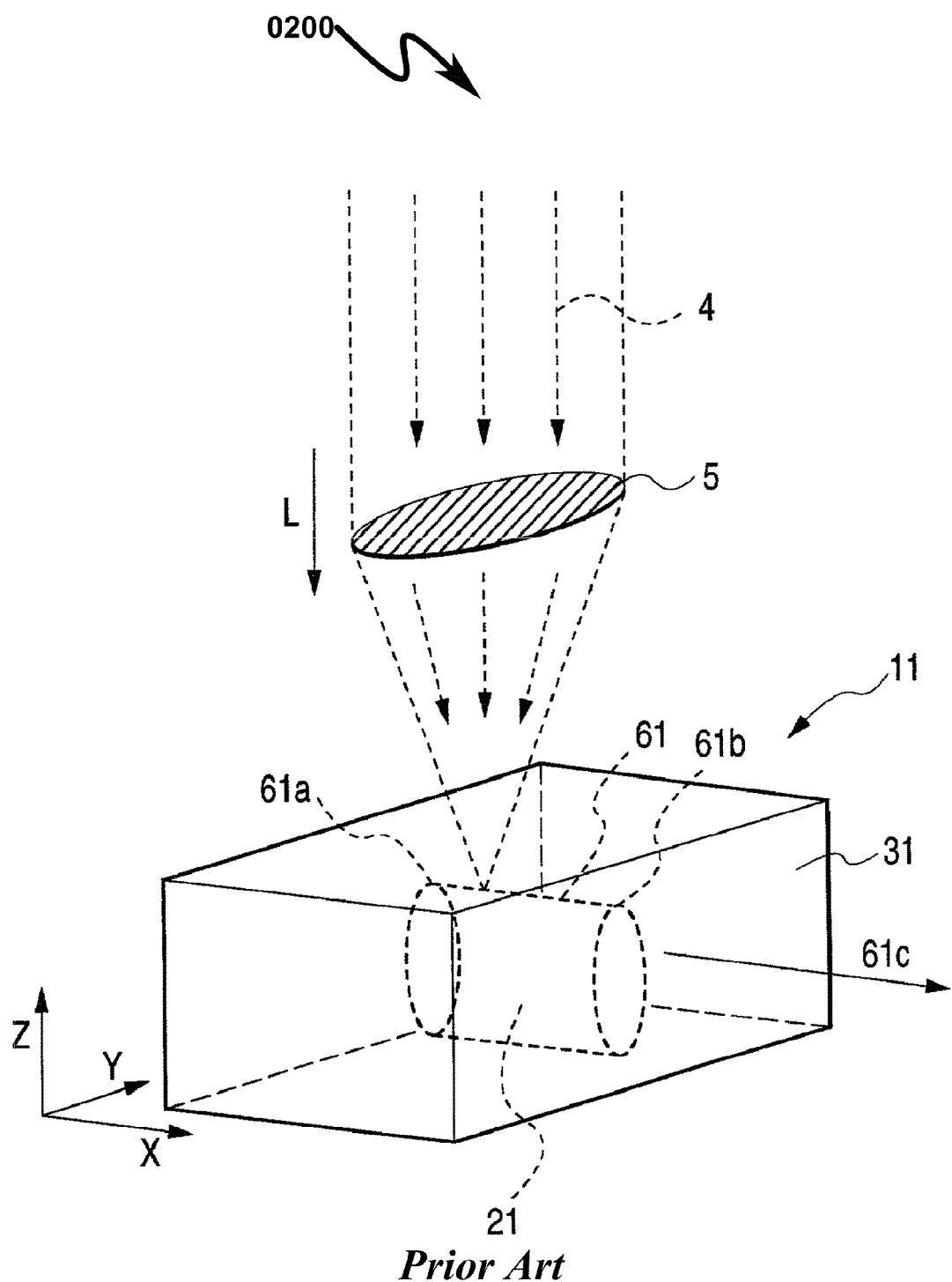
FIG. 2 illustrates a prior art methodology of internal plastic modification as taught by United States Patent Application Publication US2002/0117624A.
Figure 3:
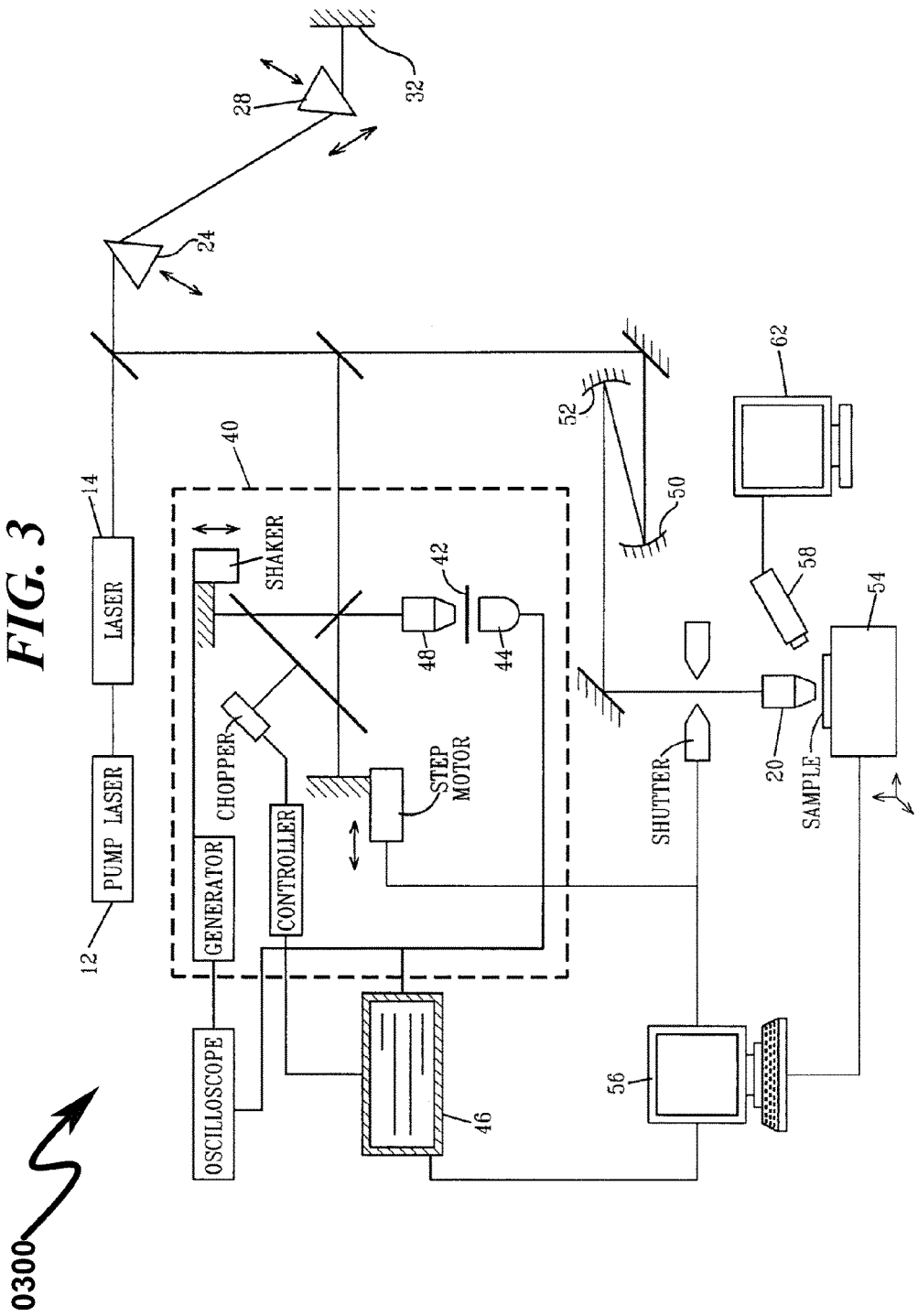
FIG. 3 illustrates a prior art system for lens formation as taught by United States Patent Application Publication US2008/0001320A1.
Figure 4:
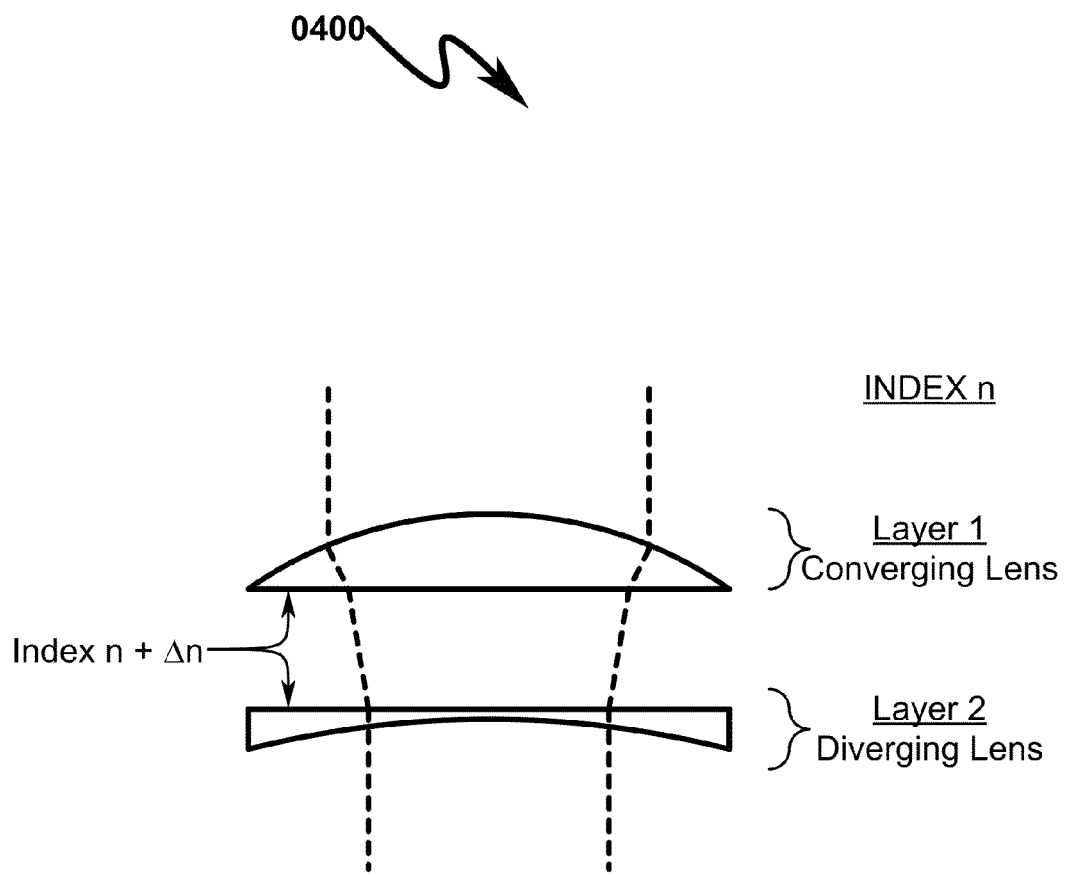
FIG. 4 illustrates a prior art lens form as taught by United States Patent Application Publication US2008/0001320A1.

While this invention is susceptible of embodiment in many different forms, there is shown in the drawings and will herein be described in detailed preferred embodiment of the invention with the understanding that the present disclosure is to be considered as an exemplification of the principles of the invention and is not intended to limit the broad aspect of the invention to the embodiment illustrated.

The numerous innovative teachings of the present application will be described with particular reference to the presently preferred embodiment, wherein these innovative teachings are advantageously applied to the particular problems of a HYDROPHILICITY ALTERATION SYSTEM AND METHOD. However, it should be understood that this embodiment is only one example of the many advantageous uses of the innovative teachings herein. In general, statements made in the specification of the present application do not necessarily limit any of the various claimed inventions. Moreover, some statements may apply to some inventive features but not to others.

Hydrophilicity not Limitive

Within the context of the present invention the term "hydrophilicity" will be defined as the characteristic of a material to "have a strong affinity for water or tend to dissolve in, mix with, or be wetted by water."

Material (PLM) not Limitive

The present invention may incorporate a wide range of materials, including the PLM but not limited to the PLM, within the scope of anticipated embodiments, many of which may be application specific. PLM may in many preferred embodiments incorporate the use of an ultraviolet (UV) (generally 300-400 nm wavelength) absorbing material to augment the absorption of pulsed laser energy by the PLM and thus affect a change in hydrophilicity of the PLM. PLM as used herein should not be constrained as limiting its use to materials that form optical lenses. Specifically, the term "polymeric material (PM)" may be used herein to denote applications of the invention system/method/product that are not necessarily limited to the production of optical lenses. Thus, "PM" may cover a broader application of the invention concepts than "PLM", although the materials may be identical. Therefore, the term "polymeric lens material (PLM)", "polymeric material (PM)" and their equivalents should be given the broadest possible meaning within this context.

UV Absorbers not Limitive

The PLM may incorporate a number of chemicals which may enhance the UV absorption of the PLM and thus enhance the change in the PLM's hydrophilicity when irradiated with pulsed laser radiation. The present invention makes no limitation on the types and quantities of chemicals used to affect this behavior, and the recitation of these chemicals within this document is only exemplary of those anticipated.

Laser Radiation Not Limitive

The present invention may incorporate a wide variety of laser radiation to affect changes in hydrophilicity within the PLM described herein to form a lens. Therefore, the term "laser radiation" and its equivalents should be given the broadest possible meaning within this context, and not limited to near infrared light laser radiation.

Laser Source Not Limitive

The present invention may incorporate a wide variety of laser radiation sources provide the required pulsed laser radiation used within the disclosed invention. Within this context, the term "laser source" may also incorporate an Acousto-Optic Modulator (AOM) (also called a Bragg cell) that uses the acousto-optic effect to diffract and shift the frequency of laser light generated using sound waves (usually at radio-frequency). Within this context, the "laser source" may be globally defined as comprising a laser radiation source and optionally an AOM, whether or not the AOM is physically incorporated into the laser radiation source hardware. Therefore, the term "laser source" and its equivalents should be given the broadest possible meaning within this context.

Acousto-Optic Modulator (AOM) not Limitive

Various invention embodiments may make use of an Acousto-Optic Modulator (AOM) to act as a switch to enable/disable or moderate the quantity of laser radiation pulse stream as directed to the laser scanner within the context of the invention. Within this context the AOM may incorporate "greyscale" modulation wherein the switching function serves to switch a portion of the laser radiation pulse train to the laser scanner and therefore permit reductions in effective laser power as applied to the targeted PLM to which the hydrophilicity is to be modified.

Thus, the utilization of "greyscale AOM" components to modulate laser radiation intensity is specifically anticipated within the scope of the invention.

The AOM as depicted in the present invention is used as a shutter and as variable attenuator and as such could therefore be replaced with another equivalent component which simulates the same functionality as described above.

Laser Scanner Not Limitive

The use of a laser scanner within the preferred invention embodiments described herein may incorporate many different varieties of scanner, including but not limited to flying spot scanners (generally vector-based modes) and raster scanners (generally raster-based modes). The scanner is used to distribute the laser pulse to the correct location within the objectives field size. The present invention makes no limitation on the type of laser scanner that may be used in this context.

Microscope Objective not Limitive

References herein to a "microscope objective" may equivalently utilize a "microscope objective or other focusing device" to achieve these functions. Thus, the term "microscope objective" should be given its broadest possible interpretation within this application context.

Patient not Limitive

The present invention may be applied to situations where a lens placed in a living creature is modified in situ to correct/modify the refractive properties of the lens without removal from the eye of the creature. Within this context, the term "patient" shall be broadly construed and should not be limited to application only on human beings.

Lens Form not Limitive

The present invention may incorporate a wide variety of lenses formed to affect optical light bending and thus the construction of an overall lens formation. While exemplary embodiments of the present invention are described herein as being used to construct convex, biconvex, concave, biconcave, and plano lens structures, these structures are only exemplary of a plethora of lens forms that may be constructed with the present invention. Therefore, the term "lens formation" and its equivalents should be given the broadest possible meaning within this context.

Two-Dimensional not Limitive

The present invention may incorporate the use of two-dimensional pattern structures within the PLM to form diffraction gratings and other thin planar structures which while technically three-dimensional, will be termed herein as two-dimensional. While no modification of the PLM hydrophilicity can occur strictly in a zero-thickness plane, the term two-dimensional will refer to the creation of structures which occur within the PLM that do not require Z-axis focus repositioning across the X-Y plane perpendicular to the optical axis. Thus, a two-dimensional modification of the PLM refractive index could occur along a non-planar boundary that comprises a singular Z-axis focal distance for the laser pulses. Therefore, the term "two-dimensional" and its equivalents should be given the broadest possible meaning within this context.

Three-Dimensional not Limitive

The present invention may incorporate the use of three-dimensional pattern structures within the PLM to form complex optical structures. These three-dimensional pattern structures and their associated volumes may comprise multiple layers having interstitial PLM having a hydrophilicity that has not been modified by irradiation with laser pulses. Thus, a three-dimensional structure may incorporate non-modified areas having unmodified or slightly modified layer, or multiple layers comprising differing levels of hydrophilicity and resulting refractive index changes. Therefore, the term "three-dimensional" and its equivalents should be given the broadest possible meaning within this context.

Intraocular Lens not Limitive

The present invention may be advantageously applied to the construction of dynamically adjustable optical lenses incorporating a wide range of materials. The mechanisms of incorporation of a wide variety of materials within the optical lens are not limited by the present invention. Therefore, the term "intraocular lens" and "optical lens (which would include contact lenses)" and its equivalent construction embodiments should be given the broadest possible meaning within this context.

General System Description

The present invention may be generally described as utilizing a laser system which consists of a femtosecond laser source, an AOM, a scanner, and an objective which delivers the laser pulses into the predetermined region. The laser source preferably has a pulse duration of approximately 350 fs or shorter, a wavelength in the range of 690 to 1000 nm, and a repetition rate of between approximately 0.1 to 100 MHz. The pulse energy is typically in the range of 0.17 to 500 nanojoules. Those who are skilled in the art understand that these laser parameters can be adjusted and rebalanced to be outside above-specified range but still be able to achieve the same level of energy delivered to the targeted regions of the lens material. For example, a tunable laser unit, such as Ti:Saphphire oscillator (Mai Tai By Newport, Irvine, Calif.) can provide a variable wavelength in the range of approximately 690-1040 nm, a pulse width of as low as 70 fs, and a source power up to 2.9 W.

Generalized Hydrophilicity Modification System (0500)

Figure 5:
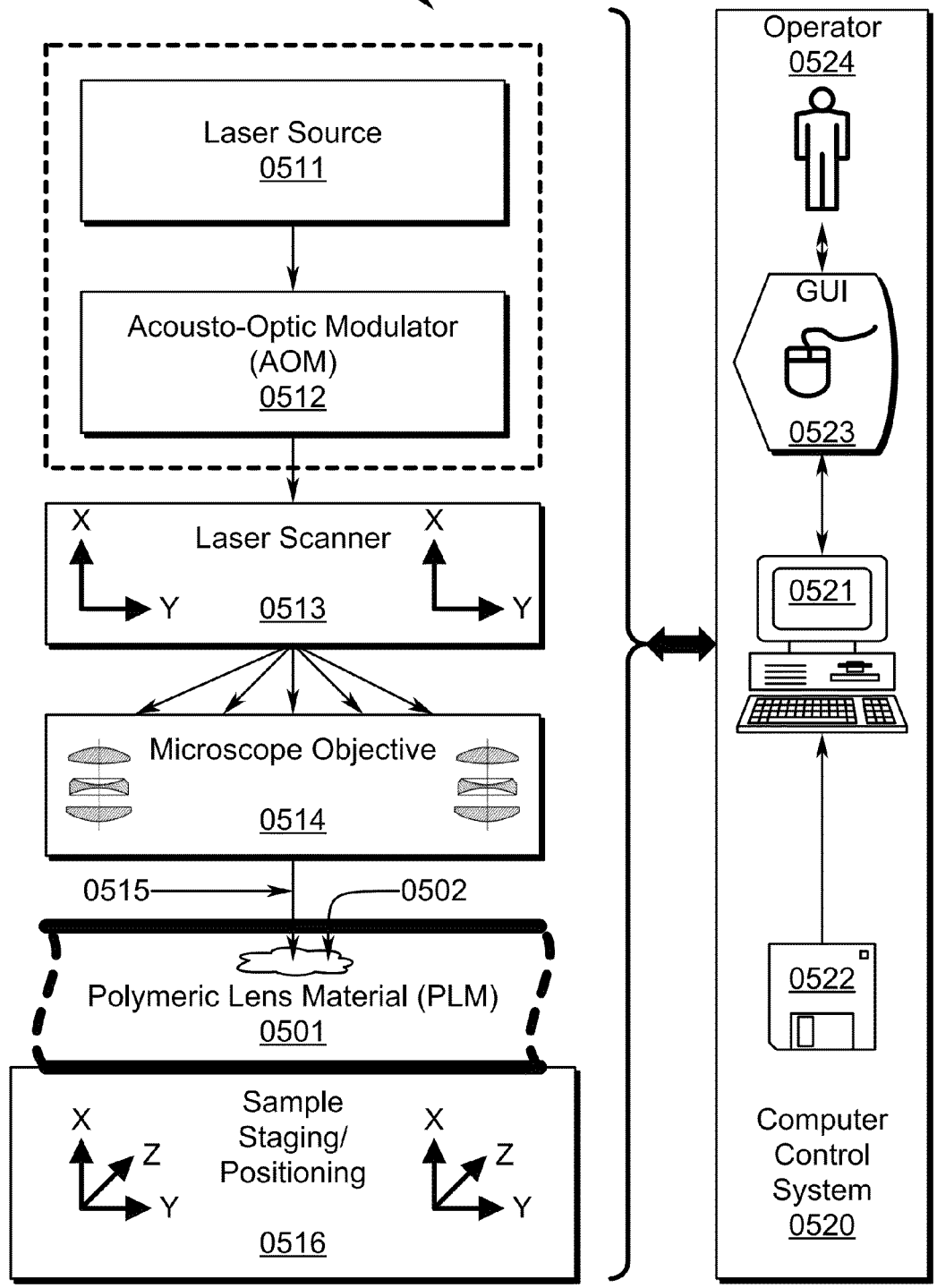
FIG. 5 illustrates an exemplary system block diagram depicting a preferred exemplary system embodiment of the present invention.

A preferred exemplary system embodiment of the present invention is generally illustrated in FIG. 5 (0500), wherein a material (0501) is irradiated (0515) to produce a change in hydrophilicity within a selected region (0502) within the PLM (0501). This system (0500) generally incorporates a laser source (0511) that is configured to generate pulsed laser radiation which may be controlled/moderated/modulated/switched by an acousto-optic modulator (AOM) (0512) to produce a predetermined laser pulse train having specified energy and pulse timing characteristics. In some invention embodiments the laser source (0511) and AOM (0512) may be integrated into a single laser source module. The pulsed laser radiation generated by the laser source (0511)/AOM (0512) is then transmitted to a laser scanner (0513) that is configured to distribute the laser pulses in an X-Y plane across an input area of a microscope objective (0514).

The microscope objective (0514) incorporates a numerical aperture configured to accept the distributed pulsed laser radiation and produce a focused laser radiation output (0515). This focuses laser radiation output (0515) is then transmitted by the microscope objective (0514) to a polymeric lens material (PLM) (0501) region (0502) in which the hydrophilicity of the PLM (0501) is to be changed. The position of the hydrophilic-modified PLM region (0502) may be defined by the laser scanner (0513) as well as a sample staging/positioning system (0516) that mechanically positions the PLM (0501) to allow the focused laser pulses (0515) to be properly localized within the desired interior region (0502) of the PLM (0501).

This system may optimally operate under control of a computer control system (0520) incorporating a computer (0521) executing software read from a computer readable medium (0522) and providing a graphical user interface (GUI) (0523) from which an operator (0524) may direct the overall operation of the hydrophilicity change (0502) within the PLM (0501).

System/Method Application Context Overview (0600)

Figure 6:
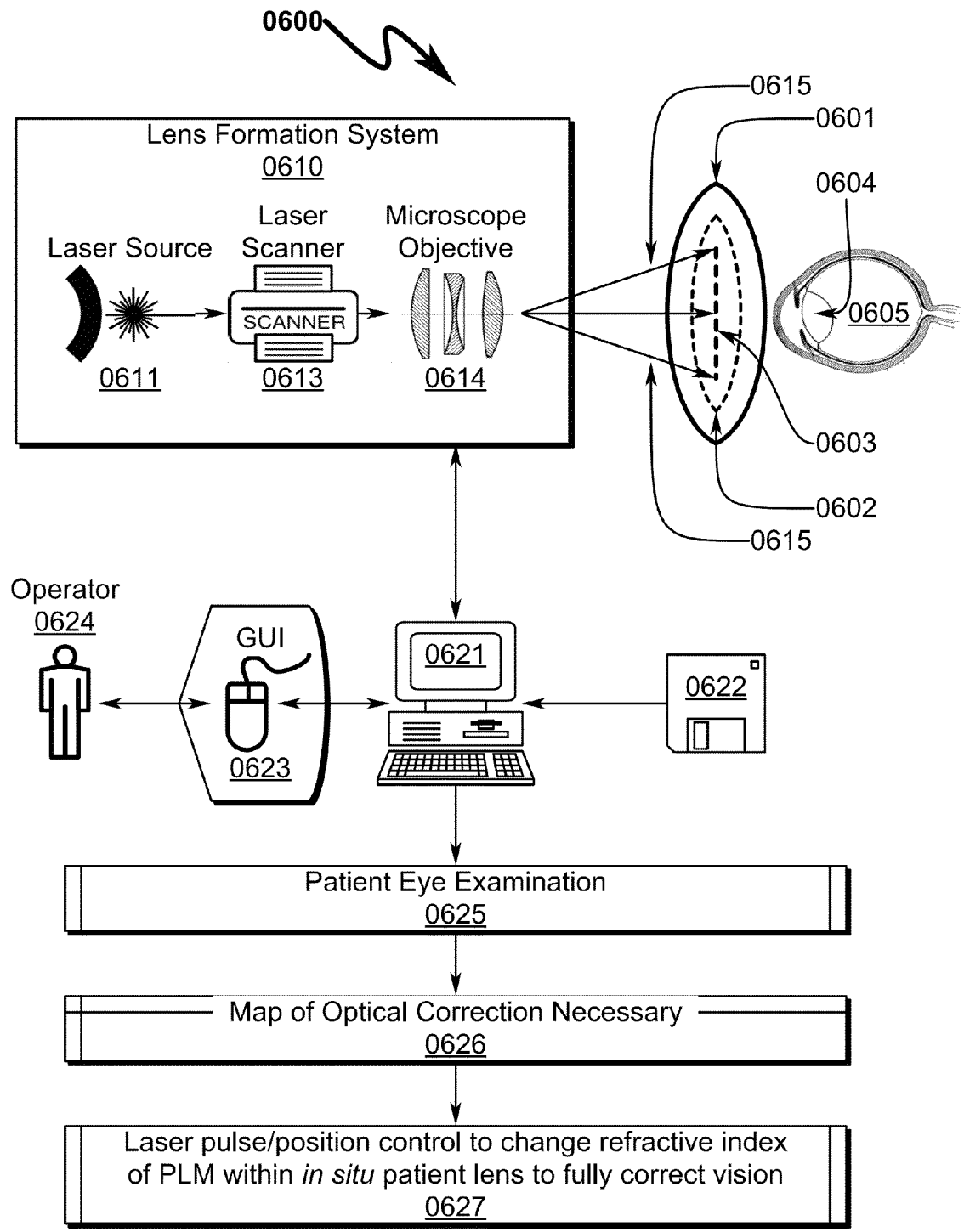
FIG. 6 illustrates an exemplary system block diagram of a preferred exemplary system embodiment of the present invention depicting a typical invention application setup context.

A typical application context for the present invention is generally illustrated in FIG. 6 (0600), wherein the present invention is embodied in a hydrophilicity alteration system (0610) used to configure patient lenses. This hydrophilicity alteration system (0610) typically comprises a laser source (0611) that generates a pulsed laser output that is then distributed in an X-Y plane using a laser scanner (0613) and then focused using a microscope objective (0614) (or other focusing apparatus). This distributed and focused pulsed laser radiation (0615) is transmitted within a lens structure (0601) having some portion of which that is constructed of material (PLM) (0602). This PLM (0602) is irradiated in a two or three-dimensional pattern (0603) within the PLM structure (0602) to modify the hydrophilicity. Any modifications in hydrophilicity will create some change in the refractive index of the internal region of the PLM (0603). This change in refractive index generated by the focused laser pulses (0614) causes the two or three-dimensional pattern (0603) to form an optical lens function within the overall lens structure (0601).

In conjunction with this general system/method configuration, the lens structure (0601) may be incorporated (0604) within a human eye (0605) and the PLM (0602) modified in situ after the lens structure (0601) has been surgically implanted within the eye of a patient as generally illustrated in the diagram.

The described hydrophilicity alteration system (0610) is typically operated under control of a computer system (0621) executing instructions from a computer readable medium (0622). This computerized control (0621) optimally incorporates a graphical user interface (0623) permitting the system operator (0624) to interface with the overall system and direct its operation. With respect to the above-mentioned in situ lens formation application, the control software (0622) may incorporate software implementing methods to perform an automated patient eye examination to determine the non-idealities in the patient's vision (0625), from which a map of optical corrections (0626) necessary to improve the patient's vision is generated, followed by automated laser pulse/position control procedures to change in situ the refractive index of PLM within the patient lens to fully correct the patient vision (0627).

System/Method Application Context Detail (0700)

Figure 7:
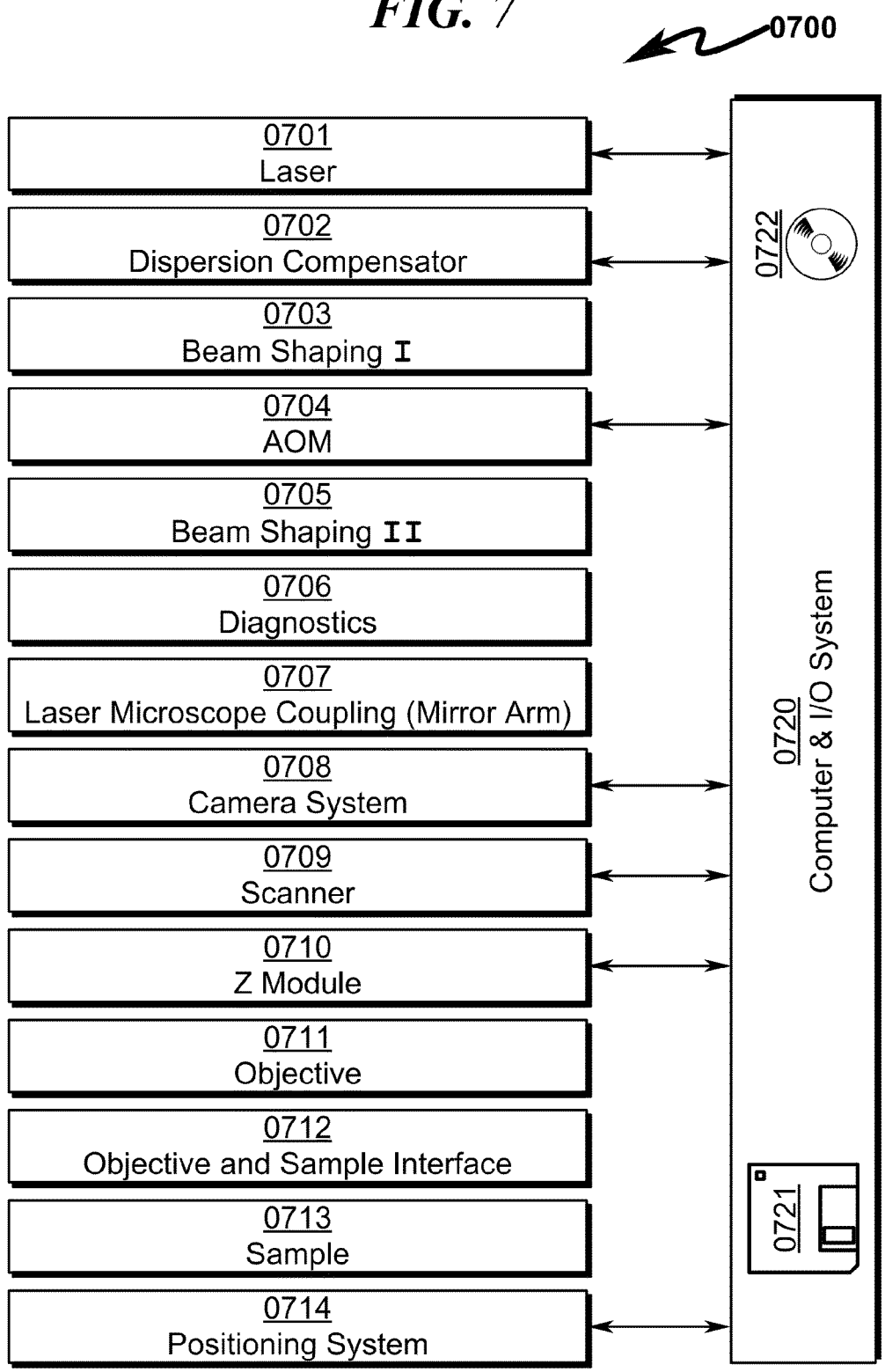
FIG. 7 illustrates a detail system block diagram illustrating system components that may be used to implement some preferred invention embodiments.

A more detailed system configuration of a preferred invention application context is provided in FIG. 7 (0700), wherein a computer system (0720) operating under control of software read from a computer readable media (0721, 0722) is used to control and supervise the overall lens fabrication process. Within this application context, the following components generally comprise the system:

The laser source (0701) with a wavelength suitable to treat the desired material and an energy-per-pulse sufficient to change the refractive index of the target area provided by the used objective (0710).

The Dispersion Compensator (0702) is used to pre-compensation the beam to allow a pulse width around 100 fs. Without the feature the pulse width at the target would be larger because the pulse width gets longer when passing through an optical media like a lens. With a longer pulse with more heat would occur on the treatment area, making the process a little more imprecise and the treatment time a little longer. This feature therefore is optional but part of the RIS optimization.

The Beam Shaping 1 (0703) unit can be used to modify the laser beam diameter to fit the AOM specifications. This also allows the exchange of the laser source without additional modifications after the beam shaping 1 unit.

The AOM (0704) is used to modulate the number of pulses and the energy per pulse which will be directed to the treatment area. Depending on the received signal (normally 0 to 5V) the energy will be distributed to the 0 or the $1^{st}$ order of the AOM. Those orders are two different beams, with an angle between them, coming out from the AOM. The $1^{st}$ order beam is normally the one going to the target area and the 0 order beam is stopped directly after the AOM. The receiving signal from the AOM driver is maximum (eg 5V) the maximum energy per pulse is in the $1^{st}$ order beam, when the driver signal is at the minimum the $1^{st}$ order beam will have 0% energy and everything will be delivered to the 0 order.

Beam Shaping 2, after the beam has passed through the AOM additional beam shaping is required to fit the system. For example the beam diameter has to be enlarged to fit the used objective (0710), to allow the use of the numerical aperture of the objective.

A Diagnostics (0705) system is used to measure the wavelength, energy per pulse and the pulse width of the laser beam. This feature in included to allow the safe and repeatable use of the system. If one of the variables is not performing as planned the system will shut down and Laser Microscope Coupling (Mirror Arm) (0706) is used to redirect the laser beam into the laser microscope head. Depending on the system setup and laser orientation it can contain between one and multiple mirrors to redirect the laser beam to the needed position.

The Camera System (0707) is used to position the sample towards the microscope objective. It also is used to find the correct Z location, depending on the materials curvature. Additionally the camera can be used for tracking purposes.

- The Scanner (0708) is used to distribute the laser spot on the XY plane. Different scanners can be used for this purpose. Depending on the scanner type the untreated area would still be covered but with no laser energy per pulse or only the treated areas would be covered. For this purpose the software controlling will also control the AOM because the scanner software will position the spot and the AOM will contribute the energy per pulse for that spot.
- The Z Module (0709) can be used to allow an extra focusing element in the system, this for example can be used for tracking purposes for a plane in a different Z location than the shaping plane. It also could be used to change the Z location during the shaping process.
- The Objective (0710) focuses the beam on the sample and determines the spot size. With a larger spot size a larger energy per pulse is required it therefore has to be fitted to the laser source and the required precision of the process. Additionally it provides the field size of the shaping process, if the field size of the objective is smaller than the required lens, this requires additional hardware for the lens shaping.
- The Objective and Sample Interface (0711) is depending on the application. For the lens manufacturing the space between the sample and the objective is filled with water to reduce scattering and allow an additional cooling element. For other applications different contact method with other mediums like eye gel could be used.
- The Sample (0712) can surprise of different optical mediums and could for example be a hydrophobic polymer which is placed in front of the objective. Depending on the application that sample will be directly after the Objective and Sample interface or deeper inside an additional medium combination like an eyeball.
- The Positioning System (0713) can be used to position the blocks comprising of the objective field sizes towards each other to allow the shaping of a larger structure. It can also be used to move the sample in the Z direction.

One skilled in the art will recognize that a particular invention embodiment may include any combination of the above components and may in some circumstances omit one or more of the above components in the overall system implementation.

Comparison of Prior Art/Present Invention (0800)

A comparison of the prior art and present invention methodologies for achieving optical convergence within a lens structure is generally illustrated in FIG. 8 (0800). The prior art as generally depicted in FIG. 8 (0800, 0810) makes use of convex lens formation methodologies to generate optical convergence as illustrated in this example. It is essential to note that the prior art makes no change in hydrophilicity of the lens material but simply changes the refractive index of the material. By contrast, the present invention using changes in PLM hydrophilicity as generally illustrated in FIG. 8 (0800, 0820) to generate optical convergence. While both techniques may make use of multiple lens structures, the present invention relies on negative diopter material modification (0821) to create these lens formations (all increases in hydrophilicity reduce the refractive index of the material while all the prior art makes changes in the material that create positive diopter material modification (0811).

Exemplary Application Context Overview (0900)

As generally depicted in FIG. 9 (0900), the present invention uses a femtosecond pulse laser (0911) to enable a hydrophilicity change (alteration) (0912) inside a PLM (0913). As generally depicted in FIG. 9 (0900), a three dimensional layer (0922) of hydrophilicity change (alteration) can be shaped in a PLM (0921) using a XYZ stage system. The depth of the layer is predetermined in the software. The layer could be positioned at the surface (0923) or intermediate layers (0924, 0925).

The present invention also anticipates a system configured to form optical lenses from a PLM, a method by which lenses may be formed using PLM, and the lenses formed by the method using the PLM. Any of these invention embodiments may be applied to situations in which a lens implanted in a human (or other biologic eye) may be modified and/or corrected in situ without the need for removal of the lens from the patient.

The present invention can also be used to create hydrophilic channels within a PLM. Such areas can be used to facilitate the passage of other chemical substances into our out of such materials.

Exemplary Lens Formation Structures (1000)-(1300)

Figure 11:
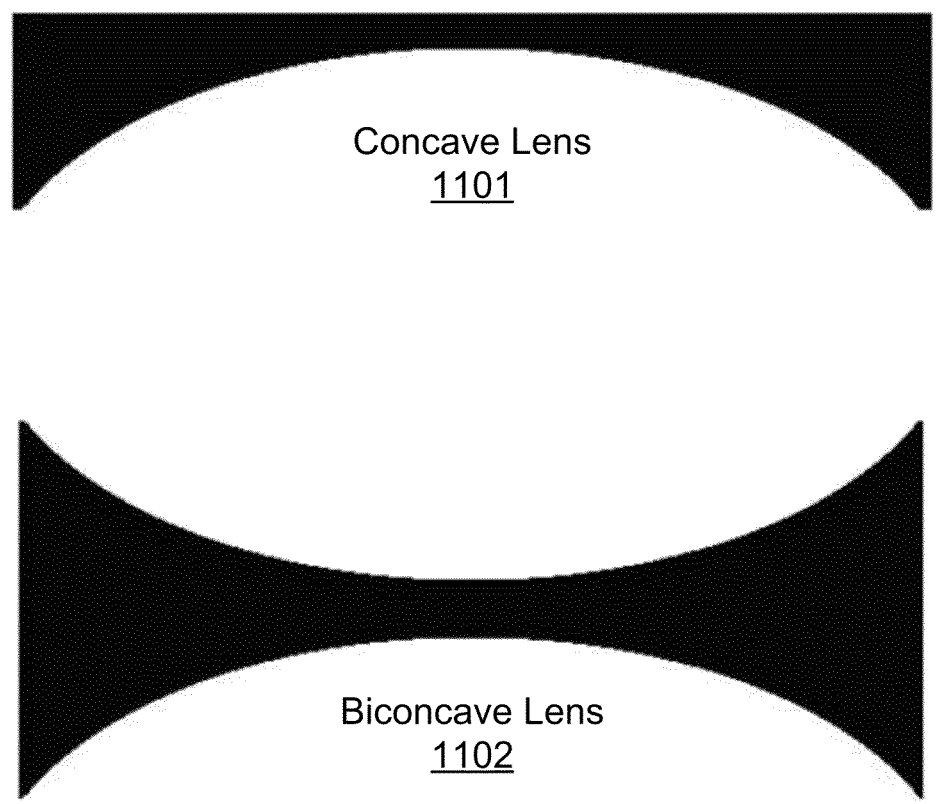
FIG. 11 illustrates an exemplary concave/biconcave lens structure as taught by the present invention.

While the present invention may in many contexts be applied to the formation of a wide variety of lens structures, several forms are preferred. These include but are not limited to convex (1001) and biconvex (1002) structures as depicted in the profiles of FIG. 10 (1000); concave (1101) and biconcave (1102) structures as depicted in the profiles of FIG. 11 (1100); and phase wrapping convex (1201) and phase wrapping concave (1202) structures as depicted in the profiles of FIG. 12 (1200). One skilled in the art will recognize that these lens structures are only exemplary of a wide variety of lenses that may be formed using the teachings of the present invention. Additionally, the layering of PLM modified structures as depicted in FIG. 9 (0900, 0921) may permit the layering of a plurality of lens structures within a single PLM.

Phase Wrapping Lens (1200,1300)

The present invention may be used to form phase wrapping lens as generally depicted in the phase wrapping convex (1201) and phase wrapping concave (1202) structures depicted in FIG. 12 (1200) and the associated exemplary refractive indexes depicted in FIG. 13 (1300). Phase wrapping lenses use the same theoretical idea as the Fresnel lens (1204). The difference in quality can be summarized in three different factors:

- the original lens curvature is preserved for the Phase Wrapping lens;
- the laser shaping technique allows the preservation of the 90 degree angle at each zone for the Phase Wrapping lens; and
- the micrometer precision to which the Phase Wrapping lens may be shaped.

In contrast, the limitations for the Fresnel lens (1205) are generally derived from the manufacturing process in which it is created. The main manufacturing difference for a Phase Wrapping Lens and a Fresnel lens are shown in image 1206.

Refractive Index Gradient Lens (1300)

The present invention may be used to form a refractive index gradient lens as generally depicted in FIG. 13 (1300).

The information of the lens curvature is in this concept is stored in a single layer. The grayscale values are used to represent the energy per pulse. Therefore 256 variations of the power between 0% and 100% are possible and allow the precise shaping of a single layered lens. The top view of a refractive index lens (1301) shows the different zones of an original convex phase wrapping lens. Each original discussed lens type data information can be compressed to one single layer. The side view of the refractive index gradient lens (1302) shows the energy distribution at each spot for one horizontal slice through the center of the lens.

The modulation of the pulse energy can be accomplished using the AOM or an automatic variable attenuator.

PLM Method (1400)

Figure 14:
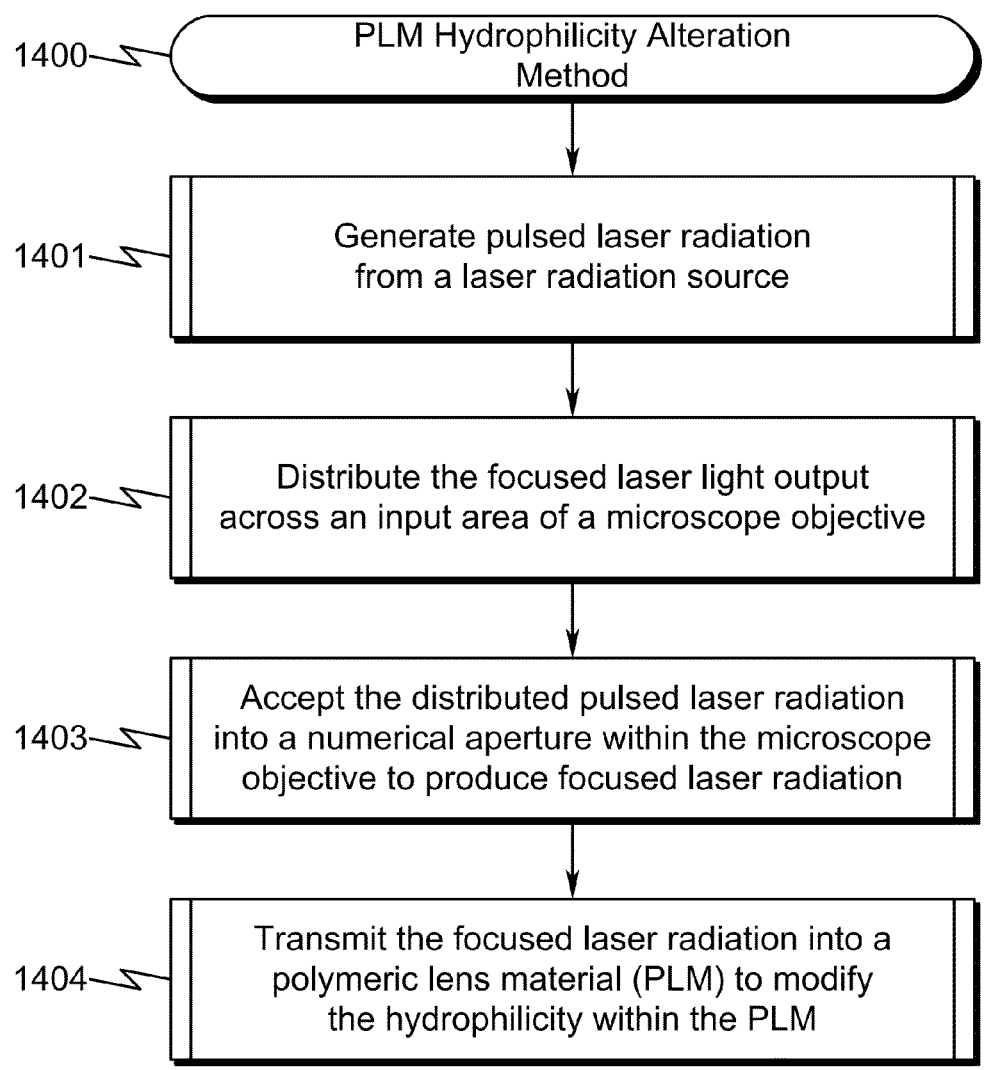
FIG. 14 illustrates an exemplary PLM hydrophilicity alteration method flowchart used in some preferred embodiments of the present invention.

The present invention method anticipates a wide variety of variations in the basic theme of implementation, but can be generalized as depicted in FIG. 14 (1400) as a lens formation method using hydrophilicity alteration comprising:
(1) generating a pulsed laser radiation output from a laser source (1401);
(2) distributing the pulsed laser radiation output across an input area of a microscope objective (1402);
(3) accepting the distributed pulsed radiation into a numerical aperture within the microscope objective to produce a focused laser radiation output (1403); and
(4) transmitting the focused laser radiation output into a PLM to modify the hydrophilicity within the PLM (1404).

This general method may be modified heavily depending on a number of factors, with rearrangement and/or addition/deletion of steps anticipated by the scope of the present invention. Integration of this and other preferred exemplary embodiment methods in conjunction with a variety of preferred exemplary embodiment systems described herein is anticipated by the overall scope of the present invention. This and other methods described herein are optimally executed under control of a computer system reading instructions from a computer readable media as described elsewhere herein.

As generally depicted in FIG. 9 (0900, 0912), this region of hydrophilic alteration may form arbitrary optical lens structures as generally depicted in FIG. 10 (1000)-FIG. 13 (1300) having multiple optical inner layers of hydrophilic alteration as generally depicted in FIG. 9 (0900, 0921).

Lens Shaping/Formation Method (1500)

The present invention also teaches a lens shaping/formation method wherein a lens of arbitrary complexity may be formed within PLM. The lens shaping consists of different parts. First the lens diopter and curvature have to be calculated depending on the selected material. The laser wavelength afterward is also adjusted towards this material. The AOM functions as the shutter and also as a variable power attenuator in the setup, allowing (in combination with the scanner) the lens structure to be precisely shaped inside the polymer. The AOM is controlled by the input images of the calculated lens information, providing the laser power information for each area (micrometer) of irradiated area. The scanner afterward distributes the power to the correct location and the microscope objective focuses the pulsed laser beam to the desired focus spot inside the polymer. The PLM sample is kept in a sample holder after the microscope objective and is optionally positioned on a stage system (mechanized X/Y/Z positioning system) to allow the shaping of a larger lens structure. The stage system could also be replaced with a mirrored laser arm which ends with the microscope objective. The mirrored arm in this case would not only replace the stage system but the whole camera and scanner board.

Figure 15:
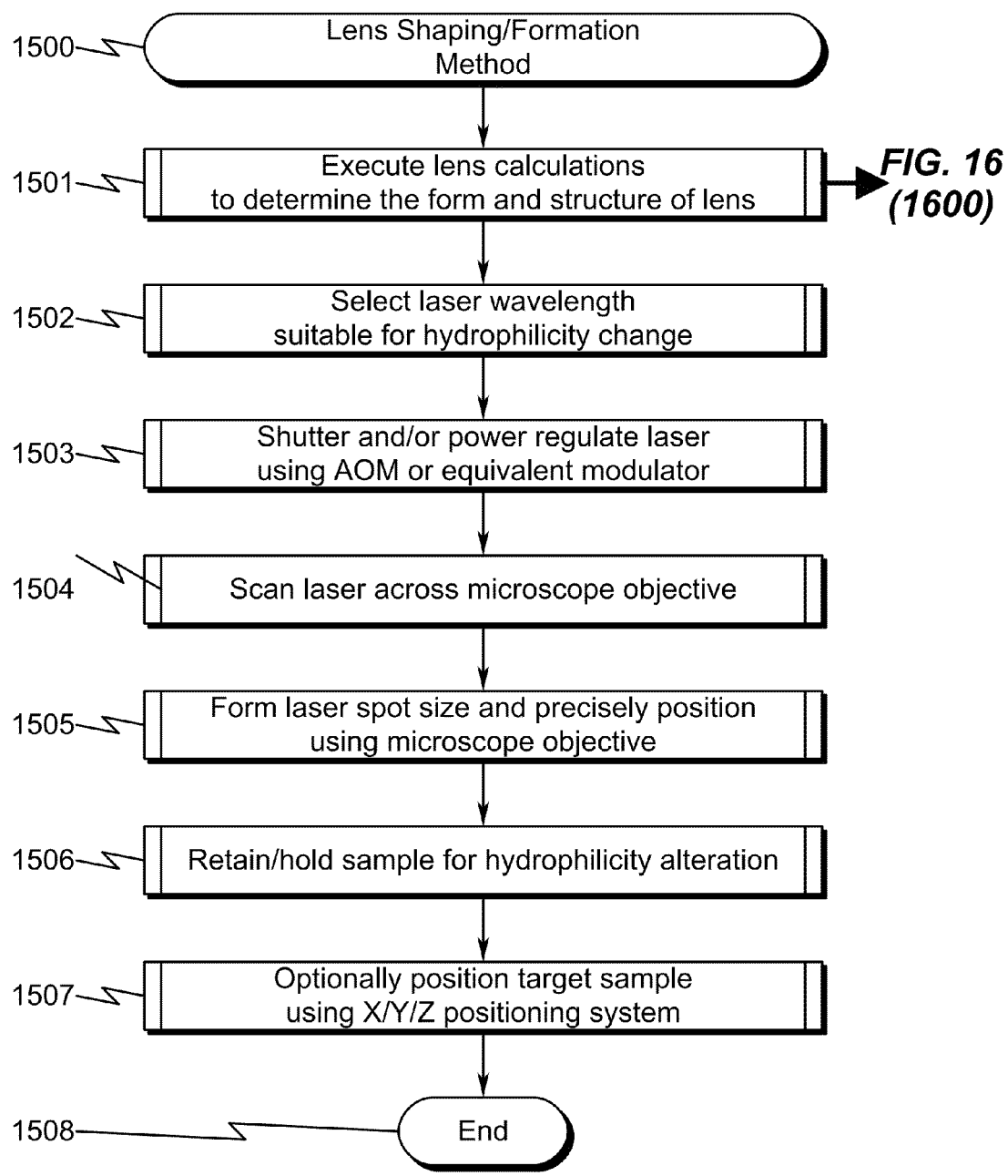
FIG. 15 illustrates an exemplary lens shaping/formation method flowchart used in some preferred embodiments of the present invention.

The present invention method may incorporate an embodiment of this lens shaping/formation method as depicted in FIG. 15 (1500) comprising:
(1) executing lens calculations to determine the form and structure of lens to create (1501);
(2) selecting the laser wavelength suitable for the desired hydrophilicity change in the PLM (1502);
(3) shuttering and/or power regulating a laser using an AOM or equivalent modulator to generate laser pulses (1503);
(4) scanning the laser pulses across a microscope objective (1504);
(5) forming a laser spot size and precisely positioning the focused laser within a PLM using a microscope objective (1505);
(6) retaining/holding the PLM for hydrophilicity alteration by the laser pulse stream (1506); and
(7) optionally positioning the target PLM sample using X/Y/Z positioning system (1507).

This general method may be modified heavily depending on a number of factors, with rearrangement and/or addition/deletion of steps anticipated by the scope of the present invention. Integration of this and other preferred exemplary embodiment methods in conjunction with a variety of preferred exemplary embodiment systems described herein is anticipated by the overall scope of the present invention.

This method may be applied to one or more layers within the PLM to achieve formed lens structures of arbitrary complexity. The lens calculations associated with this procedure as identified in step (1) are detailed in FIG. 16 (1600) and described below.

Lens Calculation Method (1600)

The present invention also teaches a lens calculation method wherein lens parameters are used to determine the internal PLM lens structure that is customized for a particular patient and their unique optical requirements. This method generally involves the following steps:
Calculating the curvature of the lens to be formed;
Determining the required lens depth;
Calculating the number of zones which must be processed via the laser;
Determining the zone radius for each zone to be processed;
Create phase wrapping lens data files for the laser; and
Loading the data files into the RIS mapping system.
These steps will now be discussed in more detail.

Before the lens parameters for a custom intraocular lens (IOL) can be calculated the patient needs to be examined, the different existing aberrations can be measured and the needed diopter (Dpt) changes can be evaluated. The material (n) for the shaping process has to be known to calculate the lens curvature (C).

$$C = \frac{Dpt}{(n'-n)} \quad (1)$$

Where n is the refractive index of the original IOL material and n' is the refractive index after the RIS shaping, and therefore the refractive index of the new lens.

$$C = \frac{1}{r} \quad (2)$$

The curvature is related to lens radius (r) and the radius can be calculated with the lens diameter $2w_{Lens}$ and the lens depth $h_{Lens}$.

$$r = \frac{h_{Lens}^2 + w_{Lens}^2}{2h_{Lens}} \quad (3)$$

Afterward the Phase Wrapping Lens Information is calculated for the given information and the output images are created. All required information for the Phase Wrapping Lens already exists in the information of the original lens and its curvature. The Phase Wrapping depth of the lens is determined by the refractive index change amount. Afterward the radius of each zone and for the curvature information of each zone can be easily calculated. Depending on the shaping technique the lens diopter can be larger than the objective field size, in this case a stage system (as described above) is used to align the different areas for the lens shaping. To allow this technique the input images are chopped into their images sizes to represent the block system.

Figure 16:
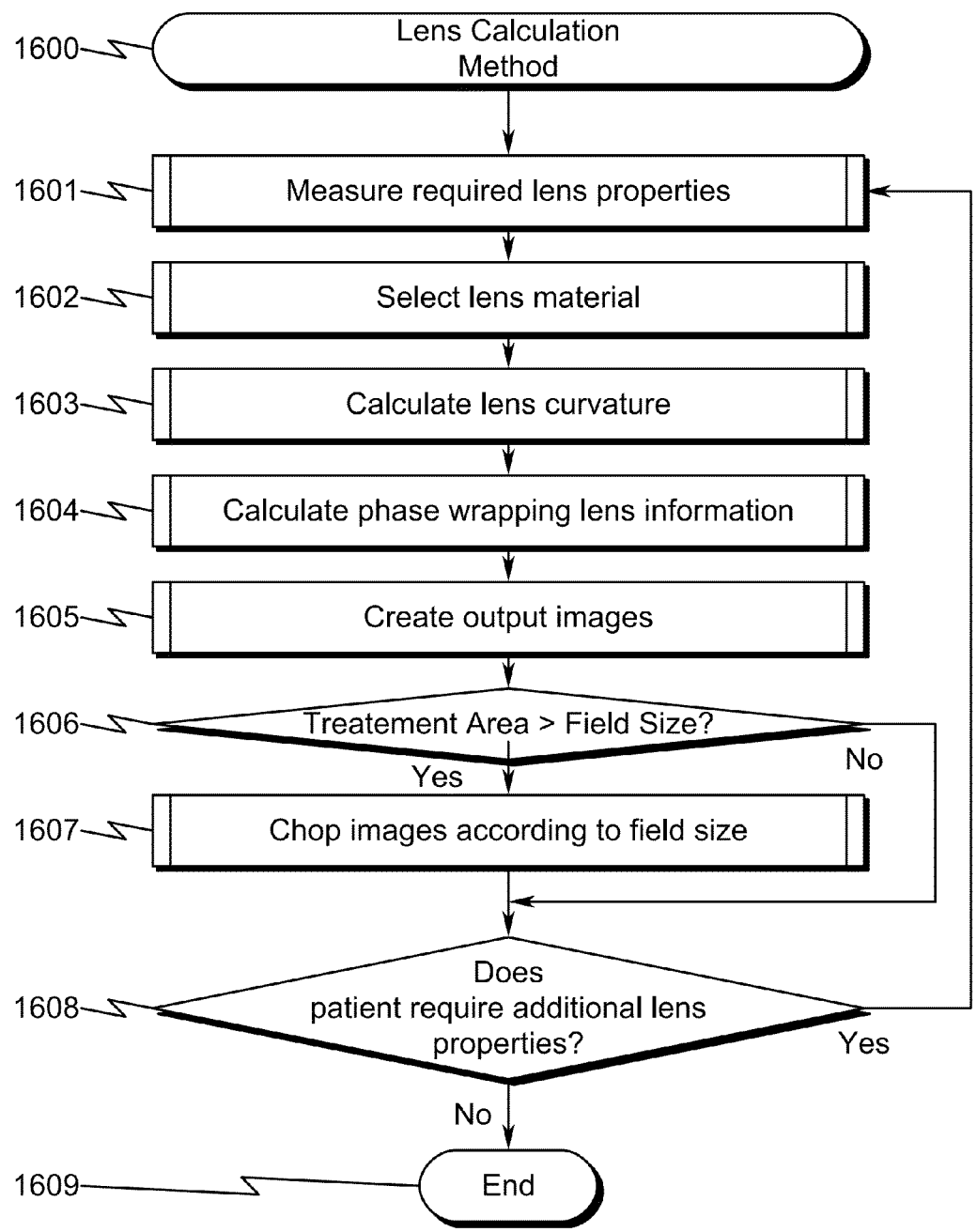
FIG. 16 illustrates an exemplary lens calculation method flowchart used in some preferred embodiments of the present invention.

The lens calculation method described above and generally depicted in FIG. 15 (1500, 1501) may be embodied in many forms, but several preferred embodiments of the present invention method may implement this method as depicted in FIG. 16 (1600) using the following steps:
(1) measuring or determining required lens properties for desired optical performance (1601);
(2) selecting a lens material appropriate for lens fabrication (1602);
(3) calculating the desired lens curvature (1603);
(4) calculating phase wrapping lens information necessary to form the lens (1604);
(5) creating output images that correspond to the desired phase wrapping lens characteristics (1605);
(6) determining if the lens treatment area is larger than the objective field size, and if not, proceeding to step (8) (1606);
(7) chopping the output images into segments that fit within the field size (1607);
(8) determining if the patient (or lens formation) requires additional lens properties, and if so, proceeding to step (1) (1608); and
(9) terminating the lens calculation method (1609).
This general method may be modified heavily depending on a number of factors, with rearrangement and/or addition/deletion of steps anticipated by the scope of the present invention. Integration of this and other preferred exemplary embodiment methods in conjunction with a variety of preferred exemplary embodiment systems described herein is anticipated by the overall scope of the present invention.

This method may be applied to the formation of lenses that are retained/held by a staging apparatus, or in some circumstances the lens shaping/formation process may be performed in situ within the eye of a patient. In this situation, the lens PLM may be surgically inserted into the patient while the PLM is in a generally unmodified (or previously modified) state and then "dialed-in" to provide optimal vision for the patient.

Application #1

Optical Lens (1700)-(1800)

The following experimental application example 5 discusses an internal hydrophilicity change for a polymeric acrylic polymer suitable for making optical lenses.

Step 1—Preparation of Testing Optical Material

A small sheet of crosslinked polymeric copolymers may be constructed by free radical polymerization of
(1) 140 grams of mixture of butylacrylate, ethylmethacrylate,N-benzyl-N-isopropylacrylamide, and ethylene glycol dimethacrylate;
(2) 11.4 grams of 2-[3-(2H-benzotriazol-2-yl)-4-hydroxyphenyl]ethyl methacrylate; and
(3) a yellow dye less than 0.5%.
under a curing cycle starting at 65° C. up to 140° C. for a total time of approximately 14 hours in a glass mold sealed with silicone tube. Slightly yellow transparent sheet, about 2 mm thick, obtained this way can be cut into round buttons which can be further lathe machined into intraocular lenses. Alternatively, small trips can also be cut out from the sheet or from the buttons for laser treatment. The refractive index of the yellow sheet or button prepared this way is approximately 1.499.

Step 2—Pre-Soaking

A small strip (1.91 mm×1.33 mm×14.35 mm) of an optically transparent lens material prepared above weighs 38.2 mg. This strip of lens material is soaked in water until no more weight increase, an indication for reaching saturation at room temperature. The saturated strip, after water droplets on its surface are wiped with dry paper tissues, weighs 38.3 mg, indicating water absorption is approximately 0.3%.

Step 3—Laser Treatments

Figure 18:
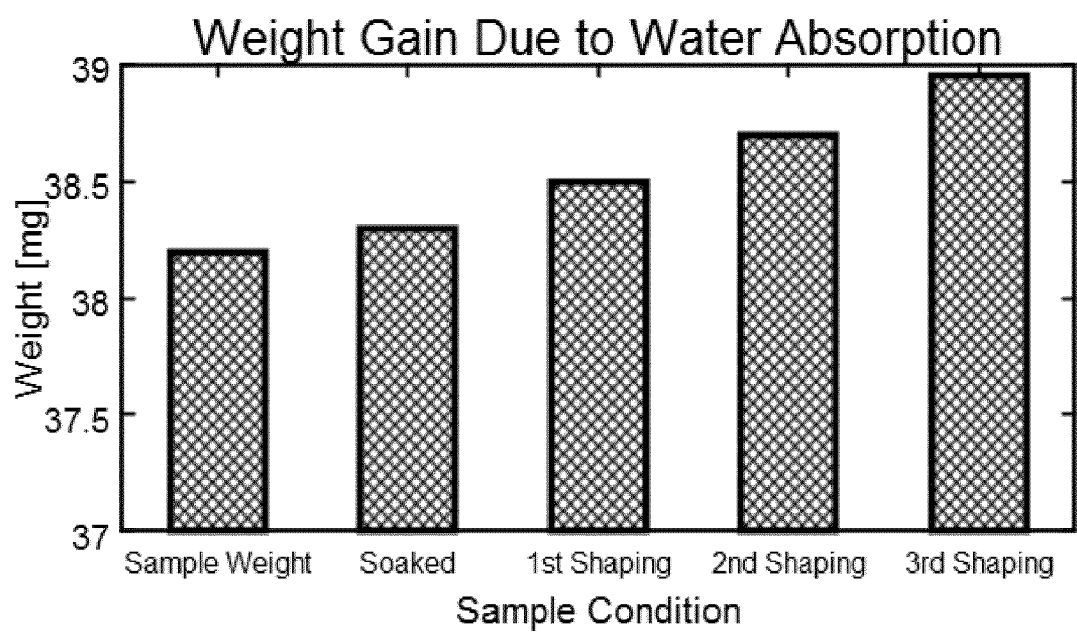
FIG. 18 illustrates a graph of experimentally measured PLM water absorption measurements.

The water saturated strip was then exposed to laser pulses from a femtosecond laser source (pulse width: 200 fs, repetition rate: 50 MHz, energy per pulse: 5.4 nJ, wavelength: 780 nm). Only a predetermined region (2 mm×2 mm×165 μm, 165 μm is the thickness of the treated region) as generally illustrated in FIG. 17 (1700) of the strip was treated. After the treatment the strip was allowed to be saturated with water and then weighed again. The strip was 38.9 mg with an increase of 0.2 mg which represents approximately 30% water absorption by the treated region (0.2 mg÷2×1.9×0.165=0.318=32%). After the first region was treated, a second region of same dimension was treated, approximately another 0.2 mg increase was observed. This way, a total of 3 regions were treated, final strip weights 38.9 mg. The weight gains after each laser treatment are summarized in the graph depicted in FIG. 18 (1800).

Application #2

Diffraction Gratings (1900)-(2400)

The following experimental application example discusses the use of the present invention as applied to Diffraction gratings efficiency dependency on water absorption.

Step 1

Figure 19:
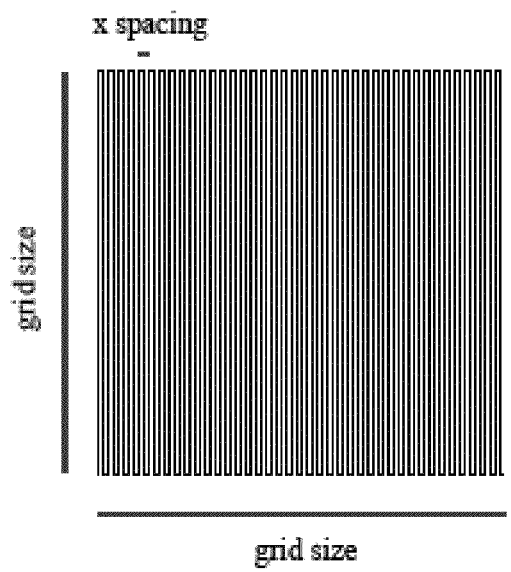
FIG. 19 illustrates an exemplary diffraction grid pattern as taught by the present invention.

A diffraction grating was shaped inside the acrylic polymeric material as generally depicted in FIG. 19 (1900). The grid size is 3 mm with an X spacing of 18 um in this example.

Step 2

The sample is then water saturated.

Step 3

Figure 20:
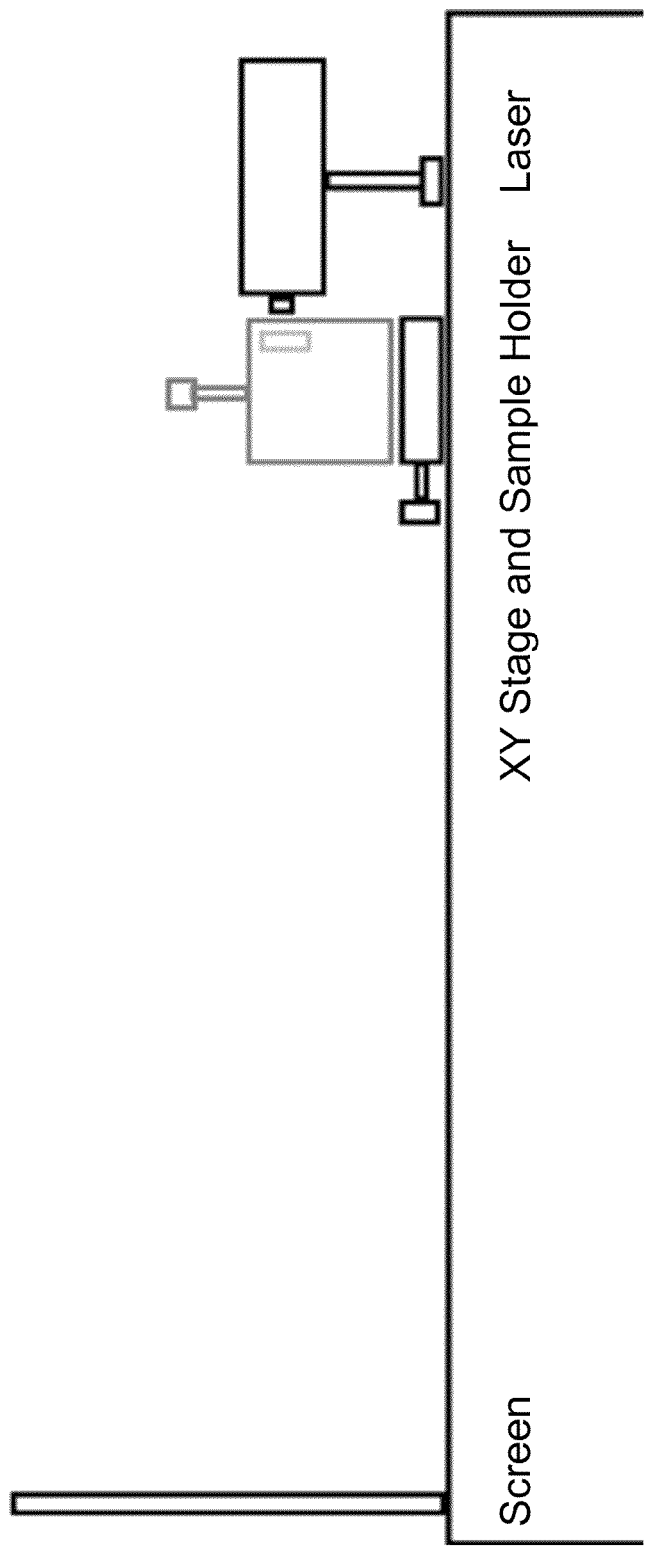
FIG. 20 illustrates an exemplary experimental refractive index measurement setup as taught by the present invention.
Figure 22:
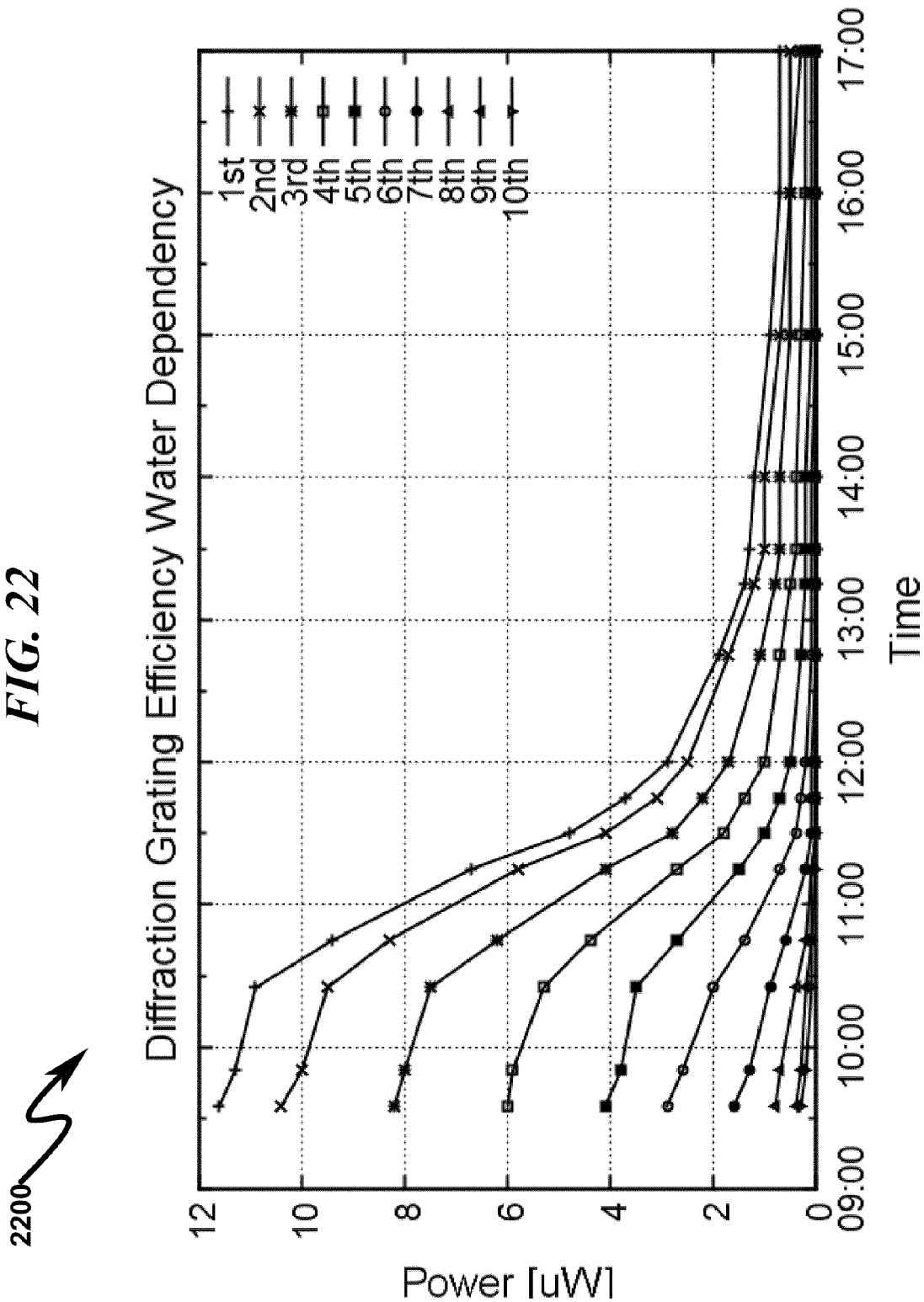
FIG. 22 illustrates an exemplary experimentally measured diffraction grating power measurement over time as taught by the present invention.
Figure 23:
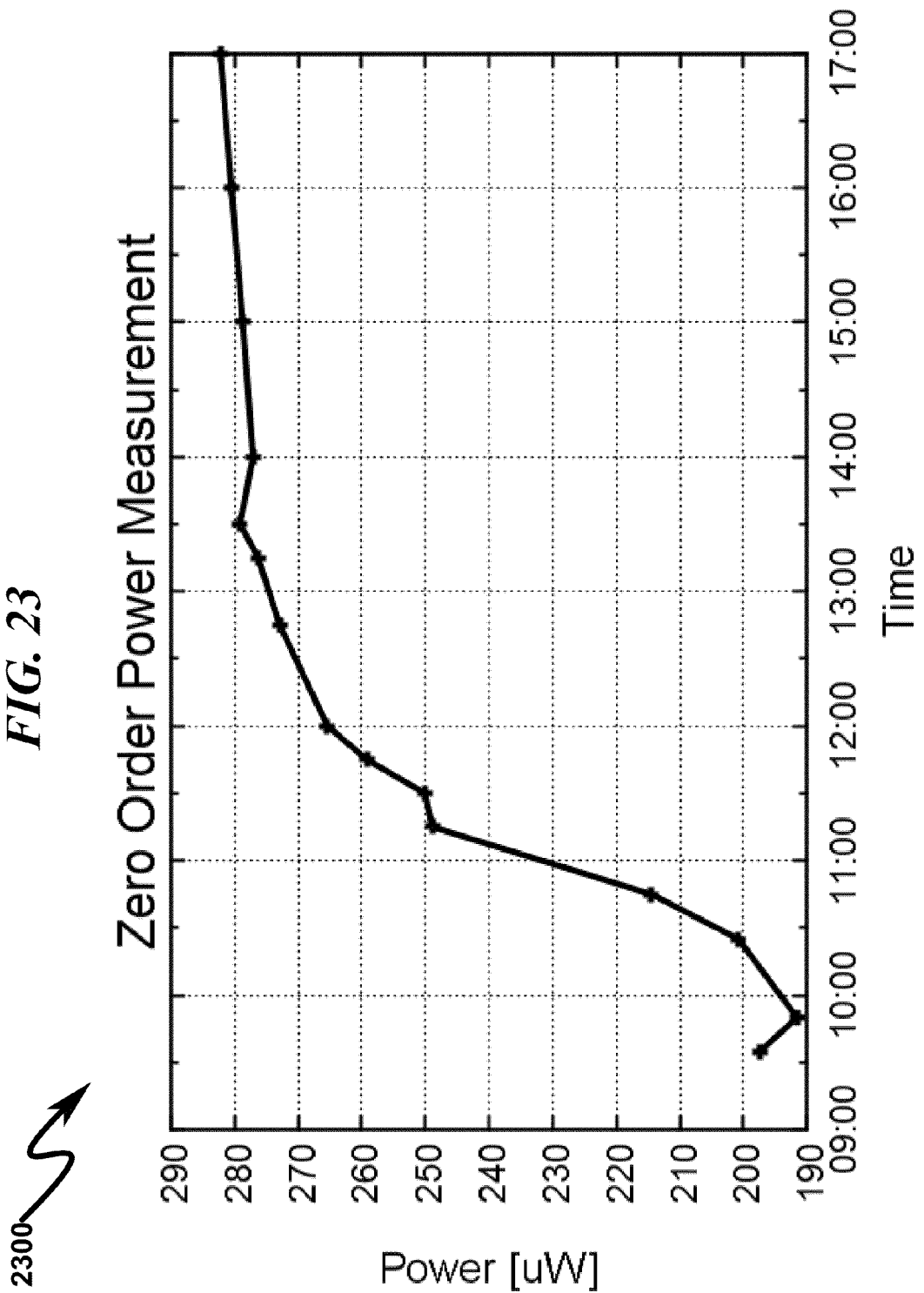
FIG. 23 illustrates an exemplary experimentally measured diffraction grating 0 order power measurement as taught by the present invention.

The efficiency of the refractive index grating was measured (2103) using the setup depicted in FIG. 20 (2000) for different scan speeds. A red (640 nm) laser was placed in front of the sample. The sample is mounted on a set of XY stages to allow positioning of the grating in regards of the laser. At some distance a screen (2101-2103) was positioned and the power of the different orders of the gratings (as depicted in FIG. 21 (2100)) is recorded for different times as depicted in FIG. 22 (2200). The power in the $1^{st}$ to the $10^{th}$ order decreases with the water desaturation as illustrated in FIG. 22 (2200), while the energy is going into the zero (0) order as generally depicted in FIG. 23 (2300).

Figure 24:
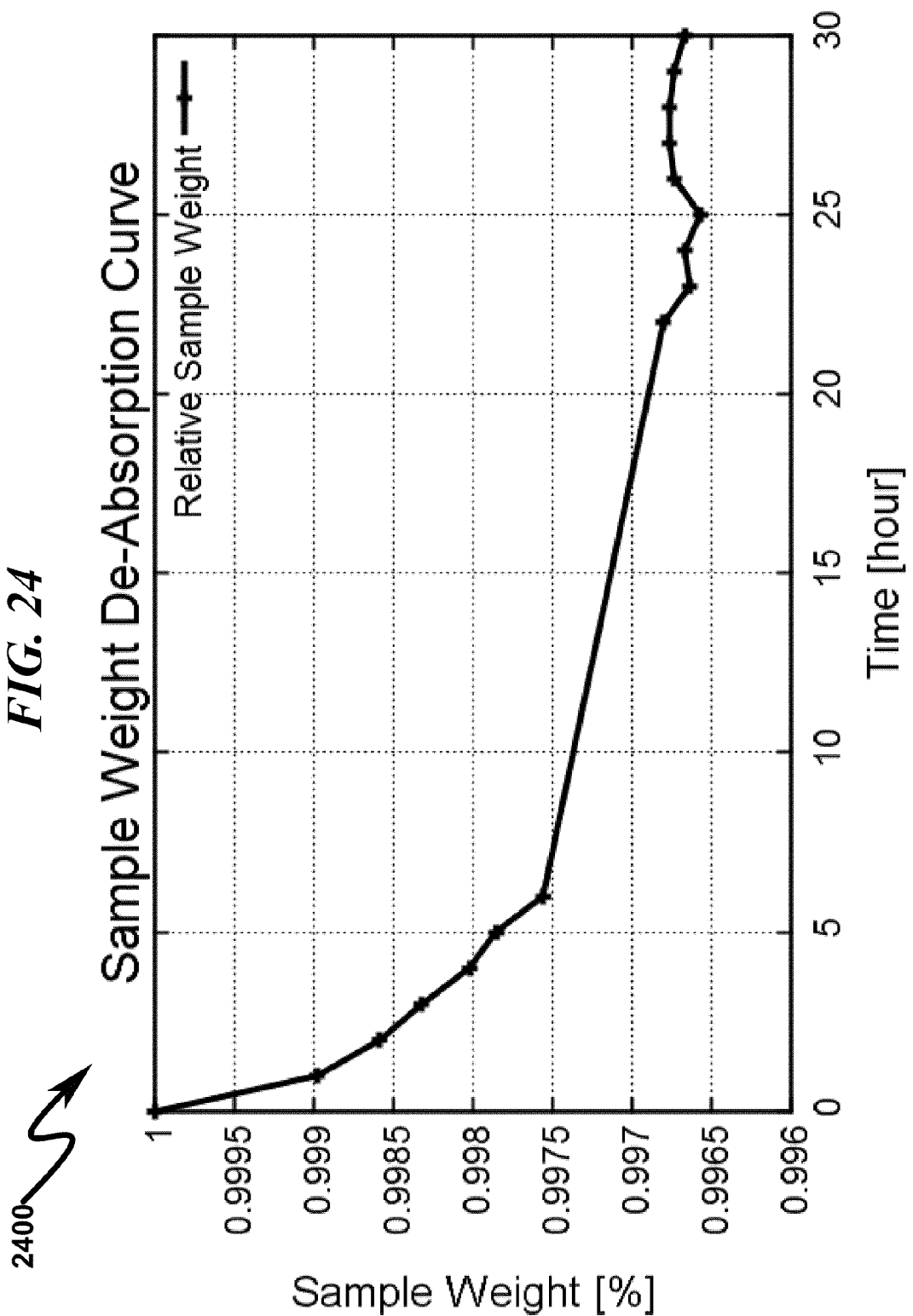
FIG. 24 illustrates an exemplary experimentally measured water de-absorption curve as taught by the present invention.

This can be compared with the water de-absorption curve of the acrylic polymeric material as depicted in FIG. 24 (2400) which shows the material weight loss due to water de-absorption. The graph in FIG. 24 (2400) shows the averaged sample weight measurement in percentage for 10 samples. The important information is shown in the first five (5) hours. The main change is occurring within the first five hours comparing the graphs in FIG. 23 (2300) and FIG. 24 (2400). The diffraction grating starts decrease slower because the grating is shaped inside the material and the water de-absorption takes some time before it will be noticed in the measurement. After the main water amount is de-absorbed the diffraction grating gets very weak.

Application #3

Phase Wrapping a Convex Lens (2500)-(2900)

The following experimental application example discusses a negative refractive index change due to hydrophilicity change.

Step 1

Figure 25:
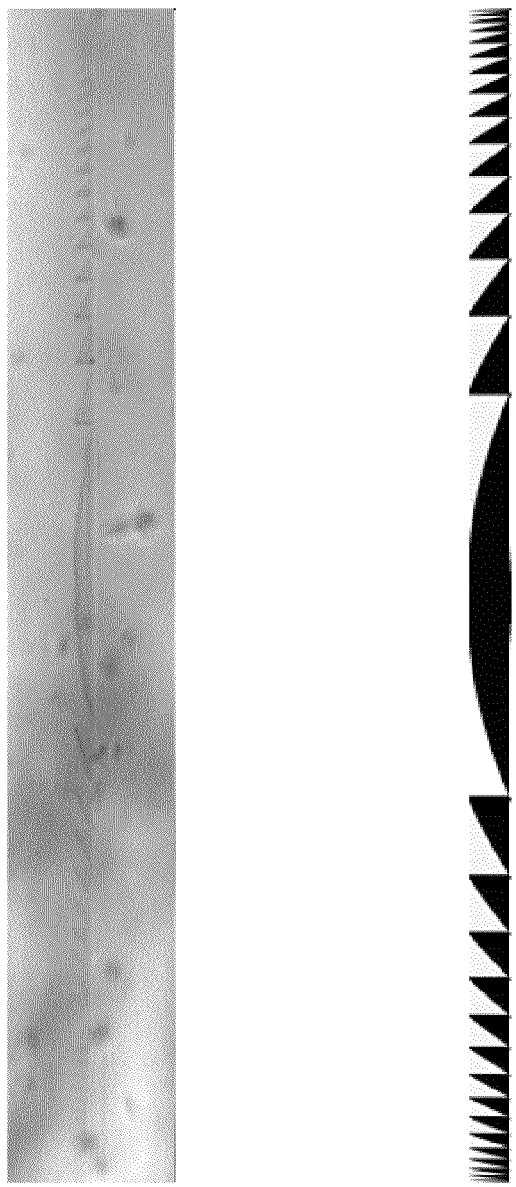
FIG. 25 illustrates an exemplary experimentally constructed convex phase wrapping DIC and theoretical side view as taught by the present invention.
Figure 26:
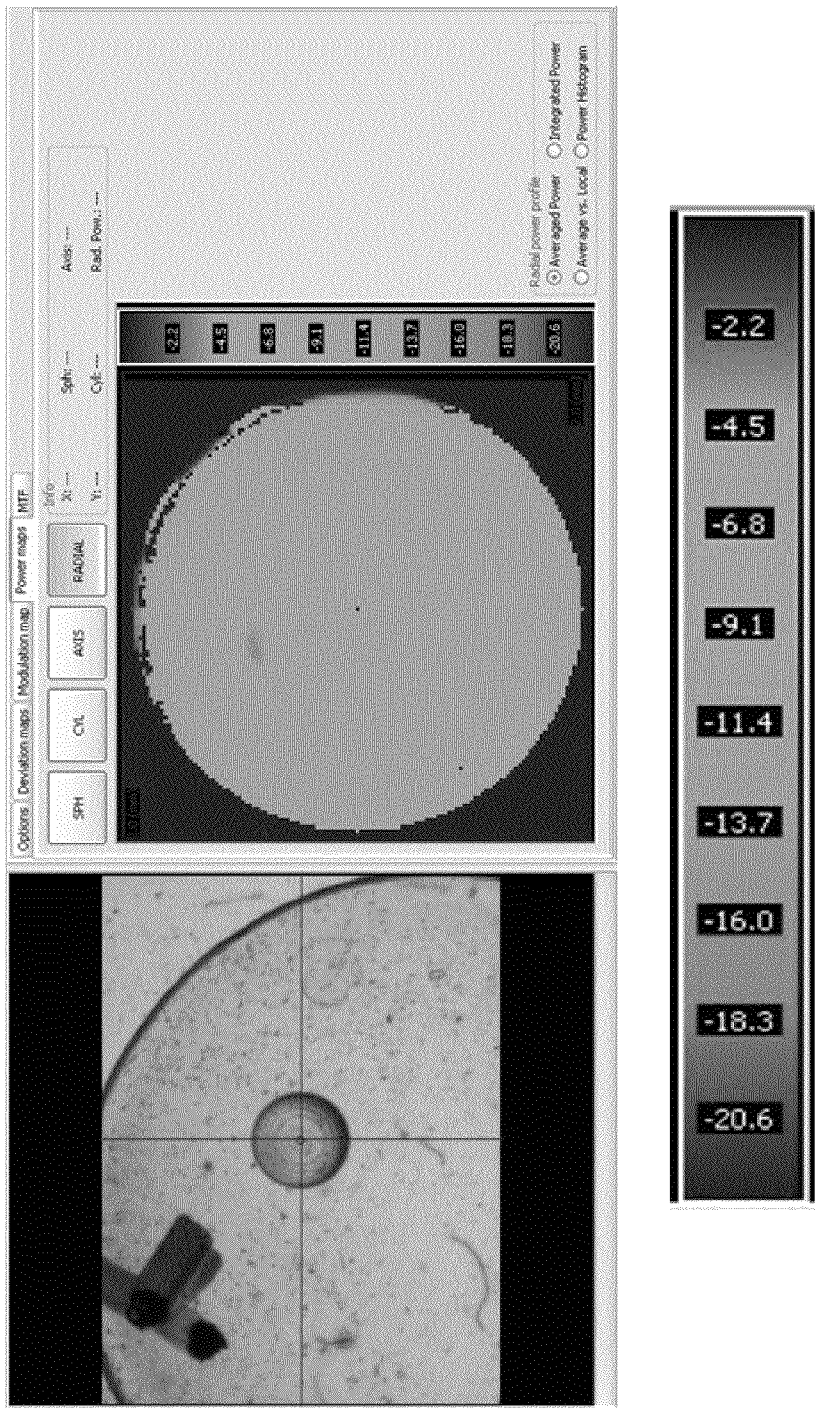
FIG. 26 illustrates a NIMO diopter reading of an exemplary experimentally constructed convex phase wrapping DIC and theoretical side view as taught by the present invention.

A lens shaping of a phase wrapping convex lens is generated as depicted in FIG. 25 (2500). The phase wrapping concave lens shows the negative refractive index change which is induced by the hydrophilicity change inside the material. The NIMO diopter reading for this structure is depicted in FIG. 26 (2600).

Figure 27:
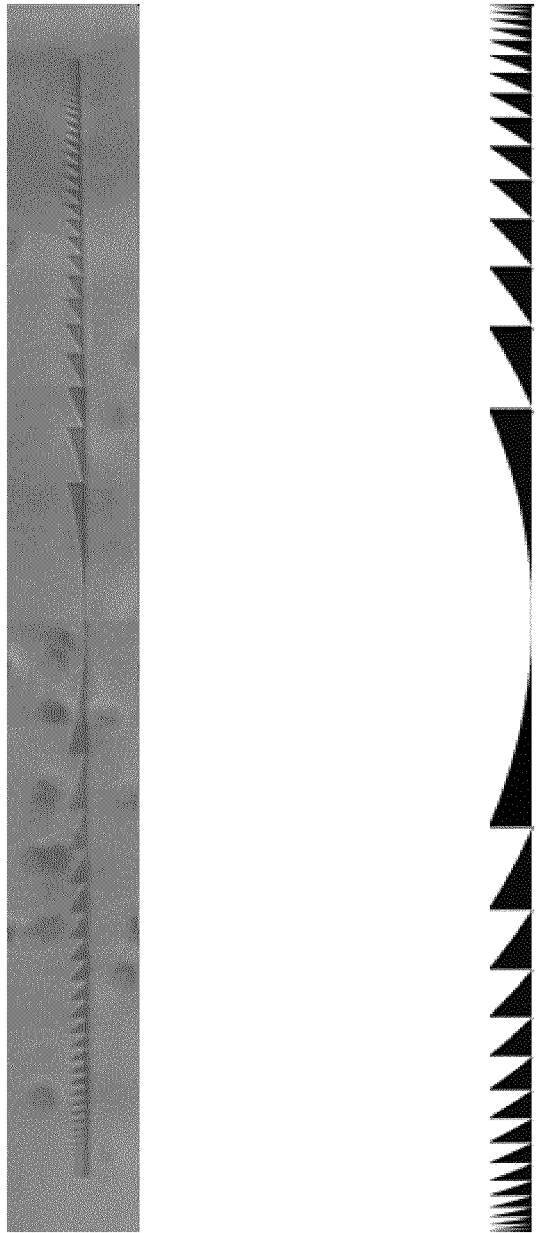
FIG. 27 illustrates an exemplary experimentally constructed concave phase wrapping DIC and theoretical side view as taught by the present invention.
Figure 28:
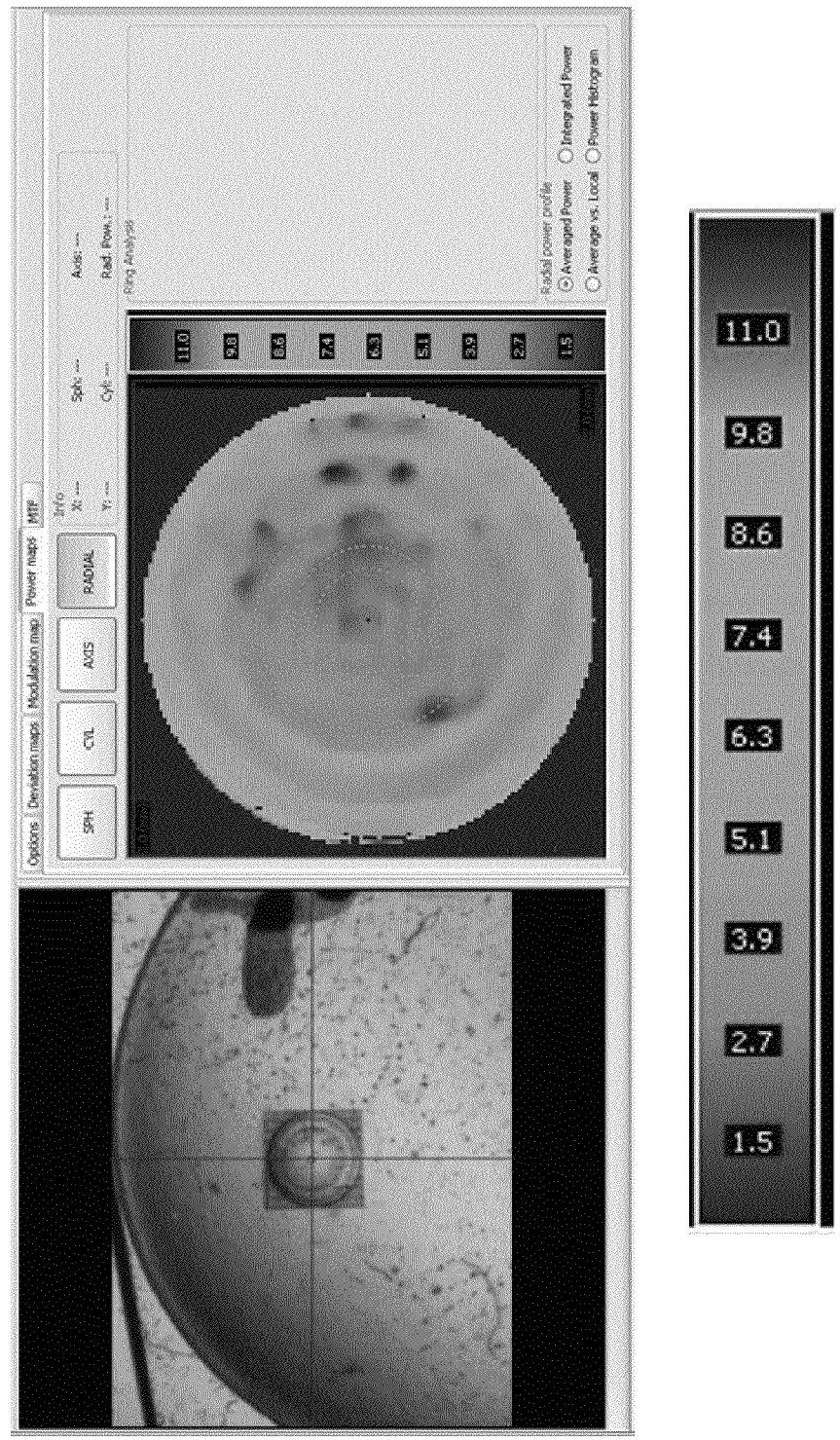
FIG. 28 illustrates a NIMO diopter reading of an exemplary experimentally constructed concave phase wrapping DIC and theoretical side view as taught by the present invention.

The convex phase wrapping lens shows a negative diopter reading and the concave phase wrapping lens as generally depicted in FIG. 27 (2700) shows a positive diopter reading. The NIMO diopter reading for this structure is depicted in FIG. 28 (2800).

Figure 29:
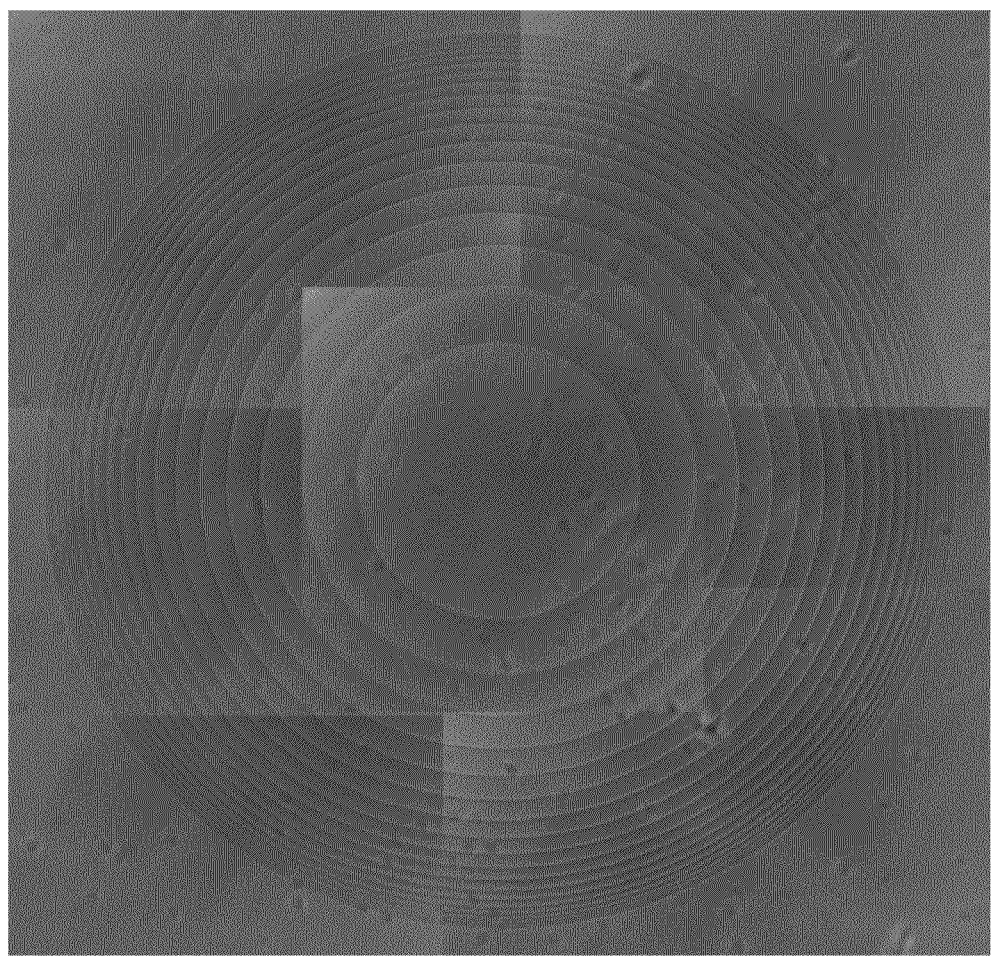
FIG. 29 illustrates an exemplary experimental 3 mm convex phase wrapping lens top view as constructed.

The image depicted in FIG. 29 (2900) illustrates an exemplary 3 mm convex phase wrapping lens top view as constructed.

Application #4

Water Saturation (3000)-(3100)

The following experimental application example discusses a full diopter reading only after water saturation of the material.

Step 1

A concave lens with a positive diopter reading was shaped.

Step 2

The lens diopter is measured after shaping.

Step 3

The lens is not stored in water but in air for 18 days and afterward placed in water.

Step 4

The diopter reading of the lens after placed in water is measured.

The diopter reading of the lens directly after shaping is minimal. The material still has to be water saturated before the final diopter reading is possible. During the shaping process it already can absorb some water, therefore some diopter reading will be possible after shaping but the full diopter reading will always only be possible after the material is fully water saturated.

Figure 30:
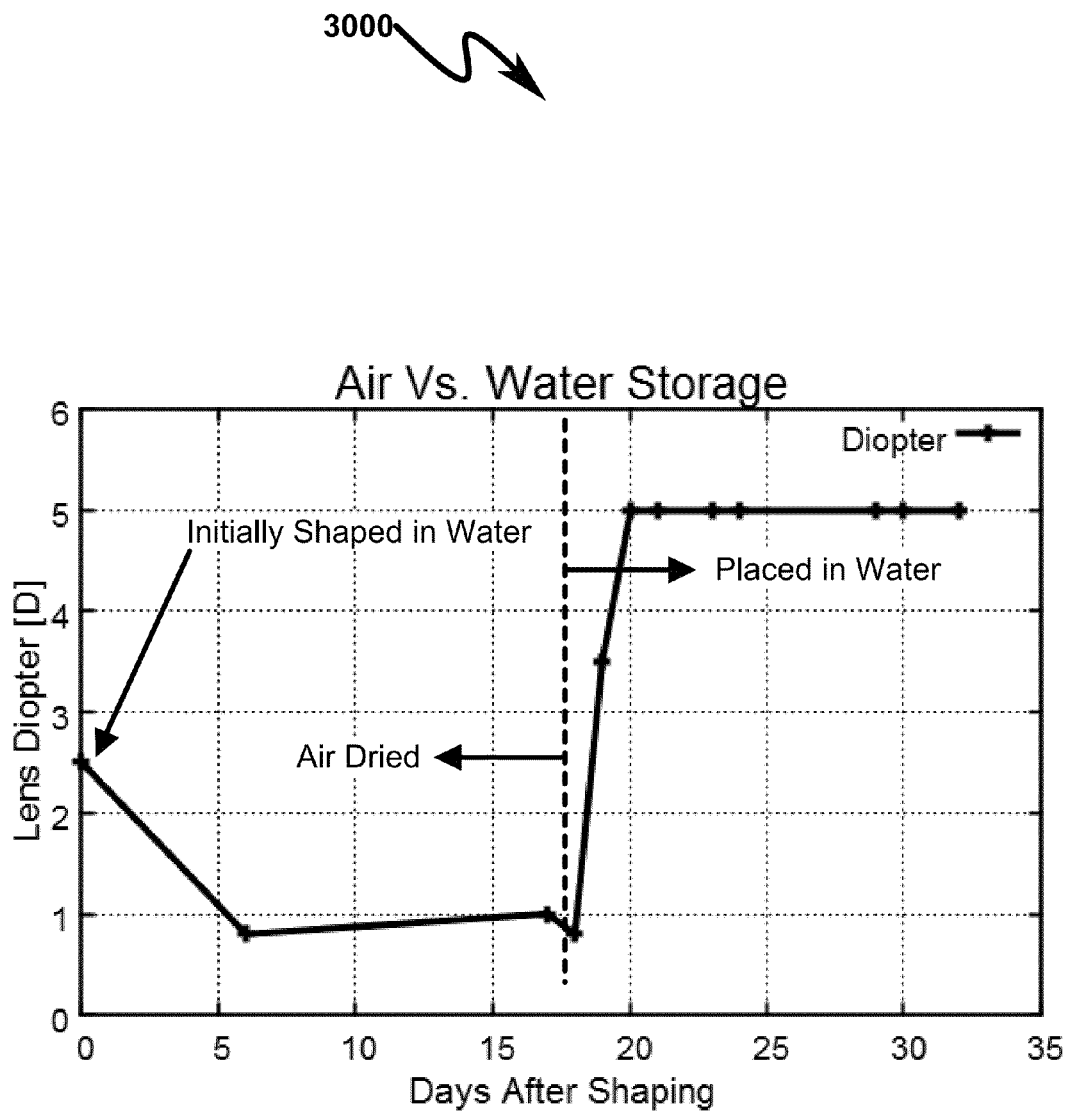
FIG. 30 illustrates an exemplary experimentally measured diopter reading as it relates to water absorption comparison as taught by the present invention, depicting the difference between air drying and water hydration on measured lens diopter readings.

After the lens is placed in water the lens diopter is fully recovered after 24 hours. FIG. 30 (3000) depicts the diopter reading of a 5 diopter 2 mm lens. The first diopter measurement directly after shaping was only 1.5D.

Figure 31:
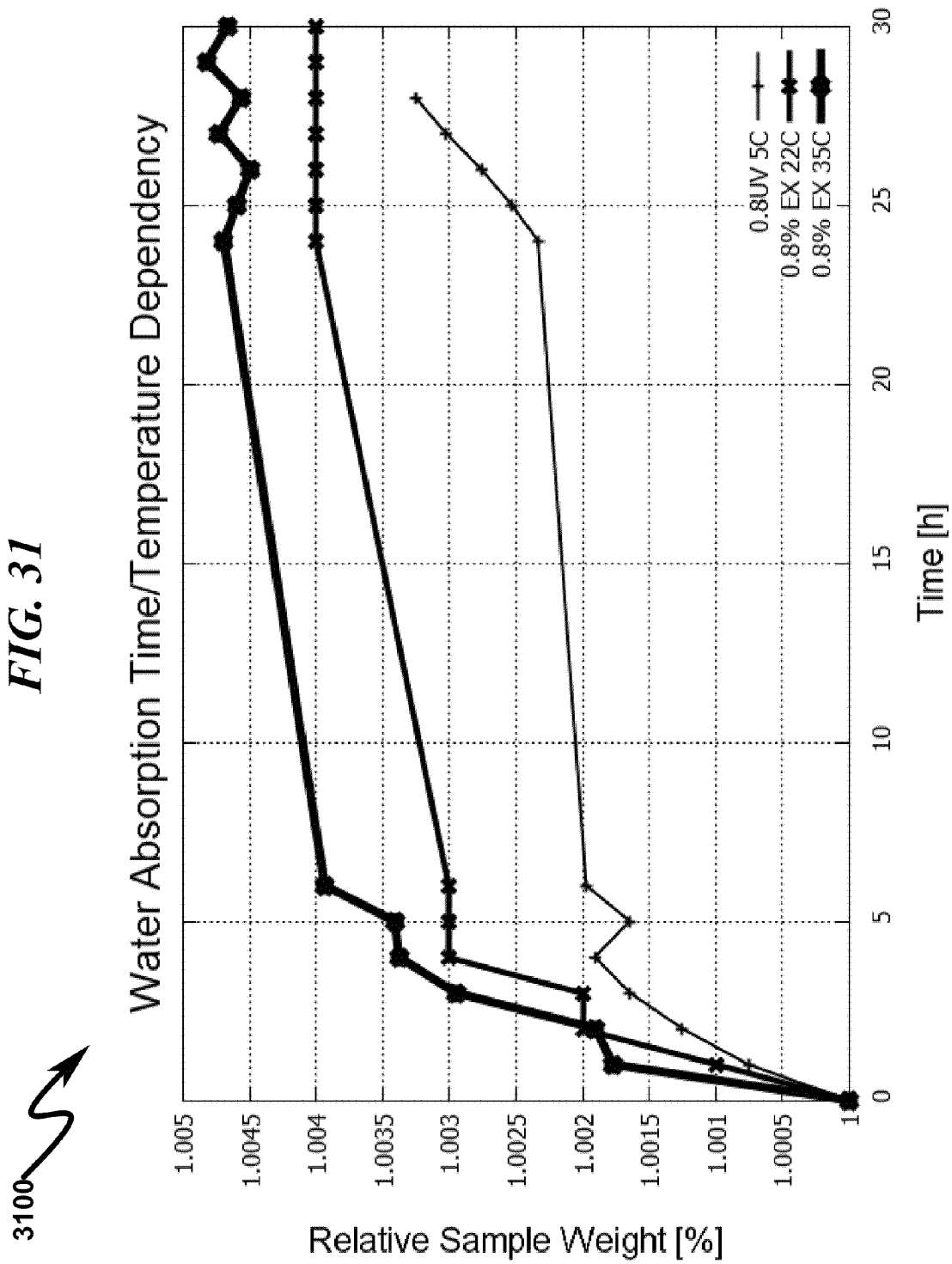
FIG. 31 illustrates an exemplary experimentally measured water absorption curve for water as taught by the present invention and its variation based on time and ambient temperature.

For comparison graph in FIG. 31 (3100) depicts the water saturation curve for the polymeric material and its relationship to time.

Application #5

Pre-Soaking

The following experimental application example discusses the diopter reading of a pre-soaked sample.

The saturation period can be shortened if the sample was pre-soaked in water before the lens shaping. Directly after shaping the lens shows a larger diopter reading and will recover to the full diopter value much quicker, compared to a non-pre-soaked sample. The pre-water soaking will only shorten the time period of the sample to fully saturate. It will not change the final diopter reading of the lens.

Application #6

Temperature Dependency (3100)

The following experimental application example discusses the temperature dependency of lens diopter.

The water absorption of the material is dependent on the surrounding temperature. An incubator can be used to change the sample temperature. After allowing the sample sufficient time to adapt to the temperature change the lens diopter was measured and differences of up to ±1D for different temperature settings were observed.

The water absorption is temperature dependent, therefore the diopter reading of the lens is also temperature dependent. This can be seen from the graph in FIG. 31 (3100), wherein more water is absorbed for 35 degree Celsius than for 22 degree Celsius.

Application #7

Diopter Memory (3200)

The following experimental application example discusses the temperature dependency of lens diopter.

The diopter of the treated area is fixed. The sample can be kept in air storage, never allowing it to develop the full lens diopter, but when placed in water the full diopter of the lens will recover to the full, theoretically calculated diopter after saturation.

Figure 32:
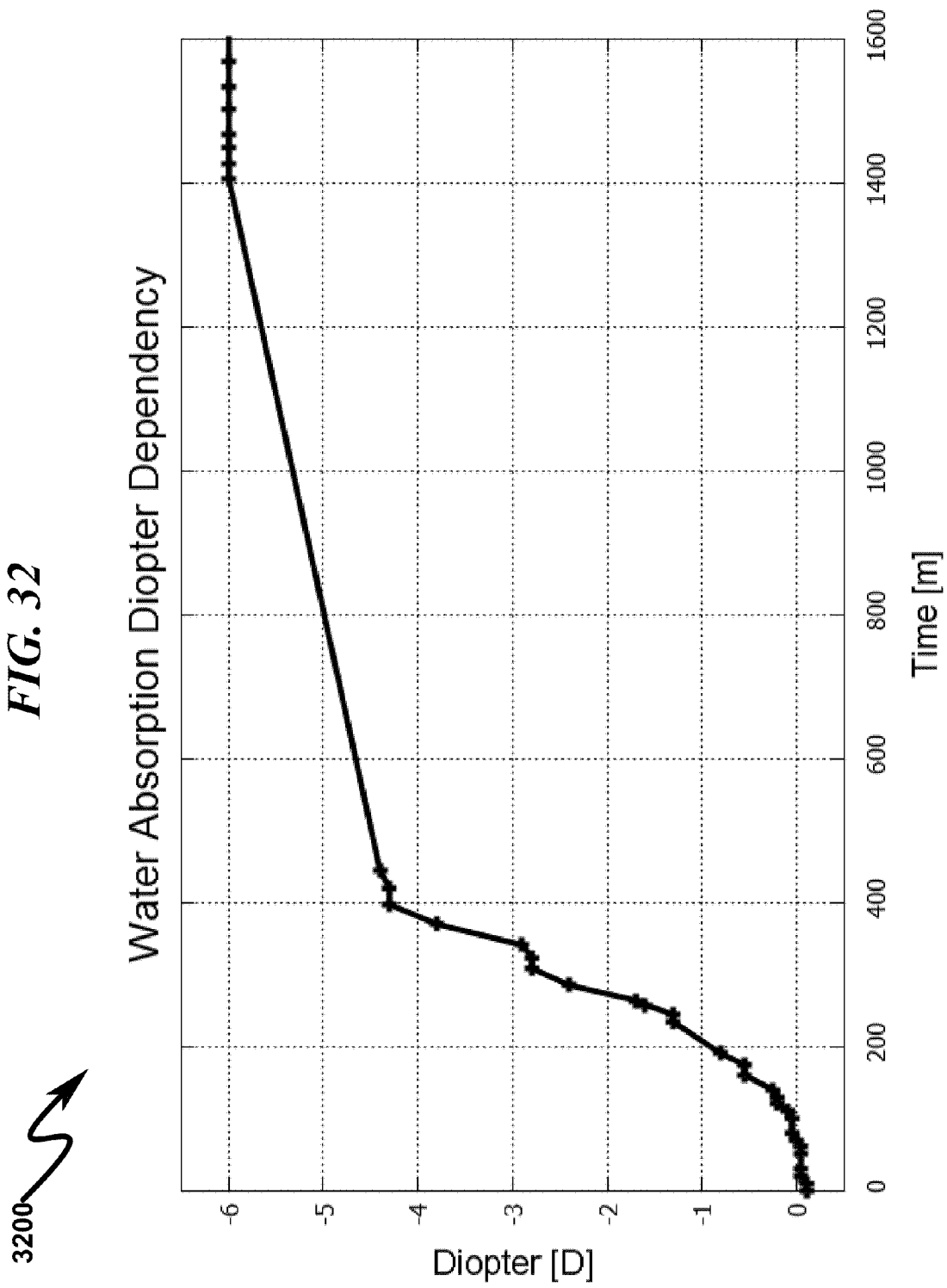
FIG. 32 illustrates an exemplary experimentally measured water absorption diopter dependency graph as taught by the present invention.

Diopter reading of sample increases when hydrated after sample was dehydrated, the lens starts with approximately 0D and increases the diopter reading to its full −6D within 27 hours as depicted in FIG. 32 (3200), which is in accordance with the image in FIG. 31 (3100).

In-Vivo Lens Shaping Method (3300)-(4000)

Figure 33:
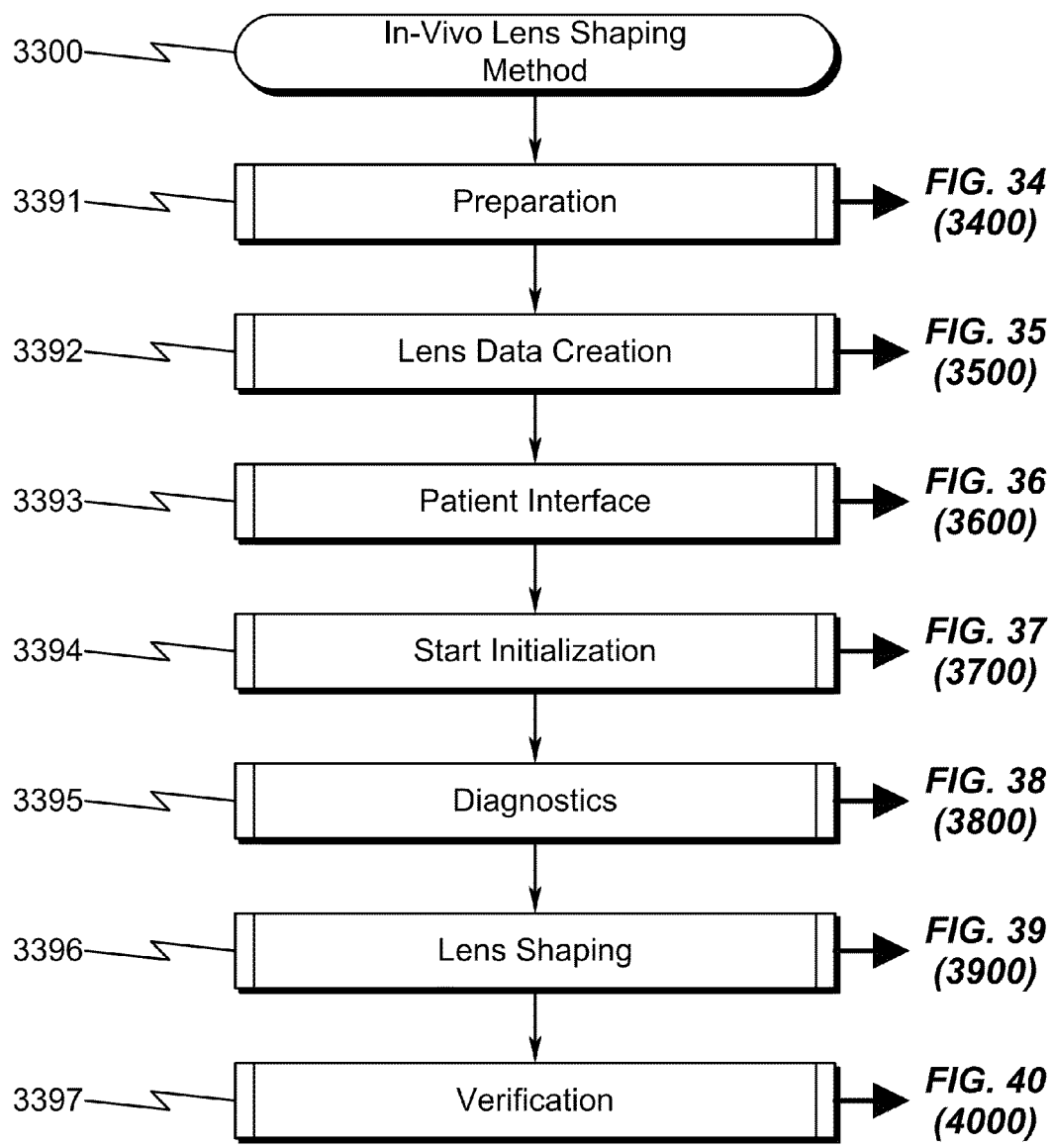
FIG. 33 illustrates an exemplary method flowchart depicting a generalized in-vivo lens shaping method as implemented by a preferred invention embodiment.

The present invention anticipates that lenses may be formed/shaped using the systems/methods described herein in-vivo as generally illustrated in FIG. 33 (3300), comprising the following steps:

(1) Preparation (3391);
(2) Lens Data Creation (3392);
(3) Patient Interfacing (3393);
(4) Start Initialization (3394);
(5) Diagnostics (3395);
(6) Lens Shaping (3396); and
(7) Verification (3397).

Figure 34:
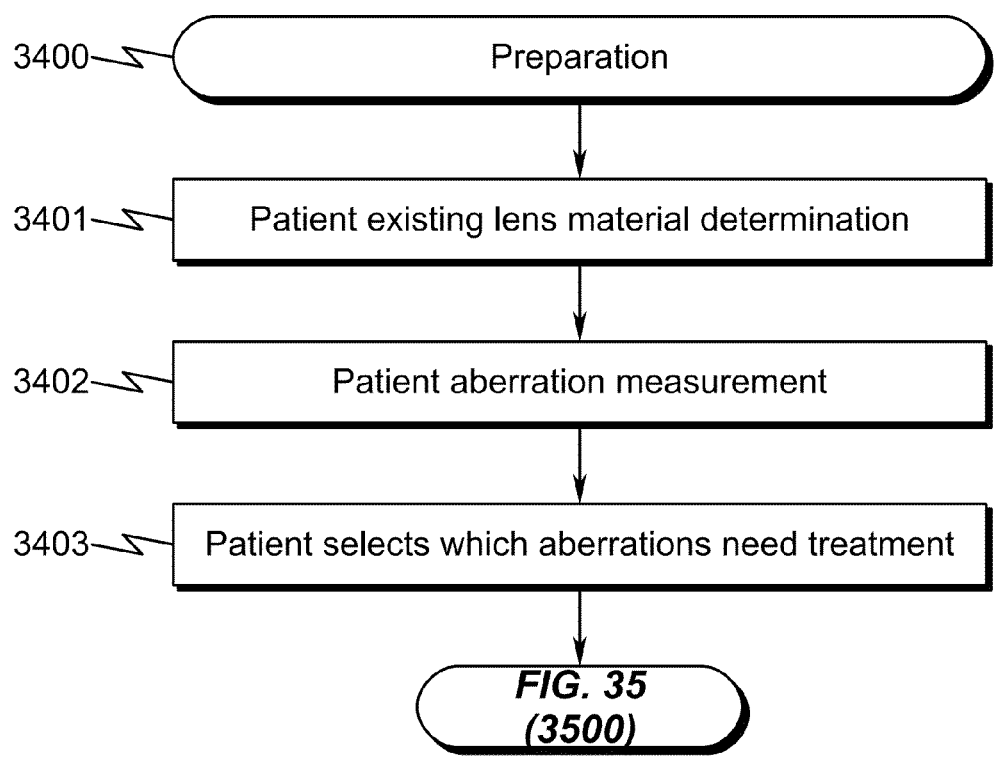
FIG. 34 illustrates an exemplary method flowchart depicting preparation details of an in-vivo lens shaping method as implemented by a preferred invention embodiment.
Figure 35:
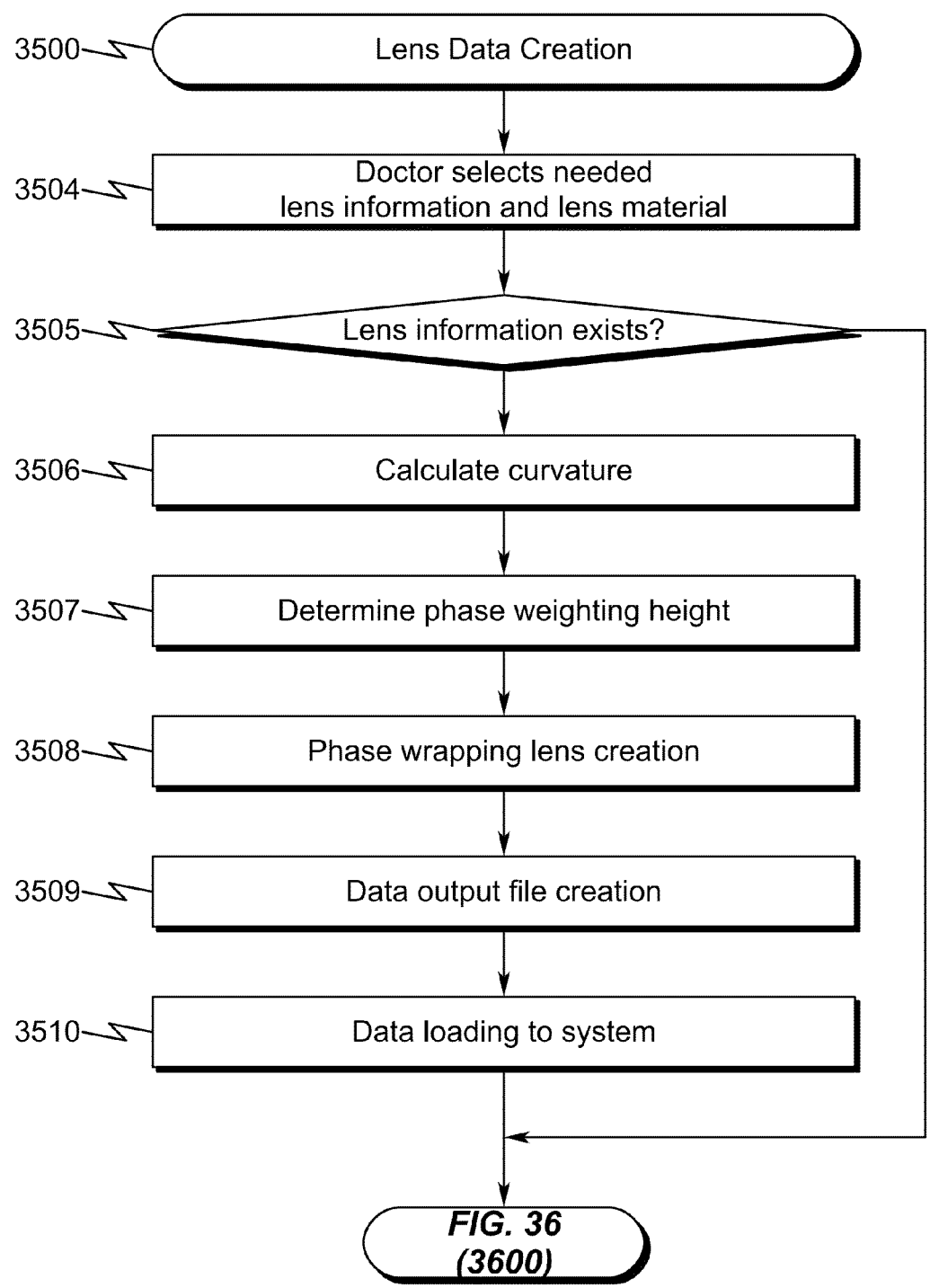
FIG. 35 illustrates an exemplary method flowchart depicting lens data creation details of an in-vivo lens shaping method as implemented by a preferred invention embodiment.
Figure 36:
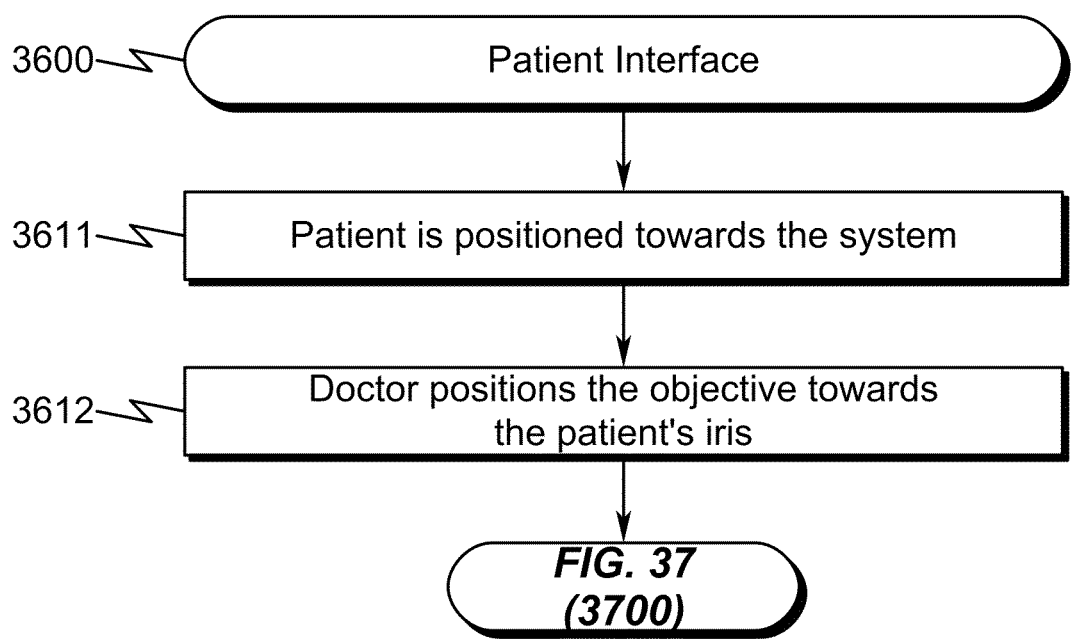
FIG. 36 illustrates an exemplary method flowchart depicting patient interface details of an in-vivo lens shaping method as implemented by a preferred invention embodiment.
Figure 37:
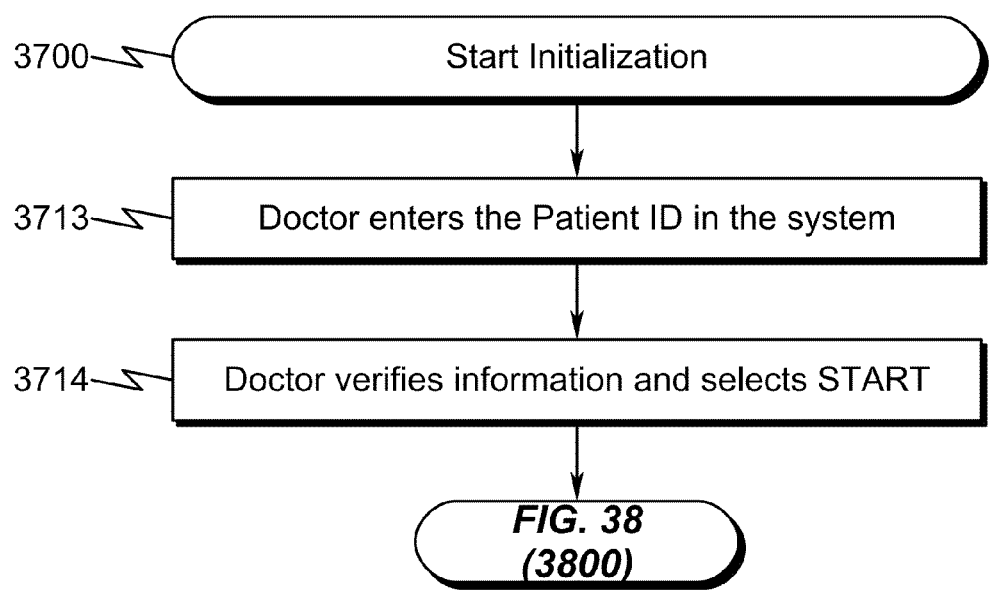
FIG. 37 illustrates an exemplary method flowchart depicting start initialization details of an in-vivo lens shaping method as implemented by a preferred invention embodiment.
Figure 38:
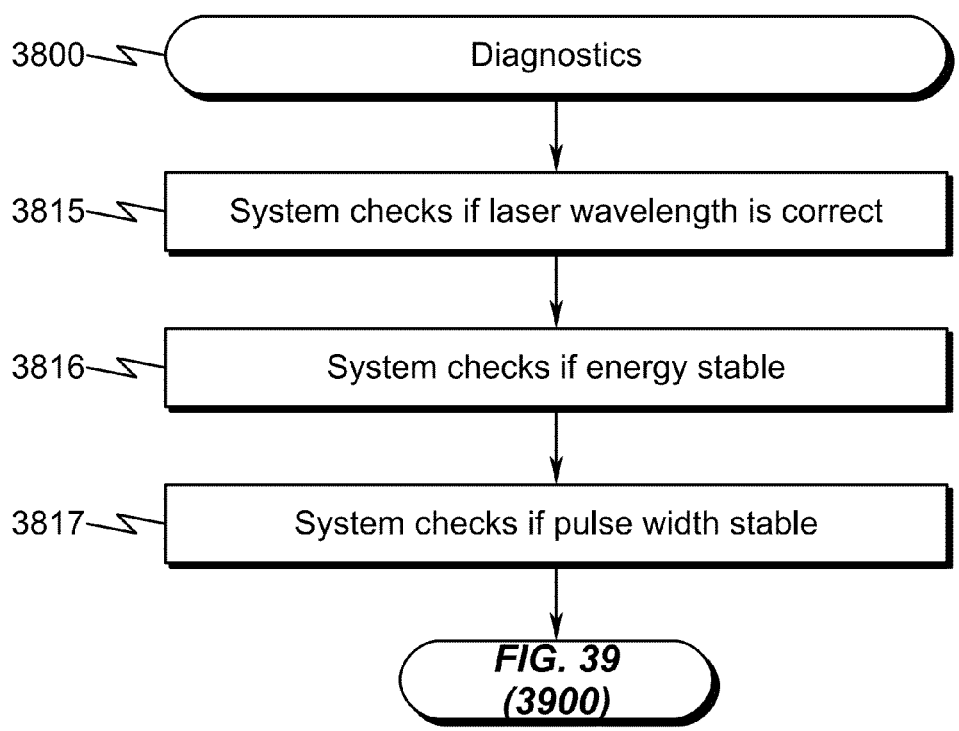
FIG. 38 illustrates an exemplary method flowchart depicting diagnostics details of an in-vivo lens shaping method as implemented by a preferred invention embodiment.
Figure 39:
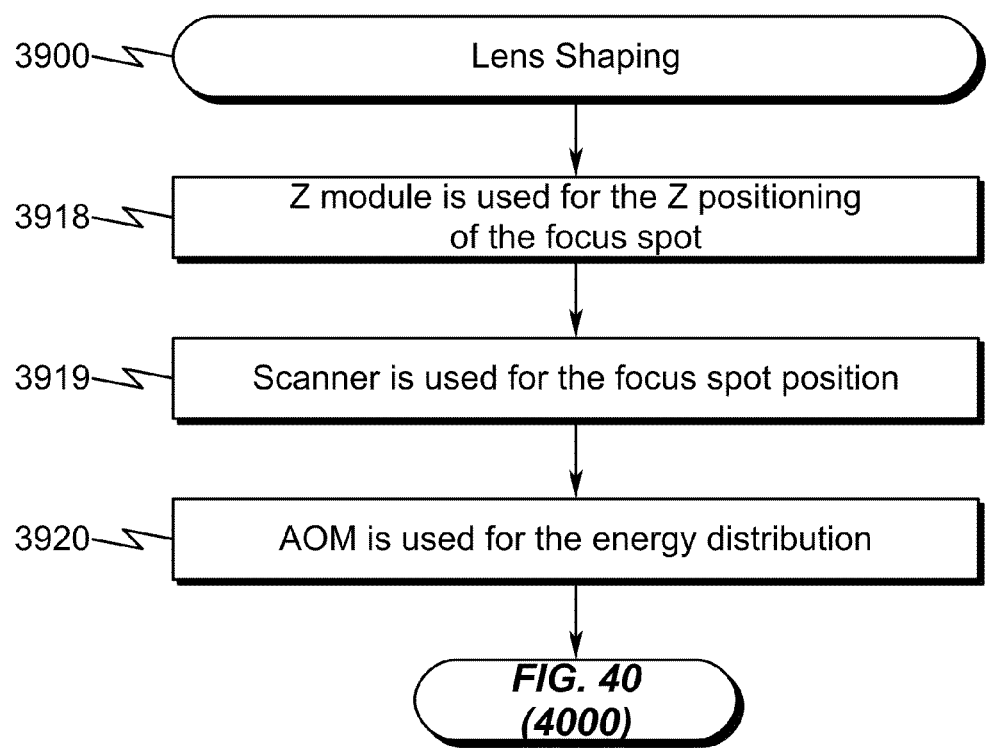
FIG. 39 illustrates an exemplary method flowchart depicting lens shaping details of an in-vivo lens shaping method as implemented by a preferred invention embodiment.
Figure 40:
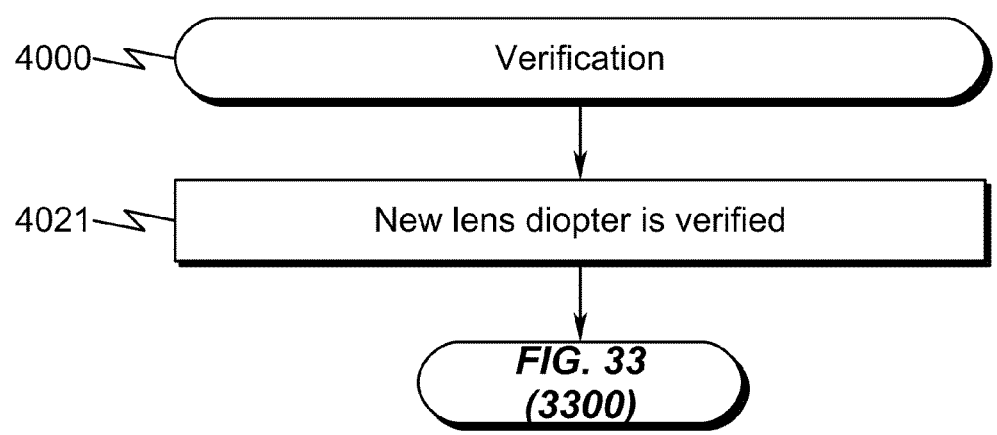
FIG. 40 illustrates an exemplary method flowchart depicting verification details of an in-vivo lens shaping method as implemented by a preferred invention embodiment.

As generally illustrated in FIG. 34 (3400)-FIG. 40 (4000), these generalized steps may be further defined in terms of more detailed steps as follows:

(1) Patient existing lens material determination (3401) wherein this information is used to determine the laser properties and to calculate the refractive index material change induced by the refractive index shaping.
(2) Patient aberration measurement (3402) wherein the different patient specific aberrations are determined.
(3) Patient selects which aberrations need treatment (3403) wherein the selection could be but is not limited to common vision defects like myopia, hyperopia and astigmatism.
(4) Doctor selects needed lens information and lens material (3504) wherein the selection is depending on the consultation with the patients' needs and the available options.
(5) Determining if needed lens information exists, and if the information already exists, proceeds to step (11) (3505). This section is completely software based and not accessible by the doctor or the patient. This step is integrated for the case that a patient has a unique diopter value which is not preloaded to the system.
(6) Calculating lens curvature (3506) wherein the curvature is depending on the required lens diopter and the refractive index change induced by the refractive index shaping and the surrounding refractive index change of the material.
(7) Determining phase weighting height (3507) wherein the height is depending on the induced refractive index change difference and therefore also the surrounding material.
(8) Phase wrapping lens creation (3508) wherein the information of the Phase Wrapping Lens is given by the Phase Wrapping Lens height and the original lens curvature information. For each layer the radii for each zone can be determined using this information.
(9) Data output file creation (3509), the information for each layer, and possible each block of each layer will be created using the information from the phase wrapping lens (3508).
(10) Data loading to system (3510) wherein the data files (3509) might need additional time to be loaded into the existing software to be analysed and depending on the material the line pitch can be used to fill the 3 dimensional structure.
(11) Patient is positioned towards the system (3611) wherein this positioning is the initial step for the patient interface positioning. The patients head is aligned towards the refractive index shaping work station.
(12) Doctor positions the objective towards the patient's iris (3612) The doctor can use the camera module to get a good idea of the position of the objective towards the iris. This is an important step because this position will also be used for the tracking.
(13) Doctor enters patient ID into the system (3713) wherein the software will display the patient's information and the pre-selected shaping options.
(14) Doctor verifies information and selects START (3714) wherein the doctor verifies in the first step the patient's identity and afterward the selected treatment options.
(15) System checks if laser wavelength is correct (3815) wherein the laser wavelength is selected in regards of the original lens material. The diagnostic tool for of the system afterward checks that the displayed wavelength and the real time value of the system are a match.
(16) System checks if energy is stable (3816) wherein the laser energy is measured. The diagnostic tool for of the system afterward checks that the theoretical calculated energy and the real time value of the system are matching.
(17) System check if pulse width is stable (3817) wherein the diagnostic tool is used to internal check that the pulse width of the system has not changed.
(18) Z module is used for the Z positioning of the focus spot (3918) wherein the Z module is used to vary the distance between the lens shaping focus spot and the iris tracking focus spot. The IOL inside the patient's eye can settle differently and also the patients cornea thickness and anterior chamber thickness is variable, therefore the Z module is used to find the correct location for the refractive index shaping lens.
(19) Scanner is used for the focus spot position (3919) wherein the scanner positions the focus spot to the correct shaping location.
(20) AOM is used for the energy distribution (3920) wherein the AOM provides the correct energy per pulse for the scanner location. and
(21) New lens diopter is verified (4021) wherein the patient's new diopter reading is measured and verified.

This general method may be modified heavily depending on a number of factors, with rearrangement and/or addition/deletion of steps anticipated by the scope of the present invention. Integration of this and other preferred exemplary embodiment methods in conjunction with a variety of preferred exemplary embodiment systems described herein is anticipated by the overall scope of the present invention.

Manufacturing Custom Lens Shaping Method (4100)-(4800)

Figure 41:
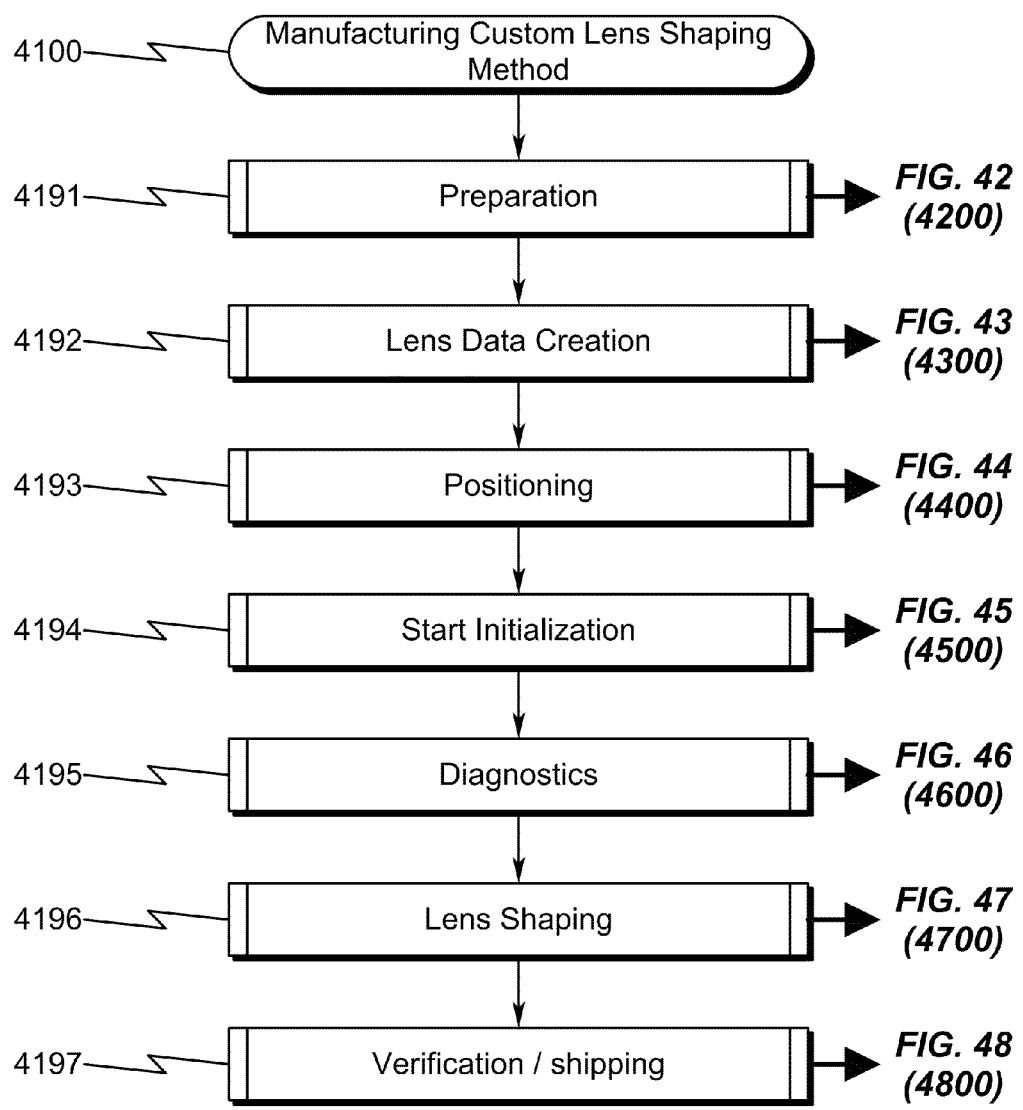
FIG. 41 illustrates an exemplary method flowchart depicting a generalized manufacturing custom lens shaping method as implemented by a preferred invention embodiment.

The present invention anticipates that lenses may be formed/shaped using the systems/methods described herein with a custom manufacturing process as generally illustrated in FIG. 41 (4100), comprising the following steps:

(1) Preparation (4191);
(2) Lens Data Creation (4192);
(3) Positioning (4193);
(4) Start Initialization (4194);
(5) Diagnostics (4195);
(6) Lens Shaping (4196); and
(7) Verification/shipping (4197).

Figure 42:
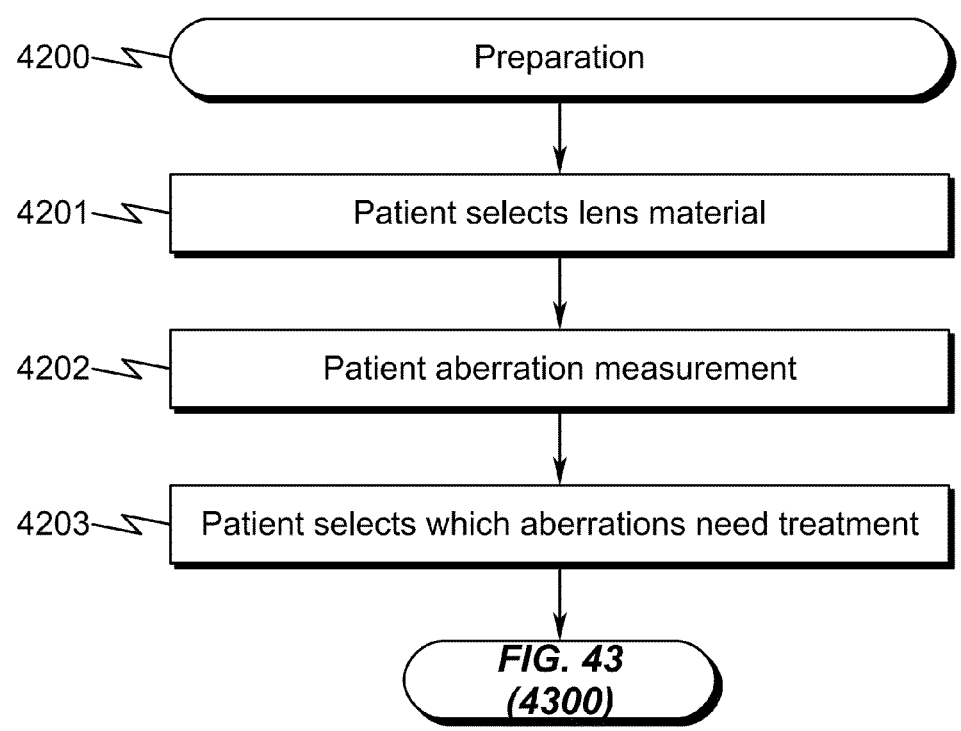
FIG. 42 illustrates an exemplary method flowchart depicting preparation details of a manufacturing custom lens shaping method as implemented by a preferred invention embodiment.
Figure 43:
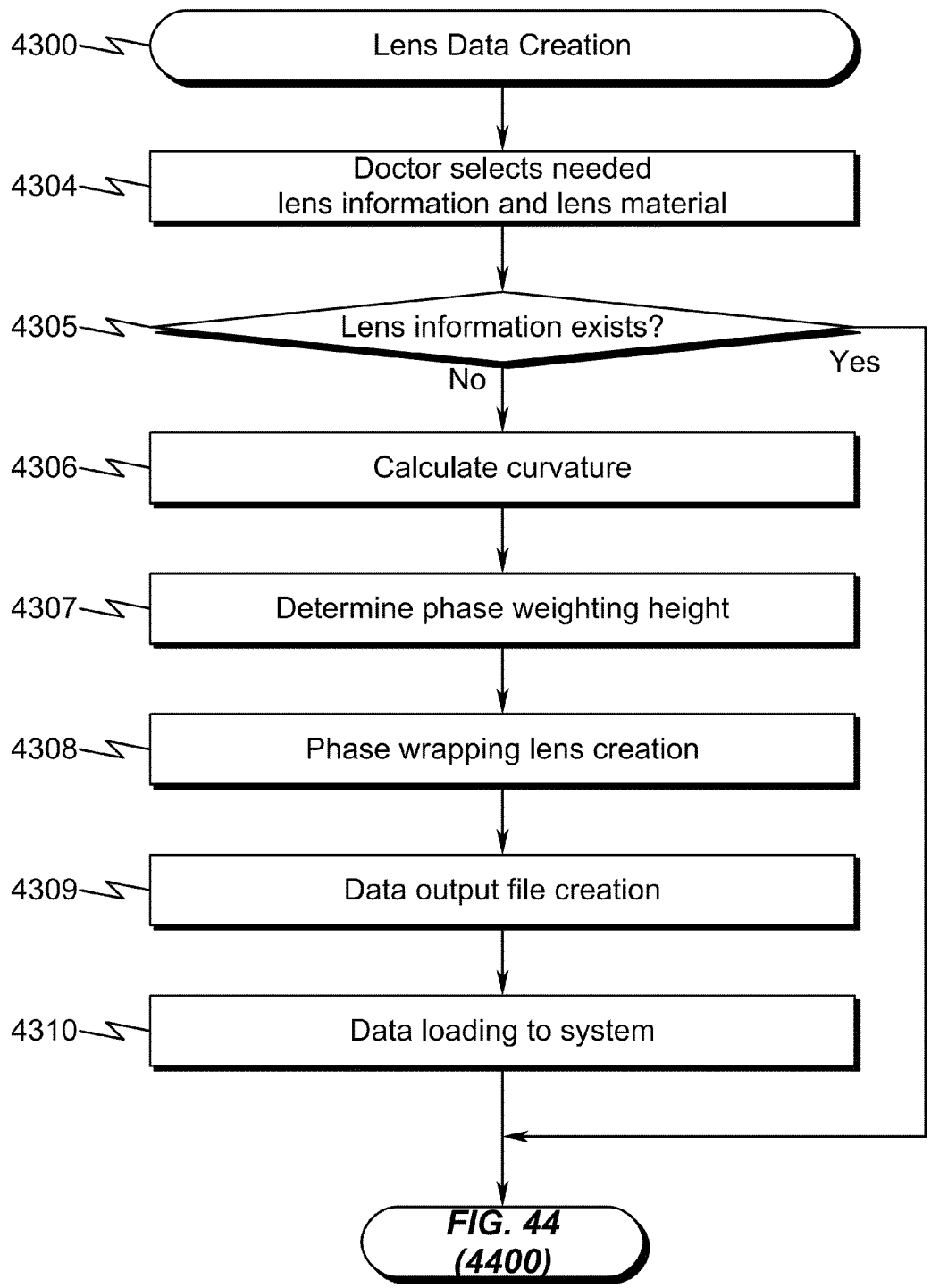
FIG. 43 illustrates an exemplary method flowchart depicting lens data creation details of a manufacturing custom lens shaping method as implemented by a preferred invention embodiment.
Figure 44:
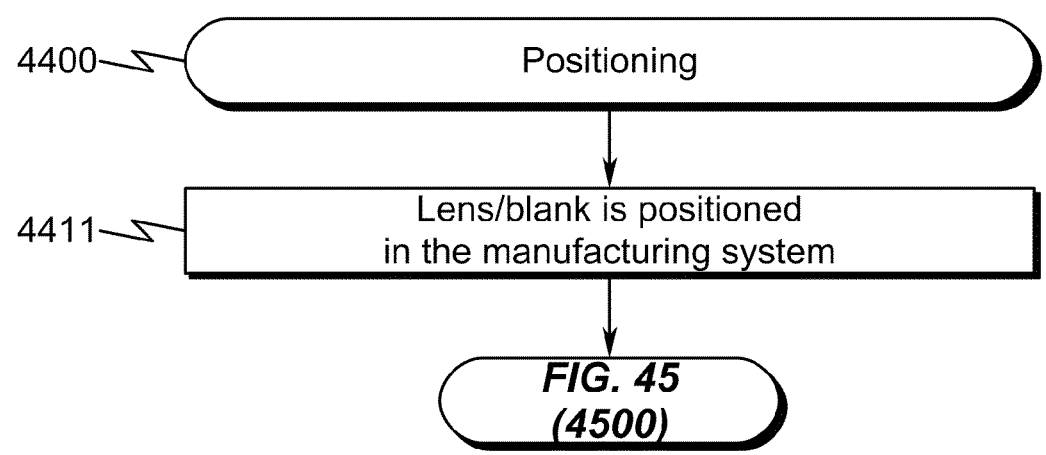
FIG. 44 illustrates an exemplary method flowchart depicting positioning details of a manufacturing custom lens shaping method as implemented by a preferred invention embodiment.
Figure 45:
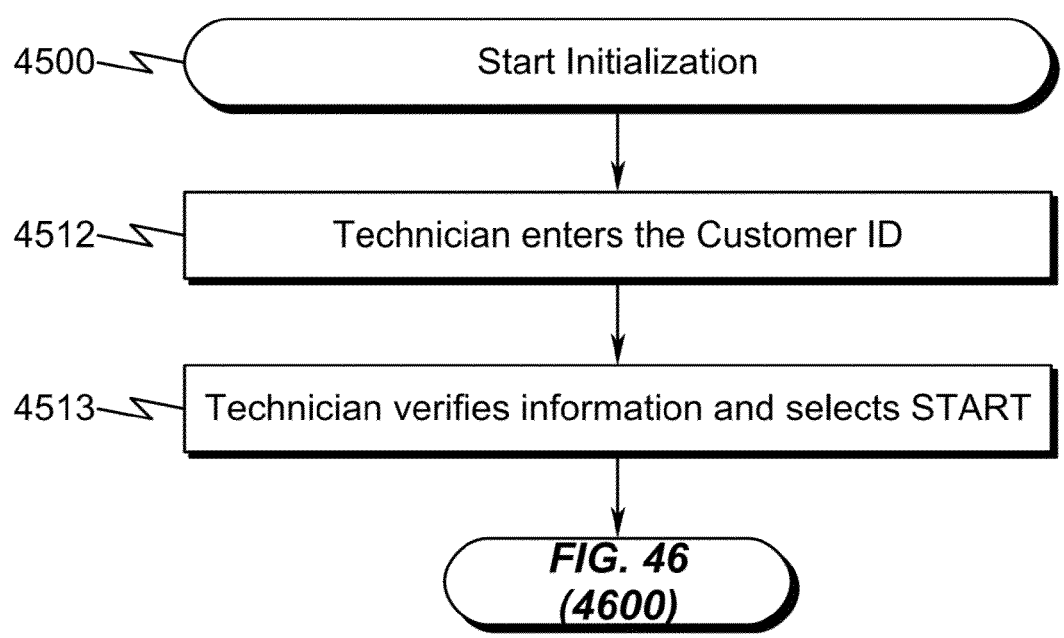
FIG. 45 illustrates an exemplary method flowchart depicting start initialization details of a manufacturing custom lens shaping method as implemented by a preferred invention embodiment.
Figure 46:
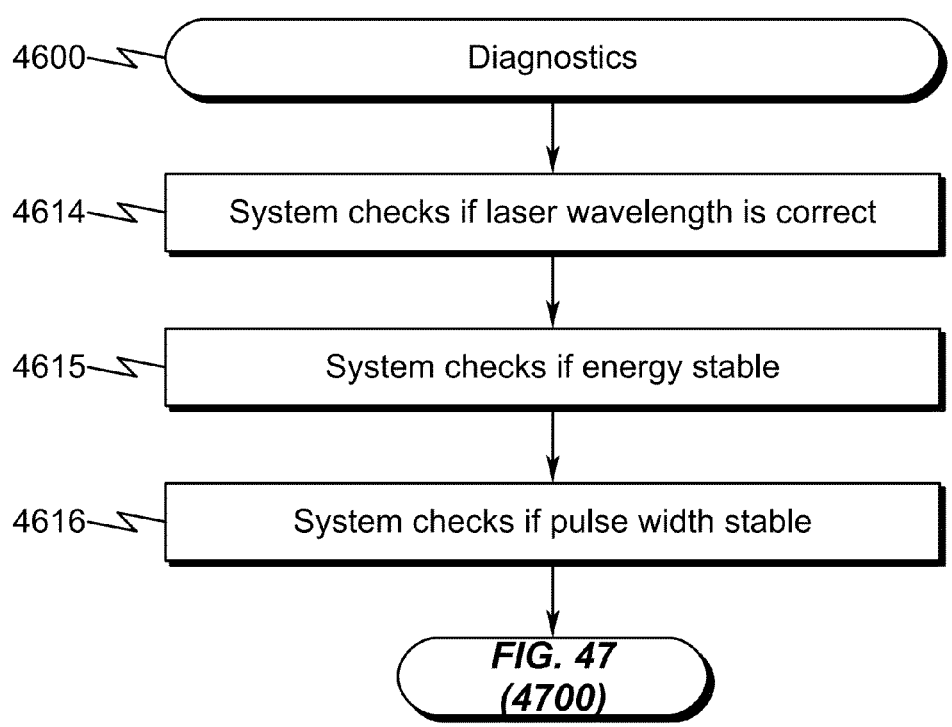
FIG. 46 illustrates an exemplary method flowchart depicting diagnostics details of a manufacturing custom lens shaping method as implemented by a preferred invention embodiment.
Figure 47:
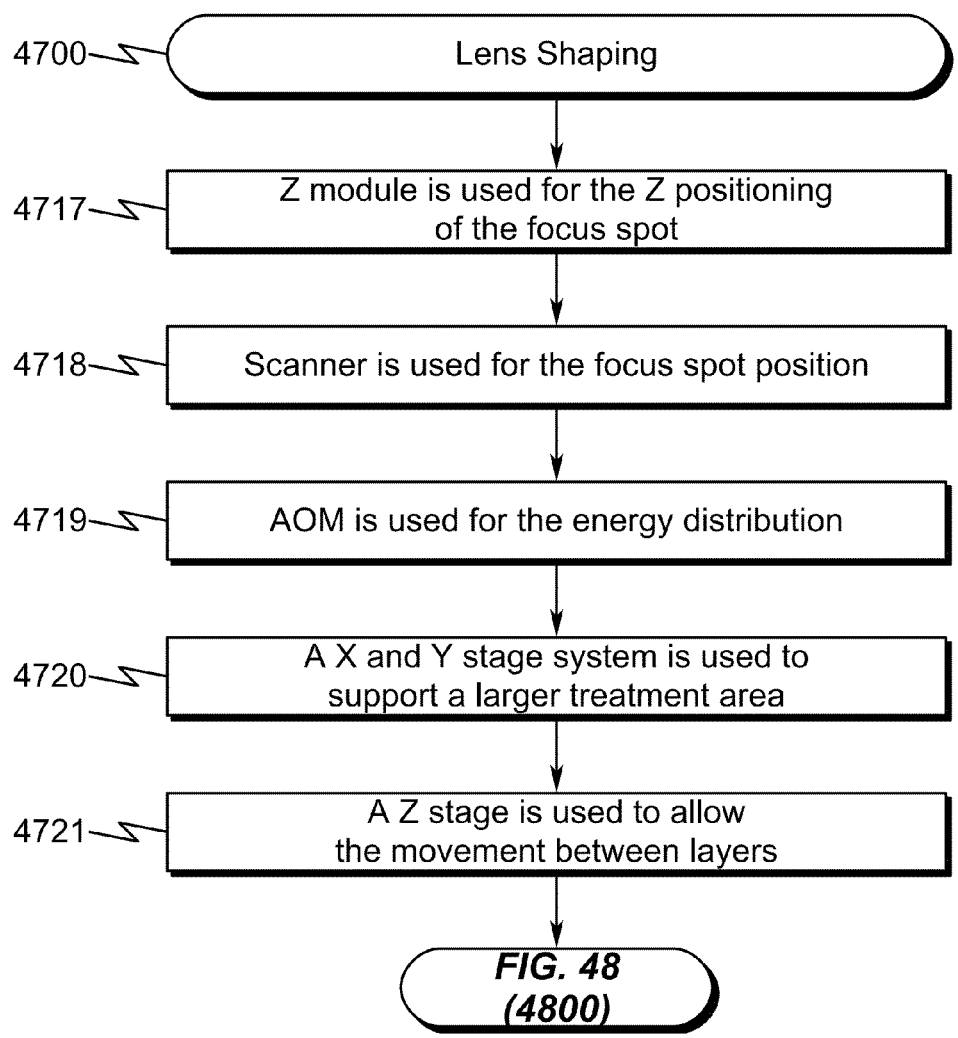
FIG. 47 illustrates an exemplary method flowchart depicting lens shaping details of a manufacturing custom lens shaping method as implemented by a preferred invention embodiment.
Figure 48:
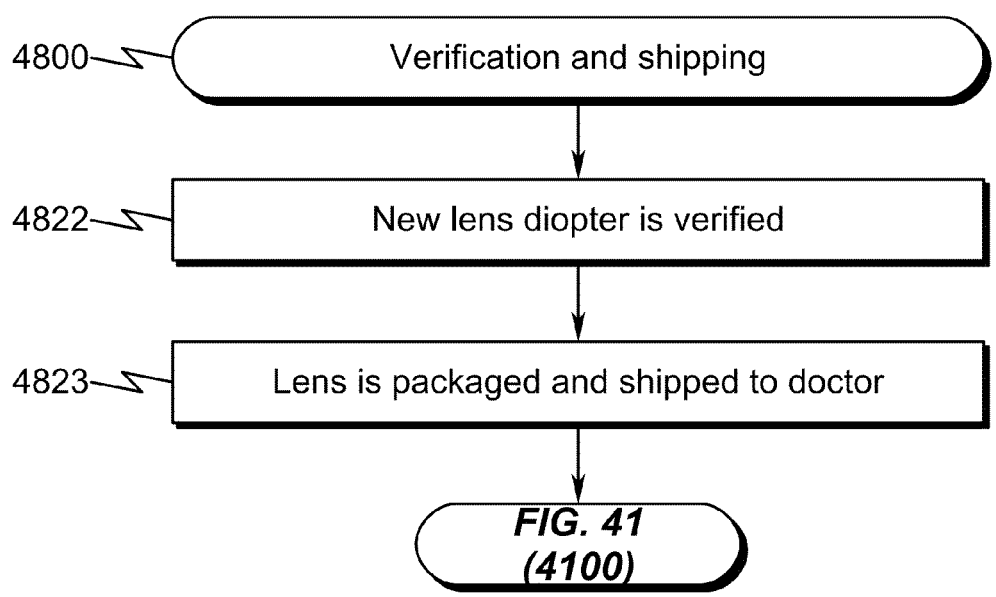
FIG. 48 illustrates an exemplary method flowchart depicting verification/shipping details of a manufacturing custom lens shaping method as implemented by a preferred invention embodiment.

As generally illustrated in FIG. 42 (4200)-FIG. 48 (4800), these generalized steps may be further defined in terms of more detailed steps as follows:

(1) Patient selects lens material determination (4201) wherein the patient has the option to choose the material used from the list of available options.
(2) Patient aberration measurement (4202) wherein the patient's aberrations are measured.

(3) Patient selects which aberrations need treatment (4203) wherein depending on patient's requirement or availability the treatment option is chosen.

(4) Doctor selects needed lens information and lens material (4304) wherein the patient's choice for the material and required changes is revised and if needed a new selection is required and will be discussed with the patient.

(5) Determining if needed lens information exists, and if existing, proceeding to step (11) (4305) wherein the software checks internally if the required aberration code already exists or if new code has to be created for the patient.

(6) Calculating lens curvature (4306) wherein the curvature is depending on the required lens diopter and the refractive index change induced by the refractive index shaping and the surrounding refractive index change of the material.

(7) Determining phase wrapping height (4307) wherein the height is depending on the induced refractive index change difference and therefore also the surrounding material.

(8) Phase wrapping lens creation (4308) wherein the information of the Phase Wrapping Lens is given by the Phase Wrapping Lens height and the original lens curvature information. For each layer the radii for each zone can be determined using this information.

(9) Data output file creation (4309) wherein the information for each layer, and possible each block of each layer will be created using the information from the phase wrapping lens (3508)

(10) Data loading to system (4310) wherein the lens/blank is positioned inside the system.

(11) Lens/blank is positioned in the manufacturing system (4411) wherein the system selects the starting position for the lens shaping.

(12) Technician enters the Customer ID (4512) wherein the software will display the patient's information and the pre-selected shaping options.

(13) Technician verifies information and selects START (4513) wherein the technician verifies in the first step the patient's identity and afterward the selected treatment options.

(14) System checks if laser wavelength is correct (4614) wherein the laser wavelength is selected in regards of the original lens material. The diagnostic tool for of the system afterward checks that the displayed wavelength and the real time value of the system are a match.

(15) System checks if energy is stable (4615) the laser energy is measured. The diagnostic tool of the system afterward checks that the theoretical calculated energy and the real time value of the system are matching.

(16) System check if pulse width is stable (4616) wherein the diagnostic tool is used to internal check that the pulse width of the system has not changed.

(17) Z module is used for the Z positioning of the focus spot (4717) wherein the Z module is used to vary the distance between the lens shaping focus spot and the iris tracking focus spot. The IOL inside the patient's eye can settle differently and also the patients cornea thickness and anterior chamber thickness is variable, therefore the Z module is used to find the correct location for the refractive index shaping lens.

(18) Scanner is used for the focus spot position (4718) wherein the scanner positions the focus spot to the correct shaping location.

(19) AOM is used for the energy distribution (4719) wherein the AOM provides the correct energy per pulse for the scanner location.

(20) A X and Y stage system is used to support a larger treatment area (4720) wherein the X and Y stages are used to shape a lens which is larger than the shaping area of the given objective. and

(21) A Z-stage is used to allow the movement between layers (4721) wherein the Z stage can additional be used for the Z movement of the different layers of the lens.

(22) New lens diopter is verified (4822) wherein the IOL's new diopter reading is measured and verified.

(23) Lens is packaged and shipped to doctor (4823) wherein the product is packed and shipped.

This general method may be modified heavily depending on a number of factors, with rearrangement and/or addition/deletion of steps anticipated by the scope of the present invention. Integration of this and other preferred exemplary embodiment methods in conjunction with a variety of preferred exemplary embodiment systems described herein is anticipated by the overall scope of the present invention.

PM System Summary

The present invention system may be broadly generalized as a system for changing the hydrophilicity of an internal region of a polymeric material, said system comprising:
(a) laser source;
(b) laser scanner; and
(c) microscope objective;
wherein
the laser source is configured to emit a pulsed laser radiation output;
the laser scanner is configured to distribute the pulsed laser radiation output across an input area of the microscope objective;
the microscope objective further comprises a numerical aperture configured to accept the distributed pulsed laser radiation and produce a focused laser radiation output; and
the focused laser radiation output is transmitted by the microscope objective to an internal region of a polymeric material (PM);
the focused laser radiation output changes the hydrophilicity within the internal region of the PM.

This general system summary may be augmented by the various elements described herein to produce a wide variety of invention embodiments consistent with this overall design description.

PLM System Summary

The present invention system anticipates a wide variety of variations in the basic theme of construction, but can be generalized as a lens formation system comprising:
(a) laser source;
(b) laser scanner; and
(c) microscope objective;
wherein
the laser source is configured to emit a pulsed laser radiation output;
the laser scanner is configured to distribute the pulsed laser radiation output across an input area of the microscope objective;
the microscope objective further comprises a numerical aperture configured to accept the distributed pulsed laser radiation and produce a focused laser radiation output; and the focused laser radiation output is transmitted by the microscope objective to a PLM;
the focused laser radiation interacts with the polymers within the PLM and results in a change the hydrophilicity within the PLM.

This general system summary may be augmented by the various elements described herein to produce a wide variety of invention embodiments consistent with this overall design description.

PM Method Summary

The present invention method may be broadly generalized as a method for changing the hydrophilicity of an internal region of a polymeric material, the system comprising:
(1) generating a pulsed laser radiation output from a laser source;
(2) distributing the pulsed laser radiation output across an input area of a microscope objective;
(3) accepting the distributed pulsed radiation into a numerical aperture within the microscope objective to produce a focused laser radiation output; and
(4) transmitting the focused laser radiation output to an internal region of polymeric material ("PM") to modify the hydrophilicity within the internal region of the PM.

This general method may be modified heavily depending on a number of factors, with rearrangement and/or addition/deletion of steps anticipated by the scope of the present invention. Integration of this and other preferred exemplary embodiment methods in conjunction with a variety of preferred exemplary embodiment systems described herein is anticipated by the overall scope of the present invention.

PLM Method Summary

The present invention method anticipates a wide variety of variations in the basic theme of implementation, but can be generalized as a lens formation method comprising:
(1) generating a pulsed laser radiation output from a laser source;
(2) distributing the pulsed laser radiation output across an input area of a microscope objective;
(3) accepting the distributed pulsed radiation into a numerical aperture within the microscope objective to produce a focused laser radiation output; and
(4) transmitting the focused laser radiation output into a PLM to modify the hydrophilicity within the PLM.

This general method may be modified heavily depending on a number of factors, with rearrangement and/or addition/deletion of steps anticipated by the scope of the present invention. Integration of this and other preferred exemplary embodiment methods in conjunction with a variety of preferred exemplary embodiment systems described herein is anticipated by the overall scope of the present invention.

PM Product-by-Process

The present invention method may be applied to the modification of the hydrophilicity of an arbitrary polymeric material, wherein the product-by-process is a modified polymeric material (PM) comprising synthetic polymeric materials further comprising a plurality of modified hydrophilicity zones formed within the polymeric material (PM), the plurality of modified hydrophilicity zones created using a method comprising:
(1) generating a pulsed laser radiation output from a laser source;
(2) distributing the pulsed laser radiation output across an input area of a microscope objective;
(3) accepting the distributed pulsed radiation into a numerical aperture within the microscope objective to produce a focused laser radiation output; and
(4) transmitting the focused laser radiation output to an internal region of polymeric material (PM) to modify the hydrophilicity within the internal region of the PM.

This general product-by-process method may be modified heavily depending on a number of factors, with rearrangement and/or addition/deletion of steps anticipated by the scope of the present invention. Integration of this and other preferred exemplary embodiment methods in conjunction with a variety of preferred exemplary embodiment systems described herein is anticipated by the overall scope of the present invention.

PLM Product-by-Process

The present invention method may be applied to the formation of an optical lens, wherein the product-by-process is an optical lens comprising synthetic polymeric materials further comprising a plurality of optical zones formed within a PLM, the plurality of optical zones created using a lens formation method comprising:
(1) generating a pulsed laser radiation output from a laser source;
(2) distributing the pulsed laser radiation output across an input area of a microscope objective;
(3) accepting the distributed pulsed radiation into a numerical aperture within the microscope objective to produce a focused laser radiation output; and
(4) transmitting the focused laser radiation output into a PLM to modify the hydrophilicity within the PLM.

This general product-by-process method may be modified heavily depending on a number of factors, with rearrangement and/or addition/deletion of steps anticipated by the scope of the present invention. Integration of this and other preferred exemplary embodiment methods in conjunction with a variety of preferred exemplary embodiment systems described herein is anticipated by the overall scope of the present invention.

System/Method/Product-by-Process Variations

The present invention anticipates a wide variety of variations in the basic theme of construction. The examples presented previously do not represent the entire scope of possible usages. They are meant to cite a few of the almost limitless possibilities.

This basic system, method, and product-by-process may be augmented with a variety of ancillary embodiments, including but not limited to:
An embodiment wherein the distribution of the focused laser radiation output is configured to be larger than the field size of the microscope objective by use of an X-Y stage configured to position the microscope objective.
An embodiment wherein the laser source further comprises a femtosecond laser source emitting laser pulses with a megahertz repetition rate.
An embodiment wherein the pulsed laser radiation output has energy in a range of 0.17 to 500 nanojoules.
An embodiment wherein the pulsed laser radiation output has a repetition rate in the range of 1 MHz to 100 MHz.
An embodiment wherein the pulsed laser radiation output has a pulse width in the range of 10 fs to 350 fs.

An embodiment wherein the focused laser radiation output has a spot size in the X-Y directions in the range of 0.5 to 10 micrometers.

An embodiment wherein the focused laser radiation output has a spot size in the Z direction in the range of 0.01 to 200 micrometers.

An embodiment wherein the PLM is shaped in the form of a lens.

An embodiment wherein the PLM is water saturated.

An embodiment wherein the PLM comprises an intraocular lens contained within an ophthalmic lens material.

An embodiment wherein the PLM comprises an intraocular lens contained within an ophthalmic lens material, the ophthalmic lens material located within the eye of a patient.

An embodiment wherein the laser scanner is configured to distribute the focused laser radiation output in a two-dimensional pattern within the PLM.

An embodiment wherein the PLM comprises an intraocular lens contained within an ophthalmic lens material, the ophthalmic lens material located within the eye of a patient.

An embodiment wherein the laser scanner is configured to distribute the focused laser radiation output in a three-dimensional pattern within the PLM.

An embodiment wherein the laser scanner is configured to distribute the focused laser radiation output in a three-dimensional pattern within the PLM, the pattern forming a convex lens within the PLM.

An embodiment wherein the laser scanner is configured to distribute the focused laser radiation output in a three-dimensional pattern within the PLM, the pattern forming a biconvex lens within the PLM.

An embodiment wherein the laser scanner is configured to distribute the focused laser radiation output in a three-dimensional pattern within the PLM, the pattern forming a concave lens within the PLM.

An embodiment wherein the laser scanner is configured to distribute the focused laser radiation output in a three-dimensional pattern within the PLM, the pattern forming a biconcave lens within the PLM.

An embodiment wherein the laser scanner is configured to distribute the focused laser radiation output in a three-dimensional pattern within the PLM; the focused laser radiation creating a hydrophilicity change in the volume associated with the three-dimensional pattern; and the hydrophilicity change resulting in a corresponding change in refractive index of the volume associated with the three-dimensional pattern.

An embodiment wherein the refractive index change is negative for the PLM having an initial refractive index greater than 1.3.

An embodiment wherein the refractive index change is greater than 0.005.

An embodiment wherein the three-dimensional pattern comprises a plurality of layers within the PLM.

An embodiment wherein the PLM comprises a crosslinked polymeric copolymer.

An embodiment wherein the PLM comprises a crosslinked polymeric acrylic polymer.

An embodiment wherein the laser source further comprises an Acousto-Optic Modulator (AOM).

An embodiment wherein the laser source further comprises a greyscale Acousto-Optic Modulator (AOM).

An embodiment wherein the PLM has been presoaked in a liquid solution comprising water.

An embodiment wherein the PLM comprises an ultraviolet (UV) absorbing material.

One skilled in the art will recognize that other embodiments are possible based on combinations of elements taught within the above invention description.

Generalized Computer Usable Medium

In various alternate embodiments, the present invention may be implemented as a computer program product for use with a computerized computing system. Those skilled in the art will readily appreciate that programs defining the functions defined by the present invention can be written in any appropriate programming language and delivered to a computer in many forms, including but not limited to: (a) information permanently stored on non-writeable storage media (e.g., read-only memory devices such as ROMs or CD-ROM disks); (b) information alterably stored on writeable storage media (e.g., floppy disks and hard drives); and/or (c) information conveyed to a computer through communication media, such as a local area network, a telephone network, or a public network such as the Internet. When carrying computer readable instructions that implement the present invention methods, such computer readable media represent alternate embodiments of the present invention.

As generally illustrated herein, the present invention system embodiments can incorporate a variety of computer readable media that comprise computer usable medium having computer readable code means embodied therein. One skilled in the art will recognize that the software associated with the various processes described herein can be embodied in a wide variety of computer accessible media from which the software is loaded and activated. Pursuant to *In re Beauregard,* 35 USPQ2d 1383 (U.S. Pat. No. 5,710,578), the present invention anticipates and includes this type of computer readable media within the scope of the invention. Pursuant to *In re Nuijten,* 500 F.3d 1346 (Fed. Cir. 2007) (U.S. patent application Ser. No. 09/211,928), the present invention scope is limited to computer readable media wherein the media is both tangible and non-transitory.

Conclusion

A system/method allowing the modification of the hydrophilicity of a polymeric material (PM) has been disclosed. The modification in hydrophilicity (i) decreases the PM refractive index, (ii) increases the PM electrical conductivity, and (iii) increases the PM weight. The system/method incorporates a laser radiation source that generates focused laser pulses within a three-dimensional portion of the PM to affect these changes in PM properties. The system/method may be applied to the formation of customized intraocular lenses comprising material (PLM) wherein the lens created using the system/method is surgically positioned within the eye of the patient. The implanted lens refractive index may then be optionally altered in situ with laser pulses to change the optical properties of the implanted lens and thus achieve optimal corrected patient vision. This system/method permits numerous in situ modifications of an implanted lens as the patient's vision changes with age.

A lens formation system/method that permits dynamic in situ modification of the hydrophilicity of the PLM has also been disclosed. The system/method incorporates a laser that generates focused pulses within a three-dimensional portion of PLM to modify the hydrophilicity and thus the refractive index of the PLM and thus create a customized lens of arbitrary configuration. The system/method may be applied to the formation of customized intraocular lenses wherein an ophthalmic lens material incorporating homogeneous PLM is surgically positioned within the eye of a patient. The patient's vision is analyzed with the ophthalmic lens installed and the homogeneous PLM is then irradiated in situ with laser pulses to modify the internal refractive characteristics of the PLM to achieve optimal corrected patient vision. This exemplary application may permit in situ modification of intraocular lens characteristics on a dynamic basis as the patient ages.

What is claimed is:

1. A method for increasing the hydrophilicity of only an internal region of a polymeric material (PM) having a UV absorber, said method comprising:
   (1) generating a pulsed laser radiation output from a laser source having a wavelength selected to interact with said UV absorber within said internal region of said PM;
   (2) distributing said pulsed laser radiation output across an input area of a microscope objective;
   (3) accepting said distributed pulsed radiation into a numerical aperture within said microscope objective to produce a focused laser radiation output;
   (4) transmitting said focused laser radiation output to said internal region within said PM to increase the hydrophilicity of said internal region of said PM;
   (5) exposing said internal region to water; and
   (6) allowing said PM to absorb water thus reducing the refractive index of said internal region of said PM.

2. The method of claim 1 wherein said distribution of said pulsed laser radiation output is configured to he larger than the field size of said microscope objective by use of an X-Y stage configured to position said microscope objective to sequential areas within said PM.

3. The method of claim 1 wherein said laser source further comprises a femtosecond laser source emitting laser pulses.

4. The method of claim 1 wherein said pulsed laser radiation output has energy in a range of 0.17 to 500 nanojoules.

5. The method of claim 1 wherein said pulsed laser radiation output has a repetition rate in the range of 1 MHz to 100 MHz.

6. The method of claim 1 wherein said pulsed laser radiation output has a pulse width in the range of 10 fs to 3.50 fs.

7. The method of claim 1 wherein said pulsed laser radiation output has a spot size in the X-Y directions in the range of 1 to 7 micrometers.

8. The method of claim 1 wherein said pulsed laser radiation output has a spot size in the Z direction in the range of 0.05 to 200 micrometers.

9. The method of claim 1 wherein the polymeric material comprises an acrylic polymeric material (PLM).

10. The method of claim 1 wherein the polymeric material comprises a hydrophobic material.

11. The method of claim 1 wherein transmitting said focused laser radiation further comprises affecting an optical property of said PM.

12. The method of claim 11 wherein the step of affecting an optical property further comprises modifying a diopter value, an asphericity, or a toricity of said PM.

13. A method for decreasing the refractive index of an internal region of a polymeric material (PM), said internal region containing a UV absorber, said method comprising:
   (1) generating a pulsed laser radiation output from a laser source having a wavelength selected to interact with said UV absorber in said PM;
   (2) distributing said pulsed laser radiation output across an input area of a microscope objective;
   (3) accepting said distributed pulsed radiation into a numerical aperture within said microscope objective to produce a focused laser radiation output that focuses on said internal region of said PM;
   (4) directing said focused laser radiation into said internal region;
   (5) exposing said internal region to water; and
   (6) allowing said PM to absorb water this reducing said refractive index of said internal region of said PM.

14. The method of claim 13 wherein said distribution of said pulsed laser radiation output is configured to be larger than the field size of said microscope objective by use of an X-Y stage configured to position said microscope objective to sequential areas within said PM.

15. The method of claim 13 wherein said laser source further comprises a femtosecond laser source emitting laser pulses.

16. The method of claim 13 wherein said pulsed laser radiation output has energy in a range of 0.17 to 500 nanojoules.

17. The method of claim 13 wherein said pulsed laser radiation output has a repetition rate in the range of 0.1 MHz to 100 MHz.

18. The method of claim 13 wherein said pulsed laser radiation output one a pulse width in the range of 10 fs to 350 fs.

19. The method of claim 13 wherein said pulsed laser radiation output has a spot size in the X-Y directions in the range of 1 to 7 micrometers.

20. The method of claim 13 wherein said pulsed laser radiation output has a spot size in the Z direction in the range of 0.05 to 200 micrometers.

21. The method of claim 13 wherein the polymeric material comprises an acrylic polymeric material (PLM).

22. The method of claim 21 wherein the polymeric material comprises a hydrophobic material.

23. The method of claim 13 wherein transmitting the focused laser radiation further comprises affecting an optical property of the polymeric material.

24. The method of claim 13 wherein the step of affecting an optical property further comprises modifying a diopter value, an asphericity, or a toricity of the polymeric material.

25. The method of claim 13 wherein the step of generating a pulsed laser radiation output further comprises interacting with a substituted benzotrazoles or a substituted benzophenoes.

26. The method of claim 13 wherein the step of generating a pulsed laser radiation output further comprises interacting with at least 5% by weight UV absorbers.

27. The method of claim 13 wherein the step of reducing said refractive index further comprises forming a lens.

* * * * *

UNITED STATES PATENT AND TRADEMARK OFFICE
CERTIFICATE OF CORRECTION

PATENT NO.        : 9,023,257 B2
APPLICATION NO.   : 13/843464
DATED             : May 5, 2015
INVENTOR(S)       : Ruth Sahler, Stephen Q. Zhou and Josef F. Bille Page 1 of 1

It is certified that error appears in the above-identified patent and that said Letters Patent is hereby corrected as shown below:

Claims

In Column 29, Claim 6, Line 41, "3.50 fs" should be changed to --350 fs--.

Signed and Sealed this
Twenty-ninth Day of March, 2016

Michelle K. Lee
*Director of the United States Patent and Trademark Office*